(12) United States Patent
Zeman et al.

(10) Patent No.: US 6,458,343 B1
(45) Date of Patent: Oct. 1, 2002

(54) QUATERNARY COMPOUNDS, COMPOSITIONS CONTAINING THEM, AND USES THEREOF

(75) Inventors: William J. Zeman, Janesville, WI (US); Craig Poffenberger, Hilliard, OH (US); Yvonne D. R. Deac, Bad Soden Salmuenster (DE)

(73) Assignee: Goldschmidt Chemical Corporation, Hopewell, VA (US)

( * ) Notice: Subject to any disclaimer, the term of this patent is extended or adjusted under 35 U.S.C. 154(b) by 0 days.

(21) Appl. No.: 09/566,886

(22) Filed: May 8, 2000

Related U.S. Application Data

(63) Continuation-in-part of application No. 09/307,521, filed on May 7, 1999, now abandoned.

(51) Int. Cl.$^7$ .............................................. A61K 7/021
(52) U.S. Cl. ...................... 424/63; 424/690; 424/70.19; 424/70.27; 424/70.28; 510/504; 510/119; 162/111; 162/158
(58) Field of Search ................................ 162/158, 111; 424/490, 63, 70.19, 70.27, 70.28; 510/504, 119

(56) References Cited

U.S. PATENT DOCUMENTS

| | | | | |
|---|---|---|---|---|
| 4,846,992 A | * | 7/1989 | Fonsny | .......................... 252/90 |
| 5,066,414 A | * | 11/1991 | Chang | .......................... 252/8.8 |
| 5,200,097 A | | 4/1993 | Hughes et al. | |
| 5,217,576 A | | 6/1993 | Van Phan | |
| 5,262,007 A | | 11/1993 | Phan et al. | |
| 5,264,082 A | | 11/1993 | Phan et al. | |
| 5,279,767 A | | 1/1994 | Phan et al. | |
| 5,405,501 A | | 4/1995 | Phan et al. | |
| 5,415,737 A | | 5/1995 | Phan et al. | |
| 5,487,813 A | | 1/1996 | Vinson et al. | |
| 5,698,076 A | | 12/1997 | Phan et al. | |
| 5,716,498 A | * | 2/1998 | Jenny et al. | ................. 162/158 |

FOREIGN PATENT DOCUMENTS

| | | |
|---|---|---|
| EP | 0 525 271 A1 | 7/1991 |
| JP | 4-50375 | 2/1992 |
| JP | 07018573 | * 1/1995 |
| JP | 08295657 | * 11/1996 |

* cited by examiner

*Primary Examiner*—Thurman K. Page
*Assistant Examiner*—Lakshmi Channavajjala
(74) *Attorney, Agent, or Firm*—Scully, Scott, Murphy & Presser

(57) ABSTRACT

A composition comprising a compound selected from the group consisting of compounds of the following structural formula (1A):

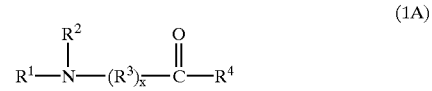

(1A)

and the protonated and quaternized derivatives thereof of the following structural formula (1B):

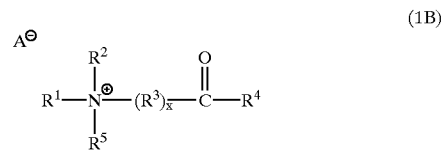

(1B)

wherein $R^1$ is a $C_2$ to $C_{22}$ hydrocarbyl group or is an ether group of the formula $R-O-(R^3)_v-C_3H_6-$, where v is 0 to 10 and R is a $C_1$ to $C_{22}$ hydrocarbyl group;

$R^2$ is hydrogen or a $C_1$ to $C_{22}$ hydrocarbyl group, or is

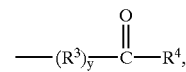

and $(R^3)_yH$, where y is 1 to 100;

each $R^3$ is independently selected from a group consisting of an ethylene oxide group ($C_2H_4O$), a propylene oxide group ($C_3H_6O$), a butylene oxide group ($C_4H_8O$) and mixtures thereof;

each $R^4$ is a $C_3$ to $C_{2}$, hydrocarbyl group;

$R^5$ is hydrogen or a $C_1$ to $C_8$ hydrocarbyl group; and x is 1 to 100; and $A^-$ is an anion.

58 Claims, No Drawings

QUATERNARY COMPOUNDS, COMPOSITIONS CONTAINING THEM, AND USES THEREOF

RELATED APPLICATIONS

This application is a continuation-in-part application of U.S. application Ser. No. 09/307,521, filed May 7, 1999, now abandoned

FIELD OF THE INVENTION

The present invention relates to quaternary ammonium compounds and formulations thereof useful as, for instance, paper debonders, fabric softeners, hair conditioners, skin conditioners, paper deinking and ink floatation agents, asphalt emulsion agents, corrosion inhibitor agents, ore floatation agents, pesticide emulsion agents, car drying aid sprays, drilling fluid additives, and the like.

BACKGROUND OF THE INVENTION

Heretofore quaternary ammonium compounds and a very few dialkyl ammonium compounds ("conventional quats") have found widespread use in many applications. A variety of conventional quats have been proposed for many uses, for example, in fabric softeners for home use or for industrial and institutional use such as paper debonding. In general, such compounds exhibit properties which present some difficulty in the manufacture, formulation use, aesthetic properties, biodegradability, and environmental compatibility of these compositions. Thus, many of the conventional compositions used for these functions, even if completely biodegradable with time, do not biodegrade as rapidly as could be desired and are thus not considered readily biodegradable. In addition, several of the commercial readily biodegradable softeners, conditioners, and debonders do not function as effectively as the conventional products that are less biodegradable. Thus, to maintain effective levels of performance, increased amounts of such less effective, more readily biodegradable products (such as softeners) must be employed and, as will be readily apparent, this factor decreases the cost-effectiveness of the product.

In addition, the color and the odor of the products using conventional quats also pose problems with many biodegradable raw materials. Color stability and low odor are essential to obtaining customer acceptance and to achieving stable and acceptable long-term product aesthetic properties. Such properties are difficult to achieve with conventional quats. Moreover, there is increasing interest in obtaining fabric softener and personal care formulations which are clear (translucent or transparent) liquids, even to the point of obtaining a crystal-clear dispersion when the formulation is dispensed and dispersed into rinse water (even at levels of 50–100 ppm actives in water). Clear formulations may also offer several performance advantages, depending on the application, for example, clear fabric softeners offer reduced staining of the fabric, improved dispersibility, and greatly improved rewetting of the fabric or other substrate. Discovery of such clear compositions requires careful identification of proper quaternary and/or polyquaternary ammonium compounds, together with appropriate additives, such as solvents and cosolvents, which act together to achieve the desired appearance. The relatively poor solubility of conventional quats also contributes to certain difficulties that will vary, depending on the application. For example, when such conventional quats are used in fabric softeners, their poor solubility inhibits the dispersibility of the fabric softener actives into water and the dispersibility of the formulated fabric softener product into the washing machine.

Yamamura et al., Kokai No. 4[1990]50,375 (Application No. 2[1990] 156,249), relates to a fabric softener composition for laundered fabric containing monoalkoxylated alkylamine acid salts, wherein the term "monoalkoxylated" means that the compound does not contain any polymeric chains of alkoxy groups (that is, two or more alkoxy groups attached together). The monoalkoxylated alkylamine acids salts of Yamamura et al. are provided in a fabric softener composition wherein the monoalkoxylated alkylamine acid salts comprise between 2 wt. % and 24 wt. % of the composition. Yamamura et al. differs from the instant invention in that the compositions of Yamamura et al. only contain monoalkoxylated derivatives of their alkylamine acids salts, while the instant invention includes polyalkoxylated derivatives of the compounds of the instant invention, wherein the term "polyalkoxylated" means that the compound contains at least one polymeric chain of alkoxy groups (that is, two or more alkoxy groups attached directly together). Furthermore, Yamamura et al. differs from the instant invention in that the compositions of Yamamura et al. only provide acid salts of their monoalkoxylated alkylamine component, while the instant invention comprises free amines, salts, and quaternized derivatives of the compounds of the instant invention. Moreover, Yamamura et al. differs from the instant invention in that the compositions of Yamamura et al. only provide the monoalkoxylated alkylamine acid salts as a component of a composition that comprises between 2 wt. % and 24 wt. % of the composition and only in combination with other specified ingredients, while the instant invention provides that the compounds of the instant invention can be used alone or in a composition wherein the compounds of the instant invention comprise from 25 wt. % to 100 wt. % of the composition. Lastly, Yamamura et al. differs from the instant invention in that the compositions of Yamamura et al. only are taught for use as a fabric softener composition for laundered fabric, whereas the instant invention provides that the compounds of the instant invention can be used alone or in combination with other components for a variety of other uses, including paper debonding.

Boronat et al., European Patent Application Publication No. 0 525 271 B1, relates to ether amine ester compounds, their quaternary derivatives, and a process for making such compounds. The structure of the ether amine ester compounds of Boronat et al. are distinct from the compounds of the instant invention.

Phan et al., U.S. Pat. No. 5,698,076, ("Phan et al. ('076)") relates to a quaternary ester amine compound and paper web comprising such compounds. The structure of the quaternary ester amine compounds of Phan et al. ('076) are distinct from the compounds of the instant invention, in particular, because they do not contain alkoxylate groups.

Phan et al., U.S. Pat. No. 5,415,737, ("Phan et al. ('737)") relates to a quaternary ester amine compound and paper web comprising such compounds. The structure of the quaternary ester amine compounds of Phan et al. ('737) are distinct from the compounds of the instant invention.

Phan et al., U.S. Pat. No. 5,405,501, ("Phan et al. ('501)") relates to a quaternary ester amine compound and paper web comprising such compounds. The structure of the quaternary amine compounds of Phan et al. ('501) are distinct from the compounds of the instant invention, in particular, because the disclosed prior art compounds do not contain alkoxylate groups.

Phan et al., U.S. Pat. No. 5,279,767, ("Phan et al. ('767)") and Phan et al., U.S. Pat. No. 5,217,576, ("Phan et al.

('576)") each relate to a quaternary ester amine compound and paper web comprising such compounds. The structure of the quaternary amine compounds of Phan et al. ('767) and Phan et al. ('576) are distinct from the compounds of the instant invention, in particular, because the disclosed prior art compounds do not contain alkoxylate groups.

Phan et al., U.S. Pat. No. 5,264,082, ("Phan et al. ('082)") relates to a quaternary ester amine compound and paper web comprising such compounds. The structure of the quaternary ester amine compounds of Phan et al. ('082) are distinct from the compounds of the instant invention.

Phan et al., U.S. Pat. No. 5,262,007, ("Phan et al. ('007)") relates to quaternary ester amine compounds and paper web comprising such compounds. The structure of the quaternary ester amine compounds of Phan et al. ('007) are distinct from the compounds of the instant invention.

Vinson et al., U.S. Pat. No. 5,487,813, relates to a quaternary ester amine compound and a paper web comprising such compounds and carboxymethyl cellulose and cationic starch.

Certain ester quaternary compounds, for example, 2-[(2-hydroxyethyl)octadecylamino]ethyl stearate (CAS Registry Number 52497-24-2), (octadecylimino)diethylene distearate (CAS Registry Number 94945-28-5), and octadecyl bis (hydroxyethyl)amine have been previously used as antistatic and/or antifogging additives for plastics, in particular, for food packaging materials in accordance with 21 C.F.R. §178.3130.

Thus, there remains a need for identification of new amine and ammonium derivatives which are useful as fabric softeners and paper debonders and which are also biodegradable, highly effective in softening, debonding, conditioning, and the like, and yet avoid these problems upon manufacture, formulation and use. It is also desirable for the active agents used in hair and skin conditioners, paper debonding compositions, textile softeners, and the like, to be readily biodegradable and to exhibit a satisfactorily high activity. Conventional products have to date not been able to exhibit both properties to a high degree, thus necessitating acceptance of reduced biodegradability or reduced activity. There is thus still a need for compounds exhibiting levels of activity as conditioners, paper debonders, and so on, as the case may be, which are comparable or superior to conventionally employed actives, such as conventional quats, while also exhibiting ready biodegradability.

As can be appreciated, the chemistry of fabric softeners, paper debonders, hair conditioners, skin conditioners, textile softeners, car wax sprays, and the like is challenging. Each of these applications presents its own complications, because the interactions between the various components of the compositions must be considered in addition to the individual chemistry of each component.

SUMMARY OF THE INVENTION

The present invention achieves these objectives and also exhibits the properties and advantages described herein.

One aspect of the present invention comprises compounds of the following structural formula (hereinafter "structural formula (IA)"):

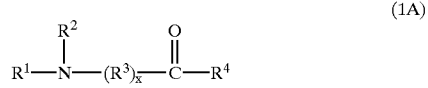
(1A)

and the protonated and quaternized derivatives thereof (hereinafter "structural formula (1B)"):

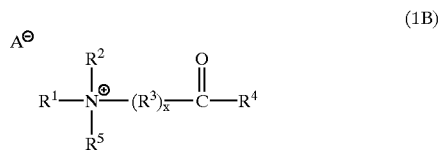
(1B)

wherein
$R^1$ is a $C_2$ to $C_{22}$, preferably $C_3$ to $C_{22}$, more preferably $C_4$ to $C_{22}$, even more preferably $C_5$ to $C_{22}$ or $C_6$ to $C_{22}$, or $C_7$ to $C_{22}$, and most preferably $C_8$ to $C_{22}$, hydrocarbyl group or is an ether group of the formula R—O—$(F^3)_v$—$C_3H_6$—, where v is 0 to 10 and R is a $C_1$ to $C_{22}$, preferably $C_4$ to $C_{22}$, hydrocarbyl group;
$R^2$ is hydrogen or a $C_1$ to $C_{22}$ hydrocarbyl group, or is

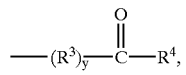

or $(R^3)_yH$, where y is 1 to 100;
each $R^3$ is independently selected from a group consisting of an ethylene oxide group ($C_2H_4O$), a propylene oxide group ($C_3H_6O$), a butylene oxide group ($C_4H_8O$) and mixtures thereof;
each $R^4$ is a $C_3$ to $C_{21}$, preferably $C_{11}$ to $C_{21}$, hydrocarbyl group;
$R^5$ is hydrogen or a $C_1$ to $C_8$ hydrocarbyl group; and
x is 1 to 100; and
$A^{31}$ is an anion as defined below.

As used herein, the term "alkyl" refers to fully saturated linear (straight-chain) and branched hydrocarbon groups, for example, alkyl includes linear and branched methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and eicosyl groups. As used herein, the term "alkenyl" refers to linear or branched hydrocarbon groups containing at least one carbon-carbon double bond. As used herein, the term "alkynyl" refers to linear or branched hydrocarbon groups containing at least one carbon-carbon triple bond. As used herein, the term "aliphatic" refers to linear or branched, saturated or unsaturated, hydrocarbon groups, that is, alkyl groups, alkenyl groups, and alkynyl groups. As used herein, the terms "cycloalkyl" or "cyclic alkyl" refer to fully saturated hydrocarbon groups containing one, two, three, or more cyclic rings. As used herein, the terms "cycloalkenyl" or "cyclic alkenyl" refers to hydrocarbon groups containing one, two, three, or more cyclic rings and at least one double carbon-carbon double bond in the ring, for example, a cyclohexenyl group. As used herein, the term "cycloaliphatic" refers herein to saturated or unsaturated hydrocarbon groups containing one, two, three, or more cyclic rings, that is, cycloalkyl groups and cycloalkenyl groups. As used herein, the term "aryl" refers to a group that contains one or more aromatic rings, for example, aryl includes biaryl; biphenylyl; phenyl; naphthyl; phenanthranyl; anthranyl; N-alkyl and N,N-dialkyl anilines; o-, m- and p-nitrophenyl; o-, m- and p-alkyl phenyl; 2-, 3-, and 4-halophenyl; 2-, 3-, and 4-carboxyphenyl and esters thereof; phenol; two aryl groups bridged by an alkylene group; and the substituted derivatives thereof. As used herein, the terms "alkaryl" or "alkylaryl" refer to an alkyl-, alkenyl- or alkynyl-substituted aryl group. As used herein, the terms "aralkyl" or "arylalkyl" refer to an alkyl, alkenyl, or alkynyl group substituted with an aryl group. Examples of aralkyl, include benzyl and substituted benzyl moieties; benzyl halides; benzhydryl halides; trityl halides; a-halo-a-phenylalkanes, such as 1 halo-1-phenylethane, 1-halo-1-phenylpropane, and 1-halo-1-phenyloctadecane; o-, m- and p-chlorobenzyl halides; p-methoxybenzyl halides; o-, m- and p-nitrilobenzyl halides, and o-, m- and p-alkylbenzyl halides. As used herein, the term "hydrocarbyl" refers to aliphatic, cycloaliphatic, aryl, alkaryl, and aralkyl groups. It should be noted that these classifications are not necessarily exclusive for a particular group; thus, a linear aliphatic group containing both a carbon-carbon double bond and a carbon-carbon triple bond may be considered an alkenyl group, an alkynyl group, or both. It is understood that cyclic structures, for example, cycloaliphatic groups and aryl groups, require at least three carbon atoms to form a ring and therefore a term such as "$C_1$ to $C_{22}$" when applied to or modifying such a cyclic structure or applied to a term, for example hydrocarbyl, that includes such cyclic groups, is understood to actually designate only cyclic groups containing 3 to 22 carbon atoms for these cyclic groups.

In preferred embodiments of the invention, the hydrocarbyl groups of $R^1$, $R^2$, $R^4$, and $R^5$ of the compounds of structural formulas (1A) and (1B) are each independently limited to aliphatic, cycloaliphatic, aryl, alkaryl, and aralkyl groups. In other preferred embodiments of the invention, the hydrocarbyl groups of $R^1$, $R^2$, $R^4$, and $R^5$ of the compounds of structural formulas (1A) and (1B) are each independently further limited to alkyl groups, alkenyl groups, and alkynyl groups, each of which may be independently further limited to linear or branched groups; and cycloalkyl groups and cycloalkenyl groups.

In a preferred embodiment of the invention, the compositions and/or formulations of the instant invention comprise compounds of structural formulas (1A) and (1B) which do not contain a significant amount of polymers, plasticizers, polymer stabilizers, or any polymers, plasticizers, or polymer stabilizers. The term "polymers" as used in this paragraph comprises plastics, resins, or polymers known to those of skill in the art that may be selected, without limitation, from the group consisting of natural and synthetic organic polymers, plastics and resins, including aliphatics, polyamides, polyolefins, polypropylenes, polyethylenes, epoxies, polyesters, polycarbonates, polystyrenes, thermoplastics, polyurethanes, polyvinyls, aromatics, nitrogen-containing polymers, synthetic or natural rubbers, phosphorous-containing polymers, or the copolymers, resins, alloys, or blends thereof. The term "polymers" as used in this paragraph does not include the strength additives set forth below in section I. OTHER ADDITIVES, subsection 1. Papermaking and Tissuemaking Additives, subdivision B. Strength Additives.

In a preferred embodiment of the invention, the compositions and/or formulations of the instant invention comprise compounds of structural formulas (1A) and (1B) which do not contain a significant amount of imidazoline compounds, imidazolinium compounds, or imidazoline-derived compounds or any imidazoline compounds, imidazolinium compounds, or imidazoline-derived compounds.

In a preferred embodiment of the invention, the compounds of structural formulas (1A) and (1B) are provided as compositions and/or formulations wherein the compounds of structural formulas (1A) and (1B) comprise 25 wt. % to 100 wt. % of the total composition, more preferably 40 wt. % to 100 wt. % of the total composition, even more preferably 60 wt. % to 100 wt. % of the total composition, and most preferably 75 wt. % to 100 wt. % of the total composition.

In a preferred embodiment of the invention, x is 2 to 50, more preferably x is 3 to 40, even more preferably x is 3 to 30, and most preferably x is 3 to 15. In a preferred embodiment of the invention, $R^1$ is a linear $C_{14}$ to $C_{22}$ alkyl or alkylene group, more preferably $R^1$ is a linear $Cm_{,6}$ to $C_{18}$ alkyl or alkylene group, and most preferably $R^1$ is selected from the group consisting of stearyl, tall oil fatty acid (TOFA), soya, tallow, canola, and oleyl. In a preferred embodiment of the invention, $R^2$ is a linear or branched $C_1$ to $C_{18}$ alkyl or alkylene group, more preferably $R^2$ is a linear or branched $C_{12}$ to $C_{18}$ alkyl or alkylene group, even more preferably $R^2$ is a linear or branched $C_{14}$ to $Cm_{,8}$ alkyl or alkylene group, and most preferably $R^2$ is a linear or branched $C_{16}$ to $C_{18}$ alkyl or alkylene group. In yet another preferred embodiment of the invention $R^2$ is

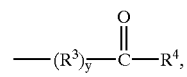

or $(R^3)_yH$, where y is 3 to 50, more preferably y is 3 to 30, and most preferably y is 3 to 15. In a preferred embodiment of the invention, each $R^4$ is independently a linear, branched, or cyclic $C_{13}$ to $C_{21}$ alkyl or alkylene group, more preferably each $R^4$ is independently a linear, branched, or cyclic $C_{15}$ to $C_{21}$ alkyl or alkylene group, and most preferably each $R^4$ is independently a linear, branched, or cyclic $C_{17}$ to $C_{21}$ alkyl or alkylene group. In a preferred embodiment of the invention, $R^5$ is hydrogen, benzyl, or a linear, branched, or cyclic $C_1$ to $C_6$ alkyl or alkylene group, more preferably $R^5$ is hydrogen, benzyl, or a linear or branched $C_1$ to $C_3$ alkyl or alkylene group, and most preferably $R^5$ is hydrogen, methyl, ethyl, or benzyl. In preferred embodiments of the invention, one or more of $R^1$, $R^2$, $R^4$, or $R^5$ does not include any hydroxyl groups. In preferred embodiments of the invention, one or more of $R^1$, $R^2$, $R^4$, or $R^5$ does not include any groups that contain atoms other than hydrogen, carbon, or oxygen.

For home care and personal care products, it is preferred that the compounds of structural formulas (1A) and (1B) contain $R^1=C_8$ to $C_{22}$ hydrocarbyl group or ether wherein $R=C_4$ to $C_{22}$ hydrocarbyl group and $R^4=C_{11}$ to $C_{21}$ hydrocarbyl group.

Another aspect of the present invention comprises compounds of the following structural formula (hereinafter "structural formula (2A)"):

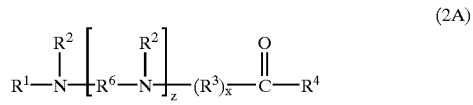

(2A)

and the protonated and quaternized derivatives thereof (hereinafter "structural formula (2B)"):

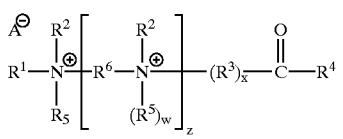

(2B)

wherein $R^1$ is a $C_2$ to $C_{22}$, preferably $C_3$ to $C_{22}$, more preferably $C_4$ to $C_{22}$, even more preferably $C_5$ to $C_{22}$ or $C_6$ to $C_{22}$, or $C_7$ to $C_{22}$, and most preferably $C_8$ to $C_{22}$, hydrocarbyl group or is an ether group of the formula R—O—$(R^3)_v$—$C_3H_6$—, where v is 0 to 10 and R is a $C_4$ to $C_{22}$ hydrocarbyl each $R^2$ is independently selected from the group consisting of hydrogen, a $C_1$ to $C_{22}$ hydrocarbyl group,

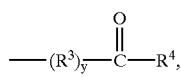

and $(R^3)_y H$, where y is 1 to 100;

each $R^3$ is independently selected from the group consisting of an ethylene oxide group ($C_2H_4O$), a propylene oxide group ($C_3H_6O$), a butylene oxide group ($C_4H_8O$) and mixtures thereof;

each $R^4$ is independently a $C_3$ to $C_{21}$, preferably $C_{11}$ to $C_{21}$, hydrocarbyl group;

each $R^5$ is independently hydrogen or a $C_1$ to $C_6$ hydrocarbyl group, where each w is independently 0 or 1;

each $R^6$ is independently a $C_1$ to $C_8$ hydrocarbyl group;

x is 1 to 100;

z is 1, 2, 3, 4 or 5; and $A^-$ is an anion as defined below that balances the charge of the compound.

In preferred embodiments of the invention, the hydrocarbyl groups of $R^1$, $R^2$, $R^4$, $R^5$, and $R^6$ of the compounds of structural formulas (2A) and (2B) are each independently limited to aliphatic, cycloaliphatic, aryl, alkaryl, and aralkyl groups. In other preferred embodiments of the invention, the hydrocarbyl groups of $R^1$, $R^2$, $R^4$, $R^5$, and $R^6$ of the compounds of structural formulas (2A) and (2B) are each independently further limited to alkyl groups, alkenyl groups, and alkynyl groups, each of which may be independently further limited to linear or branched groups; and cycloalkyl groups and cycloalkenyl groups.

In a preferred embodiment of the invention, the compositions and/or formulations of the instant invention comprise compounds of structural formulas (2A) and (2B) which do not contain a significant amount of polymers, plasticizers, polymer stabilizers, or any polymers, plasticizers, or polymer stabilizers. The term "polymers" as used in this paragraph comprises plastics, resins, or polymers known to those of skill in the art that may be selected, without limitation, from the group consisting of natural and synthetic organic polymers, plastics and resins, including aliphatics, polyamides, polyolefins, polypropylenes, polyethylenes, epoxies, polyesters, polycarbonates, polystyrenes, thermoplastics, polyurethanes, polyvinyls, aromatics, nitrogen-containing polymers, synthetic or natural rubbers, phosphorous-containing polymers, or the copolymers, resins, alloys, or blends thereof. The term "polymers" as used in this paragraph does not include the strength additives set forth below in section 1. OTHER ADDITIVES, subsection 1. Papermaking and Tissuemaking Additives, subdivision B. Strength Additives.

In a preferred embodiment of the invention, the compositions and/or formulations of the instant invention comprise compounds of structural formulas (2A) and (2B) which do not contain a significant amount of imidazoline compounds, imidazolinium compounds, or imidazoline-derived compounds or any. imidazoline compounds, imidazolinium compounds, or imidazoline-derived compounds.

In a preferred embodiment of the invention, the compounds of structural formulas (2A) and (2B) are provided as compositions and/or formulations wherein the compounds of structural formulas (2A) and (2B) comprise 25 wt. % to 100 wt. % of the total composition, more preferably 40 wt. % to 100 wt. % of the total composition, even more preferably 60 wt. % to 100 wt. % of the total composition, and most preferably 75 wt. % to 100 wt. % of the total composition.

In a preferred embodiment of the invention, x is 2 to 50, more preferably x is 3 to 40, even more preferably x is 3 to 30, and most preferably x is 3 to 15. In a preferred embodiment of the invention, z is 1 or 2, more preferably z is 1. In a preferred embodiment of the invention, $R^1$ is a linear $C_{14}$ to $C_{22}$ alkyl or alkylene group, more preferably $R^1$ is a linear $C_{16}$ to $C_{18}$ alkyl or alkylene group, and most preferably $R^1$ is selected from the group consisting of stearyl, tall oil fatty acid (TOFA), soya, tallow, canola, and oleyl. In a preferred embodiment of the invention, each $R^2$ is independently a linear or branched $C_1$ to $C_{18}$ alkyl or alkylene group, more preferably each $R^2$ is independently a linear or branched $C_{12}$ to $C_{18}$ alkyl or alkylene group, even more preferably each $R^2$ is independently a linear or branched $C_{14}$ to $C_{18}$ alkyl or alkylene group, and most preferably $R^2$ is a linear or branched $C_{16}$ to $C_{18}$ alkyl or alkylene group. In yet another preferred embodiment of the invention one or more of $R^2$ is independently a

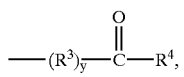

or $R_3)_y H$, where y is 3 to 50, more preferably y is 3 to 30, and most preferably y is 3 to 15. In a preferred embodiment of the invention, each $R^4$ is independently a linear, branched, or cyclic $C_{13}$ to $C_{21}$ alkyl or alkylene group, more preferably each $R^4$ is independently a linear, branched, or cyclic $C_{15}$ to $C_{21}$ alkyl or alkylene group, and most preferably each $R^4$ is independently a linear, branched, or cyclic $C_{17}$ to $C_{21}$ alkyl or alkylene group. In a preferred embodiment of the invention, $R^5$ is hydrogen, benzyl, or a linear, branched, or cyclic $C_1$ to $C_6$ alkyl or alkylene group, more preferably $R^5$ is hydrogen, benzyl, or a linear or branched $C_1$ to $C_3$ alkyl or alkylene group, and most preferably $R^5$ is hydrogen, methyl, ethyl, or benzyl. In a preferred embodiment of the invention, $R^6$ is a linear, branched, or cyclic $C_1$ to $C_6$ alkyl or alkylene group, more preferably $R^6$ is a linear, branched, or cyclic $C_3$ to $C_6$ alkyl or alkylene group, most preferably $R^6$ is a linear, branched, or cyclic $C_3$ to $C_5$ alkyl or alkylene group containing 3 to 5 carbon atoms. In preferred embodiments of the invention, one or more of $R^1$, $R^2$, $R^4$, $R^5$, or $R^6$ does not include any hydroxyl groups. In preferred embodiments of the invention, one or more of $R^1$, $R^2$, $R^4$, $R^5$, or $R^6$ does not include any groups that contain atoms other than hydrogen, carbon, or oxygen.

In home care and personal care products, it is preferred that compounds of structural formulas (2A) and (2B) contain $R^1 = C_8$ to $C_{22}$ hydrocabon or ether wherein $R = C_4$ to $C_{22}$ hydrocarbyl group; and $R^4 = C_{11}$ to $C_{21}$ hydrocarbyl group.

As used herein, the term "structural formula (1)" is intended to designate either or both of structural formula (1A) and structural formula (1)B); and the term "structural formula (2)" is intended to designate either of both or structural formula (2A) and structural formula (2B). The compounds of structural formulas (1) and (2), whether in the ester amine form, that is, structural formulas (1A) and (2A), or the protonized species or the quaternized species thereof, that is, structural formulas (1B) and (2B), shall hereinafter be referred to as "Inventive Ester Quats".

If $R^5$ is present, the Inventive Ester Quats are protonized amines or quaternized amines and include an anion $A^-$ which is present in a number of moles equal to the total positive charge of the nitrogen-containing cation thereof (although such may not be explicitly indicated in structural formulas (1)B) and (2B)). The anion $A^-$ can represent any anion which is not deleterious to the properties of the overall compound. Non-limiting examples of $A^-$ include fluoride, chloride, bromide, iodide, chlorite, chlorate, hydroxide, hypophosphite, phosphite, phosphate, carbonate, formate, acetate, citrate, lactate, and other carboxylates, oxalate, methyl sulfate, ethyl sulfate, benzoate, and salicylate, and the like. Preferred examples are chloride, bromide, citrate, acetate, methyl sulfate, ethyl sulfate, and salicylate. If the anion is monovalent (has a charge of –1), $A^-$ represents the anion group, if the anion is divalent (has a charge of –2), $A^-$ represents half of the anion group, if the anion is trivalent (has a charge of –3), $A^-$ represents a third of the anion group, and so on.

The invention also provides a paper web comprising (a) papermaking fibers; and (b) Inventive Ester Quats. In preferred embodiments of the invention, the Inventive Ester Quats comprise from about 0.005% to 5.0% by weight of the papermaking fibers; more preferably from about 0.01% to about 3.0% by weight of the papermaking fibers; even more preferably from about 0.05% to about 2.5% by weight of the papermaking fibers; and most preferably from about 0.1% to about 2.0% by weight of the papermaking fibers.

As used herein, the terms "paper", "paper web", "web", "paper sheet", "tissue", or "tissue paper" is intended to designate an of the nonwoven materials commonly used as paper products, including tissue paper, from which at least a portion thereof comprises papermaking fibers, which may be selected, without limitation, from the group consisting of: hardwood fibers, softwood fibers, recycled fibers, baggasse fibers, fluff pulp, and natural papermaking fibers, synthetic papermaking fibers, cellulosic fibers, and blends thereof.

The invention also provides an organoclay composition made by the reaction of: (a) one or more clays; and (b) one or more compounds selected from the group consisting of (I) compounds of structural formula (1B) and (ii) compounds of structural formula (2B). In a preferred embodiment of the invention, the clay is a smectite clay selected from the group consisting of bentonite and hectorite. In another preferred embodiment of the invention, component (b) is added in an amount sufficient to react completely with the cation exchange capacity of the clay.

The invention also provides a process for preparing an organoclay composition which comprises: (a) preparing a slurry of one or more clays; (b) heating the slurry to a temperature between 20° C. and 100° C.; (c) adding to the heated slurry one or more compounds selected from the group consisting of: (I) compounds of structural formula (1B) and (ii) compounds of structural formula (2B). In a preferred method according to the invention, the process further comprises a step (e) recovering and drying the organoclay composition.

Ranges in amounts given for each ingredient or component of a composition or formulation set forth herein in certain circumstances may be theoretically capable of adding up to a sum of greater than 100%. As would be appreciated by those of skill in the art, it is understood that such impossible formulations (that is, those formulations whose component amounts add to a sum greater than 100%) are excluded from the claims and disclosure. For example, a formulation m. m having components A and B, where the amount of A is said to range from 25% to 75% and the amount of B is said to range from 25% to 55%, if containing 65% of A, is understood to have 35% or less of B in that formulation, so that the sum of A and B does not exceed 100%. Thus, all formulations or compositions presented herein whose component amounts add to a sum less than or equal to 100% are understood as being part of the claims and disclosure.

DETAILED DESCRIPTION OF THE INVENTION

The present invention is directed to novel amine compounds and quaternary compounds, compositions and formulations containing such novel compounds, and uses thereof.

A. Preferred Compounds and Compositions

As will be appreciated, a particularly preferred embodiment of the present invention comprises mixtures of Inventive Ester Quats, such that degrees of quaternization or protonation (including unquaternized, unprotonated compounds), degrees of esterification, and chain lengths and molecular weights of different molecules within the mixture will differ such that the respective properties can be represented as an average over all the molecules present in the mixture. In such mixtures, then, properties such as the degree of quaternization can be expressed as average values which may lie between integer whole numbers.

It can be seen that the Inventive Ester Quat structures embrace compounds ranging from compounds wherein no nitrogen atom is quaternized or protonated with a corresponding substituent and compounds wherein every nitrogen atom is quaternized or protonated with a substituent. Furthermore, for Inventive Ester Quats that contain more than one nitrogen atom per molecule, that is, those of structural formulas (2A) and (2B), the term "partially" is meant to convey that at least one nitrogen atom on the Inventive Ester Quat molecule does not have a substituent attached to it, and preferred embodiments of the instant invention include Inventive Ester Quats which are partially quaternized or protonated. Thus, the instant invention includes Inventive Ester Quats and mixtures thereof, in which there are either no substituents or the only substituents present are —H. Such substituents can be present in a degree such that all nitrogen atoms are protonated, or fewer than all nitrogen atoms are protonated ("full" and "partial" protonation, respectively). Although many of the teachings and disclosure below uses the terms "quaternary compounds" or "quats" and similar language with respect to applications and formulations including Inventive Ester Quats, such disclosures should be understood to apply equally to the non-quaternized (i.e., ester amine) Inventive Ester Quats, unless specifically and unambiguously excluded.

The acyl groups on the Inventive Ester Quats can all have the same chain lengths. More preferably they have several chain lengths and degrees of carbon-carbon unsaturation, reflecting the fact that the fatty acyl groups can be derived from naturally occurring sources which contain mixtures of fatty acids with differing chain lengths and differing degrees of carbon-carbon unsaturation. Examples of such sources include fatty acids derived from the following sources: tallow, tall oil fatty acid (TOFA), fish oils, canola (including fatty acids derived from partially hydrogenated canola), jojoba, palm, coconut, avocado, wheat germ, rapeseed, olive, orange, corn, linseed, neem, peanut, safflower, sesame seed, soybean, sunflower seed, and cocoa butter. Preferred materials are tallow, canola, and palm.

Further preferred embodiments of Inventive Ester Quats are described herein with respect to the various formulation capabilities of the products of this invention.

Inventive Ester Quats, when quaternized and/or protonated to any degree, include an anion $A^-$ which is present in a number of moles equal to the total positive charge of the nitrogen-containing cation. The anion $A^-$ can represent any anion which is not deleterious to the properties of the overall compound. Non-limiting examples of $A^-$ include fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like. Preferred examples are chloride, bromide, citrate, acetate, methyl sulfate, ethyl sulfate, and salicylate. If the anion is monovalent (has a charge of −1), $A^-$ represents the anion group, if the anion is divalent (has a charge of −2), $A^-$ represents half of the anion group, if the anion is trivalent (has a charge of −3), $A^-$ represents a third of the anion group, and so on.

Inventive Ester Quats can be used alone or in mixtures, used in combination with other compounds or additives, or used as a formulation with other compounds or additives, depending on the intended use and the advantages and disadvantages attendant with each alternative application method. Some examples of compounds or additives that may be used in conjunction with Inventive Ester Quats or made into formulations with compounds of structural formula Inventive Ester Quats include surfactants or detergents, especially quaternary ammonium compounds, perfumes, preservatives, insect and moth repelling agents, polymeric soil release agents, antistatic agents, dyes and colorants, viscosity control agents, antioxidants, silicones, mineral oils and petrolatums, synthetic lubricants, defoaming agents, antifoaming agents, emulsifiers, brighteners, opacifiers, freeze-thaw control agents, shrinkage control agents, and mixtures thereof. Many examples of these additives are set forth in detail and are intended to demonstrate the scope of the invention. Other compounds or additives familiar to those of skill in the art and appropriate to a particular use, however, may also be used with or formulated with Inventive Ester Quats.

Inventive Ester Quats (either alone or in combination with other compounds) have many potential applications. For example, Inventive Ester Quats may be used as detailed herein, without limitation, as a fabric softener (either alone or in a combination detergent/fabric softener), as a car spray microemulsion, as a paper debonder, as a hair or skin conditioner, as a corrosion inhibitor, as an asphalt emulsifier, as an organoclay ingredient, or as an agricultural product emulsifier.

B. Applications

The present disclosure shows that Inventive Ester Quats may be used for many purposes and suitable additives may be incorporated therein based on the ultimate application. Such ingredients, for example, may contribute significantly to the ease of formulation, stability, dispersibility, fluidity, and the performance properties of the compositions.

Inventive Ester Quats have many advantages over the prior art compounds. For example, many of the compositions of the present invention can be produced as a liquid product that is 100% actives and contains no volatile organic compounds (VOCs) as solvents nor do they require low flash solvents for formulations. Such compositions and formulations according to the present invention are water soluble/dispersible, even cold water dispersible; readily formulate with other classes of quaternary amine softener/debonders; are low foaming; are virtually odor free; and are hydrolytically stable and color stable on storage. In addition, as shown below, the compositions of the present invention are extremely effective debonders as measured by tensile reduction and are very hydrophilic, affording very absorbent tissue and towels. Although the compositions of the present invention exhibit a wide range of tissue softening, they do impart softness and certain compounds exhibit effective softening, comparable to commercial softeners, such as AROSURF® PA-801 available from Witco Corporation. Furthermore, as there are two fatty ester functionalities in the compositions of the present invention, they exhibit improved biodegradability.

In one aspect, the present invention provides compounds and formulations that have the ability to impart to paper and paper products bulk enhancement, softness, lubricity, and antistatic properties, and improve ease of handling of the substrate and surface appearance; in the papermaking process, such compounds of the present invention are termed debonders. Debonders are usually added to the aqueous slurry of paper fibers in the head tank or headbox of a papermaking machine just prior to feeding the resulting slurry onto the papermaking or dewatering screen. These debonders condition the fibers to give improved softness feeling to the paper fibers that is valuable for their use in tissue and towelmaking. The compositions and formulations of the present invention can also be incorporated into the paper or tissue by any suitable means such as spraying or printing onto the surface of the paper or tissue. Given the surprisingly low viscosities of the Inventive Ester Quats alone or in many formulations, as mentioned above, spraying or topical application of the Inventive Ester Quats, even neat, is particularly suitable. If the Inventive Ester Quats are applied without the presence of water or other solvent, no evaporation need occur and the possibility of wrinkling is avoided.

Moreover, the present invention provides compounds and formulations that have the ability to impart to fabric (that is, articles of clothing, textiles, and so forth), properties including softness to the touch, ease of handling, increased lubricity, and a reduced tendency to carry or pick up static electricity. One form in which the compounds and formulations of the present invention are provided is as a liquid, for instance, as an emulsion or as a solution/suspension of the desired components. During use, an appropriate controlled amount of the liquid formulation is employed, for example, by pouring the formulation directly into the washing machine. Typically, the formulation is dispensed during the rinse cycle of the washing machine, either poured in by hand or metered in by an appropriate automatic metering device with which the washing machine is equipped.

The present invention also provides compounds and formulations that are useful in personal care products such as hair or skin conditioners. In this application, the present invention provides formulations that impart softness, lubricity, and improve the surface appearance of the skin or hair. The hair conditioners additionally reduce the tendency for tangling, improve the manageability, and impart a soft feel to the hair strands. Such hair conditioners are applied as dilute emulsions to the hair following its wash or may be incorporated into a combined conditioner and shampoo composition, also known as a conditioning shampoo, two-in-one shampoo, or two-in-one. Such hair and skin conditioning formulations typically incorporate effective amounts, for example, 0.1 wt. % to 10 wt. % or more, of emollients, humectants, and/or slip and conditioning agents, such as organopolysiloxanes and the like, to create formulations that are monophasic and can be made to be translucent or even clear. Compounds suitable for use as emollients, humectants and conditioners in formulations for skin care or hair care can be found in the CTFA Cosmetic Ingredient Dictionary, 3d Edition, and in the CTFA Cosmetic Ingredient Handbook, which are hereby incorporated by reference in their entireties.

Inventive Ester Quats are expected to be particularly useful in applications that take advantage of their ability to disperse hydrophobic material and to enhance the penetration and wetting exhibited by the compositions. Examples of such compositions and applications are set forth below, each revealing an additional aspect of the present invention.

The compounds and formulations of the present invention may be used as oil dispersants and oil slick dispersant formulations for application onto oil, for example, onto a film of oil, to disperse the oil.

The compounds and formulations of the present invention may also be used as oil well stimulation and oil recovery aids for injection into oil wells in order to penetrate into the surface of the borehole and assist liberation of crude oil from the matrix material into the borehole, from which it can be brought to the surface.

In addition, the compounds and formulations of the present invention may be used as vehicles for hydrophobic sheeting agents such as mineral oil and silicone oil. Such oils can readily be dispersed in compositions, according to the present invention, and the resulting formulations are highly satisfactory when sprayed or otherwise applied to a surface, such as a freshly washed automobile surface, to impart a lustrous, water-repellent film to the surface.

The compounds and formulations of the present invention may also be used as rinse aids, such as used in automatic dishwashers, wherein application of the composition of the present invention disperses residual hydrophobic matter, including cleaner residues and films.

Furthermore, the compounds and formulations of the present invention may be used as paper deinking and ink flotation agents for treating waste inked paper by addition to the pulp slurry such that the ink is liberated from the paper and prevented from redepositing onto the paper. In this application, the ink is typically dispersed or even fully solubilized in the resulting solution when the ink particles are floated from the fibers.

The compounds and formulations of the present invention may also be used as asphalt emulsion agents for emulsifying finely divided asphalt (at loadings of typically 1–20 wt. %), with or without particulate filler such as, in an aqueous phase, which comprises the composition according to the present invention.

Moreover, the compounds and formulations of the present invention may be used as corrosion inhibitor agents for application to any surface to which one desires to apply a film that protects against corrosion. The composition would typically contain an effective amount of a hydrophobic corrosion inhibiting material, such as liquid or waxy-solid fatty ester, paraffinic hydrocarbon, silicone, or the like, dispersed in a composition according to the present invention.

In addition, the compounds and formulations of the present invention may be used with ore flotation agents for separating ore from rock. Such floatation agents might include, for example, the agent available from Witco Corporation under the tradename WITCAMINE® AL42-12. Typically, the ore floatation agent (a collector or frother, depending on the characteristics of the particular separation desired in the floatation cell) or mixture thereof, which is a relatively hydrophobic material, is dispersed in a composition according to the invention and an effective amount is added (on a batch or continuous basis) to the ore separation cell. This permits the formulator to improve the dispersibility of the hydrophobic ore floatation agent, which often improves the performance of the mineral separation by improving the efficiency of the floatation agent's dispersibility. This can enable the operator to use smaller amounts of the ore floatation agent to achieve the desired purpose because there is a higher concentration of active ingredients available.

In addition, the compounds and formulations of the present invention may be used as suspension concentrates and emulsifiable concentrates of herbicides, pesticides, miticides, fungicides, or bactericides, wherein one or more liquid or solid, generally hydrophobic, active ingredients are dispersed in a composition according to the present invention. The resulting concentrate can be applied as a concentrate on or around desired vegetation, but is more often mixed with water (for example, at the point of use) to form a final dilute formulation having the desired concentration of active ingredient(s). This application takes advantage of the noteworthy property of this invention that addition of the water does not disrupt the monophasic state, nor the fluidity, of the formulation.

Furthermore, as noted above and explained in more detail below, organoclays or organophilic clays prepared from Inventive Ester Quats and clays, and the processes for making such organoclays are an aspect of the instant invention.

As noted above, the compositions and formulations of the present invention can also optionally contain other components, depending on the additional properties one may wish to provide in the finished composition. Such additional components include, but are not limited to, additional coupling agents and solvents, additional quaternary ammonium compounds, additional surfactants, hydrocarbon actives, perfumes, preservatives including bacteriocides and fungicides, insect and moth repelling agents, polymeric soil release agents, antistatic agents, dyes and colorants, viscosity control agents, antioxidants, silicones, defoaming agents, antifoaming agents, emulsifiers, brighteners, opacifiers, freeze-thaw control agents, shrinkage control agents, aloe, humectants, skin protectants, feel modifiers, and mixtures thereof. Examples of these additional components are set forth below, with the understanding that such additives or additional components mentioned herein are not exclusive to any particular application or use, but appropriate additives or additional components may be selected depending the application. Thus glycerin may be incorporated in the formulations of the instant invention to provide a hair conditioner or to provide a skin-conditioning lotion to be incorporated into a tissue to produce a tissue impregnated with the lotion.

C. Synthesis

Inventive Ester Quats can easily be synthesized from readily available starting materials using reaction procedures and conditions quite familiar to those of ordinary skill in this art. A preferred synthesis method is set forth below. As would be well-known in the art, other synthetic procedures or variations on the preferred synthetic procedure set forth below may be used that are more or less efficient or cost-effective than this proffered procedure. Such variations may include, without limitation, substitutions of reagents, starting materials, or catalysts; different amounts or concentrations of reactants, starting materials, or catalysts; different reaction conditions or duration of reactions; different analytical procedures or points at which a reaction is deemed complete; the isolation or purification of reaction products at any step; automation of the synthesis procedure; and substitution of different reaction(s) for one or more of the reactions set forth below. As one of skill in the art would appreciate, organic reactions generally do not produce stoichiometrically pure products and the actual product of an organic reaction is often a mixture of products. The reactions called for and the products specified therefore indicate the major or desired reaction or product.

In one embodiment, the synthesis begins with a primary fatty amine derived from a fatty acid and ammonia and hydrogen, such as a primary tallow amine, primary oleyl amine, primary canola amine (available from Witco Corporation under the ADOGEN® tradename) or a fatty diamine from reaction of a fatty amine and acrylonitrile followed by reduction with hydrogen.

In the first step, this fatty amine compound is alkoxylated using an alkoxylating agent, which may be ethylene oxide (EO), propylene oxide (PO), or butylene oxide (BO), or (less preferred) a mixture thereof, depending on the desired choice of alkyl groups to become attached to the respective nitrogen atoms. In a preferred procedure used to synthesize the examples presented herein, the initial alkoxylation step is performed at 160–165° C. with no catalyst, after an induction period of about 30 minutes, the reaction starts when all calculated alkoxylating agent needed to react with the protons on the nitrogen groups is added. The reaction is allowed to proceed for 30 minutes and is then analyzed; if the tertiary amine is between 92 wt. % and 97 wt. %, the reaction is deemed complete and 0.1% solids, based upon the sum of final charges, of KOH as a 45% aqueous solution is added to the mixture. The mixture is then dehydrated to remove water, generally to a level of about 200 ppm water. Additional alkoxylating agent is added to achieve the desired molecular weight and the products is tested using the standard "neutralization equivalents" titration method.

In the next step, the alkoxylated product is esterified by reaction of fatty acids with the respective hydroxyl groups resulting from the alkoxylation (where $R^4$ is C15–C17, this product has been assigned CAS Registry Number 217813-05-3). The esterification is carried out with carboxylic acids of structural formula $R^4C(O)OH$, wherein $R^4$ is a linear, branched, or cyclic alkyl or alkylene group containing 11 to 21 carbon atoms. While the esterification can be carried out with an appropriate quantity of one such carboxylic acid, it is preferred for reasons of economy, product performance, and convenience to employ mixtures of carboxylic acids each corresponding to structural formula $R^4C(O)OH$. For instance, mixtures of such fatty acids from various animal and vegetable origins are conveniently commercially available. One example of such material is tallow fatty acids which, as is generally known in this field, is a mixture of fatty acids predominantly composed of fatty acids containing 14, 16, and 18 carbon atoms, and 0 and 1 degrees of unsaturation. Other preferred sources include coconut fatty acids and canola fatty acids, although any suitable fatty acid may be used. Esterification is carried out under conventional conditions, well-known to the chemist in this field, allowing for the withdrawal of by-product water. The number of moles of fatty acid is selected to provide the desired average degree of esterification in the mixture of products formed upon esterification. In a preferred procedure used to synthesize the examples presented herein, the desired amount of fatty acid is added to the alkoxylated ester of the previous step and hypophosphorous acid (HPPA) is added as a catalyst. Preferably, the HPPA is used at a dosage of 0.025 wt. % based on the fatty acid charge; at this dosage, the HPPA also has a bleaching effect on the product. The amount of HPPA used, however, may be adjusted upward or downward and may be eliminated entirely. The reaction mixture is heated to 200° C. and a nitrogen sparge is employed to remove the by-product water of reaction. The reaction is monitored for 8–15 hours using a standard "acid value" titration method. When an acid value of 10 is reached, preferably 5 or less, the reaction is deemed complete.

Next, if desired, the esterified product or mixture of esterified products is quaternized and/or protonated. As recognized hereinabove, the esterified product can be completely quaternized, but it is preferred to carry out partial quaternization only, if any. Quaternization is carried out under conditions well known in this field for quaternization of amines, by reaction of the esterified amine with a suitable quaternizing agent. Preferably, only one particular quaternizing agent is employed, in which case all of the quaternizing substituents will be the same. Preferred quaternizing agents include methyl chloride, dimethyl sulfate (DMS), and diethyl sulfate (DES). The DMS derivative has been assigned CAS Registry Number 217813-30-4. In a preferred procedure used to synthesize the examples presented herein, the reaction mixture from the previous step was cooled to 60–70° C. and the quaternizing agent was added when the reaction mixture was less than 70° C. until the wt.% of free amine was less than or equal to 3.0.

Protonation, if desired, can be carried out by reacting the esterified product or mixture of products with an acid of the formula HA, such as strong acids, such as sulfuric acid, phosphoric acid, or hydrochloric acid, or other acids, such as acetic acid. The acetic acid derivative has been assigned CAS Registry Number 217813-07-5. Optional steps include a bleaching step using bleaching agents well-known in this field.

Each of the foregoing reactions can be carried out in solvent or in solvent-free conditions, in each case employing conditions well established for the respective reactions in this field.

In another embodiment, the Inventive Ester Quats are prepared in a similar manner except that a primary amine containing a $C_1$ to $C_7$ hydrocarbyl group is employed and the caboxylic acid may comprise a compound wherein $R^4$ is a $C_3$ to $C_{10}$ hydrocarbyl group.

As can be seen, Inventive Ester Quats can readily be synthesized from readily available starting materials using individual reaction procedures and conditions quite familiar to those of ordinary skill in this art.

Examples of particular synthetic procedures would be as follows.

EXAMPLE A

A primary tallow amine, ADOGEN® 170, was reacted with 10 moles of ethylene oxide per mole of ADOGEN®

170 to produce VARONIC® T-210. The VARONIC® T-210 was then esterified with a mixture of $C_{14}$–$C_{18}$ fatty acids, 1.8 moles of fatty acid per mole of ethoxylate, following which the amine ethoxylate ester was quaternized with one mole of DMS. In one example, Example A-1, the fatty acids were a commercial mixture of tallow fatty acids, DISTAL 51. In another example, Example A-2, the fatty acids were obtained from canola oil. Both products were clear liquids at 100% actives.

EXAMPLE B

A primary cocoamine, ADOGEN® 160, was reacted with 15 moles of ethylene oxide per mole of ADOGEN® 160 to produce VARONIC® K-215. The VARONIC® K-215 was then esterified with a mixture of $C_{14}$–$C_{18}$ fatty acids, 1.8, moles of fatty acid per mole of ethoxylate, following which the amine ethoxylate was quaternized with one mole of DMS. In one example, Example 2-A, the fatty acids were a commercial mixture of tallow fatty acids, DISTAL 51. In another example, Example 2-B, the fatty acids were obtained from canola oil. Both products were clear liquids at 100% actives.

EXAMPLE C

A primary canola amine was reacted with 6 moles of ethylene oxide per mole of amine to produce the ethoxylated amine. The ethoxylated amine was then esterified with a mixture of $C_{14}$–$C_{18}$ canola acids, 1 mole of acid per mole of ethoxylate. The product could be used as is, could be converted into an ammonium salt by reaction with HCl or acetic acid, or reacted with DMS to form a quaternary ammonium salt.

EXAMPLE D

A fatty diamine, ADOGEN® 570, was reacted with 10 moles of ethylene oxide per mole of ADOGEN® 570 to produce VARONIC® T-410. The VARONIC® T-410 was then esterified with a mixture of $C_{14}$–$C_{18}$ fatty acids. In Example D-1, the fatty acids were a commercial mixture of tallow fatty acids, and the mole ratio of the fatty acids to tallow diamine ethoxylate was 1.5 to 1. The ester of the tallow amine ethoxylate was quaternized with 1.2 moles of DMS. In Example D-2, the fatty acids were obtained from canola oil, and the mole ratio of the fatty acids to tallow diamine ethoxylates was 2/1. The ester of the tallow amine ethoxylate was quaternized with 2 moles of DMS.

Many Inventive Ester Quats have been synthesized and tested in various applications and formulations and the results set forth below. In order to identify such Inventive Ester Quats and certain other commercial compounds and formulations discussed herein, a unique designation has been applied to each, as set forth as a legend in Table 1, which serves to identify the compound being discussed, whether the Inventive Ester Quat 5455-111, or a commercial product, such as that sold by Witco Corporation under the tradename VARISOFT® 3690.

TABLE 1

Detailed Description of Inventive Ester Quats and Debonders Tested

| Designation | Description |
|---|---|
| VARISOFT® 3690 | 1-methyl-2-noroleyl-3-oleyl amidoethyl imidazolinium methosulfate, available from Witco Corporation under the tradename VARISOFT® 3690 |
| BEROCELL 509® HA | Proprietary softener/debonder formulation, available from Eka Nobel under the tradename BEROCELL 509<® HA |
| AROSURF® 8-190 | PEG ester of unsaturated fatty acid, available from Witco Corporation under the tradename AROSURF® 8-190 |
| AROSURF® PA-801 | Proprietary cationic softener/debonder blend, available from Witco Corporation under the tradename AROSURF® PA-801 |
| ADOGEN® 66 | Ethyl bis(polyethoxyl ethanol) tallow ammonium ethosulfate, available from Witco Corporation under the tradename ADOGEN® 66 |
| REWOQUAT® CPEM | cocopentaethoxymethylammonium methosulfate |
| WITCONOL® APM | PPG-3 myristyl ether |
| REWOQUAT® 525 | 1-methyl-2-norpalmalkyl-3-palm fatty acid-amidoethylimidazolinium methosulfate |
| TMPD (1 EO) | 2,2,4-trimethylpentane-1,3-pentanediol with 1 mole of EO |
| TMPD (5 EO) | 2,2,4-trimethylpentane-1,3-pentanediol with 5 moles of EO |
| VT-2085 | primary tallow amine + 8.5 moles EO |
| VARONIC® K-215 | primary cocoamine + 15 moles EO, available from Witco Corporation under the tradename VARONIC® K-215 |
| VARONIC® T-202 | primary tallow amine + 2 moles EO, available from Witco Corporation under the tradename VARONIC® T-202 |
| VARONIC® T-210 | primary tallow amine + 10 moles EO, available from Witco Corporation under the tradename VARONIC® T-210 |
| VARONIC® T-215 | primary tallow amine + 15 moles EO, available from Witco Corporation under the tradename VARONIC® T-215 |
| VARONIC® T-216 | primary tallow amine + 16 moles EO, available from Witco Corporation under the tradename VARONIC® T-216 |
| VARONIC® T-410 | tallow diamine + 10 moles EO, available from Witco Corporation under the tradename VARONIC® T-410 |
| 5326-198C | 80 wt. % 5455-64; 15 wt. % AROSURF® 8-190; 5 wt. % propylene glycol |
| 5326-199A | 80 wt. % 5455-111; 15 wt. % AROSURF® 8-190; 5 wt. % propylene glycol |
| 5326-199A1 | 80 wt. % 5455-111A; 15 wt. % AROSURF® 8-190; 5 wt. % propylene glycol |
| 5326-199B | 80 wt. % 5455-112; 15 wt. % AROSURF® 8-190; 5 wt. % propylene glycol |
| 5326-199D | 80 wt. % 5398-53; 15 wt. % AROSURF® 8-190; 5 wt. % propylene glycol |
| 5385-152A | 80 wt. % VARISOFT® 3690; 20 wt. % 5398-1 |

TABLE 1-continued

Detailed Description of Inventive Ester Quats and Debonders Tested

| Designation | Description |
|---|---|
| 5385-152B | 50 wt. % VARISOFT ® 3690; 50 wt. % 5398-1 |
| 5385-152C | 80 wt. % VARISOFT ® 3690; 15 wt. % 5398-1; 5 wt. % propylene glycol |
| 5385-153A | 72.5 wt. % 5455-119; 20.0 wt. % 5398-1; 7.5 wt. % hexylene glycol |
| 5385-153B | 47.6 wt. % 5455-119; 47.6 wt. % 5398-1; 4.8% hexylene glycol |
| 5397-106A | VARONIC ® T410 + 1.5 moles tallow fatty acid + 1.2 moles DMS |
| 5398-100 | VT-2085 + 1.5 moles tallow fatty acid + 1 mole DMS |
| 5398-1 | VARONIC ® T-215 + 1 mole tallow fatty acid + 1 mole DMS |
| 5398-5/53 | VARONIC ® T-215 + 1.8 moles tallow fatty acid + 1 mole DMS |
| 5398-7 | VARONIC ® T-215 + 1 mole DMS |
| 5398-21 | VARONIC ® T-210 + 1 mole tallow fatty acid + 1 mole DMS |
| 5398-59 | Hexamethylenediamine (HMDA) + 4 moles EO + 3 moles canola fatty acid + 1.5 moles DMS |
| 5398-107/127 | VARONIC ® T-215 + 1.8 moles canola fatty acid + 1 mole DMS |
| 5398-119 | VARONIC ® T-210 + 1.8 moles tallow fatty acid + 1 mole DMS |
| 5398-120 | VARONIC ® K-215 + 1.8 moles tallow fatty acid + 1 mole DMS |
| 5398-121 | VARONIC ® K-215 + 1 mole canola fatty acid + 1 mole DMS |
| 5398-122/129 | VARONIC ® T-216 + 1.8 moles tallow fatty acid + 1 mole DMS |
| 5398-128 | VARONIC ® T-215 + 1.8 moles behenic fatty acid + 1 mole DMS |
| 5398-153C | 75 wt. % 5455-119; 20 wt. % 5398-1; 5 wt. % propylene glycol |
| 5455-63 | VARONIC ® T-210 + 2 moles canola fatty acid |
| 5455-63A | VARONIC ® T-210 + 2 moles canola fatty acid + 1 mole HCl |
| 5455-64 | VARONIC ® T-210 + 2 moles canola fatty acid + 1 mole DMS |
| 5455-80 | VARONIC ® T-202 + 2 moles canola fatty acid + 1 mole DMS |
| 5455-82 | VARONIC ® T-410 + 2 moles tallow fatty acid + 2 moles DMS |
| 5455-111 | canola amine + 6 EO + 1 mole canola fatty acid |
| 5455-111A | canola amine + 6 EO + 1 mole canola fatty acid + 1 mole HCl |
| 5455-112 | canola amine + 6 EO + 1 mole canola fatty acid + 1 mole DMS |
| 5455-119 | Hexamethylenediamine (HMDA) + 6 moles EO + 1.5 moles canola fatty acid + 1.5 moles tallow fatty acid + 1.75 moles DMS |
| 5455-120 | Hexamethylenediamine (HMDA) + 10 moles EO + 1.5 moles canola fatty acid + 1.5 moles tallow fatty acid + 1.75 moles DMS |
| 5455-158 | canola amine + 6 EO + 1.5 moles canola fatty acid |
| 5455-158A | canola amine + 6 EO + 1.5 moles canola fatty acid + 1 mole HCl |
| 5455-159 | canola amine + 6 EO + 1.5 moles canola fatty acid + 1 mole DMS |
| 5455-172 | canola amine + 6 EO + 1 mole erucic acid + 1 mole DMS |
| 5455-175 | primary tallow amine + 2 PO + 10 EO + 2 moles canola fatty acid |
| 5455-176 | primary tallow amine + 2 PO + 10 EO + 2 moles canola fatty acid + 1 mole DMS |
| BLEND 1 | 80 wt. % 5398-5; 5 wt. % REWOQUAT ® CPEM; 10 wt. % AROSURF ® 8-190; 5 wt. % propylene glycol |
| BLEND 22 | 45 wt. % 5398-59; 25 wt. % 5455-64; 20 wt. % TMPD (5 EO), 5 wt. % WITCONOL ® APM; 5 wt. % water |
| BLEND 25 | 50 wt. % 5398-119; 20 wt. % 5455-120; 15 wt. % AROSURF ® 8-190; 5 wt. % propylene glycol |
| BLEND 32 | 45 wt. % 5455-120; 30 wt. % VARISOFT ® 3690; 20 wt. % TMPD (1 EO); 5 wt. % propylene glycol |
| BLEND 34 | 50 wt. % 5398-121; 30 wt. % REWOQUAT ® W575; 10 wt. % TMPD (1 EO); 10 wt. % WITCONOL ® APM |

Preferred Inventive Ester Quats include 5455-63 (VARONIC® T-210+2 moles canola fatty acid), 5455-158 (canola amine+6 EO+1.5 canola fatty acid), most preferably, 545564 (VARONIC® T-210+2 moles canola fatty acid+1 mole DMS), 5455-112 (canola amine+6 EO+1 mole canola fatty acid+1 mole DMS), 5455-159 (canola amine+6 EO+1.5 moles canola fatty acid+1 mole DMS), 5398-5/5398-53 (VARONIC® T-215+1.8 moles tallow fatty acid+1 mole DMS), which can be made according to the above synthesis methods.

D. Formulations and Properties

The Inventive Ester Quats as described herein exhibit a number of desirable properties making the Inventive Ester Quats particularly suitable for formulation into commercial products such as paper debonders, fabric softeners and other commercial products, as mentioned above.

Most notably, the Inventive Ester Quats can readily be formulated into useful compositions such as aqueous compositions, which achieve the desired functionality and which are clear, that is, transparent or translucent. This property can be realized at a variety of concentrations of active ingredient, with or even without special solvents or coupling agents. In some cases, the Inventive Ester Quats are colored after synthesis, but they can be bleached using techniques and methods known to those of skill in the art. The Inventive Ester Quats, however, are very color stable on storage, as shown in Table I. It should be noted that these Inventive Ester Quat preparations were not color bleached before testing, which is contemplated for certain applications.

TABLE I

COLOR STABILITY

| Storage Time at | Quaternary Compound (Gardner units) | | | | |
|---|---|---|---|---|---|
| 40° C. (weeks) | 5398-53 | 5398-21 | 5397-100 | 5398-5 | 5398-1 |
| 0 | 9.7 | 8.3 | 8.8 | 7.1 | 4.0 |
| 1 | 9.8 | 8.5 | 9.7 | 6.9 | 4.1 |
| 4 | 9.8 | 8.6 | 10.1 | 6.9 | 4.6 |
| 8 | 10.0 | 8.7 | 10.1 | 6.7 | 4.4 |
| 12 | 10.0 | 10.0 | 10.2 | 6.6 | 4.5 |

The Inventive Ester Quats are also very hydrolytically stable on storage, as shown in Table II. The Inventive Ester Quats were prepared as 5 wt. % solutions in 50% isopropyl alcohol/50% water; the color stability and absence of pH drift showed that the Inventive Ester Quats are generally quite hydrolytically stable.

TABLE II

HYDROLYTIC STABILITY

| Storage Time at | Quaternary Compound (pH) | | | | |
|---|---|---|---|---|---|
| 40° C. (weeks) | 5398-53 | 5398-21 | 5397-100 | 5398-5 | 5398-1 |
| 0 | 2.8 | 5.3 | 5.2 | 3.1 | 5.1 |
| 1 | 2.7 | 5.5 | 5.2 | 3.3 | 5.3 |
| 4 | 2.8 | 5.6 | 5.3 | 3.2 | 5.0 |
| 8 | 2.7 | 5.4 | 5.5 | 3.2 | 4.7 |
| 12 | 2.8 | 5.5 | 5.5 | 3.2 | 4.3 |

Other properties are realized as well. For instance, as noted above, the products are ultimately biodegradable. Surprisingly, the embodiments which have no substituents, or wherein the only substituents are —H, exhibit satisfactory biodegradability. Also, the Inventive Ester Quats exhibit advantageous stability, solubility, and freedom from excessively objectionable color, odor, and foam. Furthermore, the Inventive Ester Quats alone or in many formulations often exhibit surprisingly low viscosities compared to conventional amine or quaternary ammonium compounds, making the Inventive Ester Quats particularly suitable for certain methods of application or use, for example, spraying or topical application of the Inventive Ester Quats.

Although the Inventive Ester Quats have many potential uses, in particular, they exhibit highly satisfactory fabric softening capabilities. Thus, the Inventive Ester Quats, as well as mixtures of such compounds, can be advantageously formulated appropriately into products useable as fabric softeners. It has been found that, regardless of the other components that may be present in the fabric softener formulation, the pH of the formulation as a whole should be below 5, and preferably 2.5 to 4.0, in order to maintain low susceptibility of the ester functionality to hydrolysis in water. The preferred method for providing or adjusting the desired pH value is adding small amounts of an acid, such as hydrochloric acid, sulfuric acid, or acetic acid, consistent with appropriate adjustment of the average degree of esterification and average degree of quaternization to the Inventive Ester Quats. Preferred emulsions useful as fabric softener compositions can contain about 2 wt. % to about 80 wt. %, preferably 5 wt. % to 30 wt. %, and more preferably 6 wt. % to 25 wt. %, of one or more Inventive Ester Quats. In general, higher solids contents can be provided more easily with lower degrees of quaternization.

The Inventive Ester Quats can be formulated into compositions that may include water and one or more of the solvents which are conventionally used, including ethanol, isopropanol, hexylene glycol, propylene glycol, diethylene glycol, or similar solvent of mixture thereof, as a concentrate or more dilute form, depending on the application. Selection of a suitable solvent for a particular application is well-known to those of skill in the art. However, as the majority of the Inventive Ester Quats are liquids at 100% actives, solvents are not required for formulations using these Inventive Ester Quats. This aspect of the present invention advantageously avoids the use of solvents which have low flash points, which contribute to VOC loads and which contribute to BOD load.

E. Additional Quaternary Ammonium Compounds

Additional conventional quaternary ammonium compounds or salts may be present with the compound or Inventive Ester Quats in accordance with the present invention. The compounds presented below are only examples of conventional quaternary compounds that are suitable for use in the formulations of the present invention. As with the Inventive Ester Quats, these conventional quaternary ammonium compounds (quats or salts) may have an anion to provide electrical neutrality and, in general, such anion may be any anion which is not deleterious to the properties of the overall compound. Thus, in the structural formulas (i) to (xxiv) below, the counteranion, whether designated as $A^-$ or not shown but understood, may be selected, without limitation, from the group consisting of fluoride, chloride, bromide, iodide, chlorite, chlorate, hydroxide, hypophosphite, phosphite, phosphate, carbonate, formate, acetate, citrate, lactate, and other carboxylates, oxalate, methyl sulfate, ethyl sulfate, benzoate, and salicylate, and the like. Preferred examples of the anions are chloride, bromide, methyl sulfate, ethyl sulfate, acetate, citrate, and salicylate. If the anion is monovalent (has a charge of −1), $A^-$ represents the anion group, if the anion is divalent (has a charge of −2), $A^-$ represents half of the anion group, if the anion is trivalent (has a charge of −3), $A^-$ represents a third of the anion group, and so on.

In general, the amounts of Inventive Ester Quats and conventional quaternary compounds in a formulation can vary from 100% Inventive Ester Quat (i.e., neat) to less than about 1% Inventive Ester Quat and remainder conventional quaternary compounds or a mixture of conventional quaternary compounds and other surfactants, solvents, and additives. The amount of conventional quaternary ammonium compound is therefore any effective amount for the purpose. In general, the amount of Inventive Ester Quat will be substantial in any formulation, particularly with respect to the total amount of quaternary ammonium compounds, which is the sum of the Inventive Ester Quats and the conventional quaternary ammonium compounds, in the composition. In general, it is contemplated that Inventive Ester Quats may be formulated with conventional quaternary ammonium compounds, alone or in combination with other additives set forth herein, such that the Inventive Ester Quats comprise from about 10% to about 99% by weight, preferably from about 15% to about 95% by weight, more preferably from about 30% to about 90% by weight, even more preferably from about 50% to about 90% by weight, and most preferably from about 75% to about 90% by weight, of the total amount of quaternary ammonium compounds in the composition.

The conventional quats that may be formulated with the Inventive Ester Quats in accordance with the present invention include, but are not limited to, nitrogenous compounds selected from the group consisting of quaternized or acid salt derivatives of:

(i) alkylene diamines, diamides, and amidoamines, including compounds of the formula:

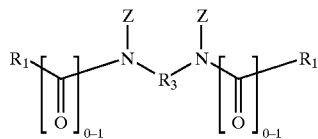

wherein each $R_1$ is a $C_{12}-C_{21}$ alkyl or alkylene group, each Z is m $-(R_2O)_{0-4}H$, or $-R_2H$, and $R_2$ and $R_3$ are divalent $C_1-C_6$ alkylene groups;

(ii) substituted imidazoline compounds having the formula:

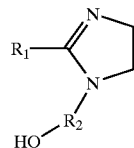

(iii) reaction products of higher fatty acids with alkylenetriamines in, for example, a molecular ratio of about 2:1, the reaction products containing compounds of the formula:

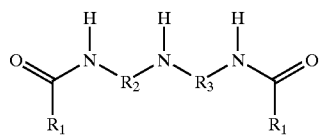

wherein $R_1$, $R_2$ and $R_3$ are defined as above; and
(iv) substituted imidazoline compounds having the formula:

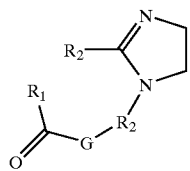

wherein G is $-O-$ or $-NH-$ and $R_1$ and $R_2$ are defined as above; and mixtures thereof.

Preferred examples of compounds of structural formula (i) are those derived from hydrogenated tallow fatty acids and the hydroxyalkylalkylenediamine is N-2-hydroxyethylethylenediamine, such that $R_1$ is a $C_{15}-C_{21}$ aliphatic group, and $R_2$ and $R_3$ are divalent ethylene groups.

Preferred examples of compounds of structural formula (iii) are stearic hydroxyethyl imidazoline, wherein $R_1$ is a $C_{21}$ aliphatic group and $R_2$ is a divalent ethylene group, and N,N"-ditallowalkanoyldiethylenetriamine, where $R_1$ is a $C_{15}-C_{21}$ aliphatic group and $R_2$ and $R_3$ are divalent ethylene groups. A preferred example of a compound of structural formula (iv) is 1-tallowamidoethyl-2-tallowimidazolin wherein $R_1$ is a $C_{15}-C_2$, aliphatic group and $R_2$ is a divalent ethylene group.

Both N,N'-ditallowalkanoyldiethylenetriamine and 1-tallowethylamido-2-tallowimidazolin are reaction products of tallow fatty acids and diethylenetriamine, and are precursors of the cationic fabric softening agent methyl-1-tallowamidoethyl-2-tallowimidazolinium methylsulfate (see "Cationic Surface Active Agents as Fabric Softeners," R. R. Egan, *Journal of the American Oil & Chemicals Society*, January 1978, pages 118–121). N,N"-ditallowalkanoyldiethylenetriamine and 1-tallowamidoethyl-2-tallowimidazoline can be obtained from Witco Corporation. Methyl-1-tallowamidoethyl-2-tallowimidazolinium methylsulfate is available from Witco Corporation under the tradename VARISOFT® 475.

Other suitable quats are those containing one $C_{18}-C_{22}$ aliphatic group, particularly those selected from the group consisting of:
(v) acyclic quaternary ammonium salts having the formula:

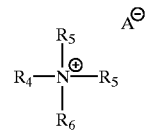

wherein $R^4$ is a $C_8-C_{22}$ aliphatic group, benzyl or $(C_4-C_{18}$ alkyl$)$-$OCH_2CH_2)_{2-3}-$, $R_5$ and $R_6$ are $C_1-C_4$ alkyl or hydroxyalkyl groups, and $A^-$ is an anion as defined above;
(vi) substituted imidazolinium salts having the formula:

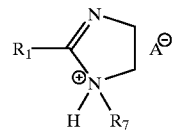

wherein $R_1$ is a $C_{12}-C_{21}$ alkyl or alkylene group, $R_7$ is hydrogen or a $C_1-C_4$ alkyl or hydroxyalkyl group, and $A^-$ is an anion as defined above;
(vii) substituted imidazolinium salts having the formula:

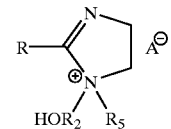

wherein $R_1$, $R_2$, $R_5$, and $A^-$ are as defined above;
(viii) alkylpyridinium salts having the formula:

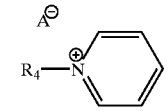

wherein $R^4$ is a $C_8-C_{22}$ aliphatic group and $A^-$ is an anion as defined above; and
(ix) alkanamide alkylene pyridinium salts having, the formula:

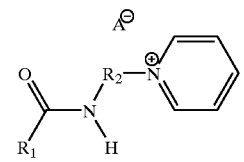

wherein $R_1$ is a $C_{12}-C_{21}$ aliphatic group, $R_2$ is a divalent $C_1-C_6$ alkylene group, and $A^-$ is an anion as defined above; and mixtures thereof.

Examples of compounds of structural formula (v) are the monoalkyltrimethylammonium salts such as monotallowtrimethylammonium chloride, mono(hydrogenated tallow)-trimethylammonium chloride, palmityltrimethylammonium chloride and soyatrimethylammonium chloride, available from Witco Corporation under the tradenames ADOGEN® 471, ADOGEN® 441, ADOGEN® 444, and ADOGEN® 415, respectively. In these compounds, $R_4$ is a $C_{16}$–$C_{18}$ aliphatic group, and $R_5$ and $R_6$ are methyl groups. Other examples of compounds of structural formula (v) are behenyltrimethylammonium chloride, wherein $R_4$ is a $C_{22}$ aliphatic group, which is available from Witco Corporation under the tradename KEMAMINE® Q2803-C; soyadimethylethylammonium ethylsulfate, wherein $R^4$ is a $C_{16}$–$C_{18}$ aliphatic group, $R_5$ is a methyl group, $R_6$ is an ethyl group, and $A^-$ is an ethylsulfate anion; and methyl bis(2-hydroxyethyl)octadecylammonium chloride wherein $R_4$ is a $C_{18}$ aliphatic group, $R_5$ is a 2-hydroxyethyl group and $R_6$ is a methyl group.

An example of a compound of structural formula (vii) is 1-ethyl-1-(2-hydroxyethyl)-2-isoheptadecylimidazolinium ethylsulfate, wherein $R_1$ is a $C_{17}$ aliphatic group, $R_2$ is an ethylene group, $R_5$ is an ethyl group, and $A^-$ is an ethylsulfate anion.

Other quats useful in the present invention include cationic nitrogenous salts having two or more $C_8$–$C_{22}$ aliphatic groups or one $C_8$–$C_{22}$ aliphatic group and an arylalkyl group. Examples include:

acyclic quaternary ammonium salts having the formula:

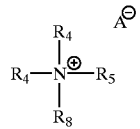

wherein each $R^4$ is a $C_8$–$C_{22}$ aliphatic group, $R_5$ is a $C_1$–$C_4$ alkyl or hydroxyalkyl group, $R_8$ is selected from the group consisting of $R_4$ and $R_5$ groups, and $A^-$ is an anion as defined above;

(xi) diamido quaternary ammonium salts having the formula:

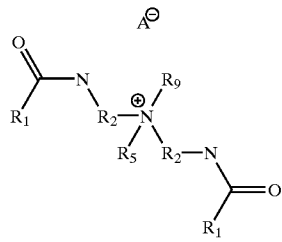

wherein each $R_1$ is a $C_{12}$–$C_{21}$ alkyl or alkylene group, each $R_2$ is a divalent alkylene group having 1 to 3 carbon atoms, $R_5$ and $R_9$ are $C_1$–$C_4$ saturated alkyl or hydroxyalkyl groups, and $A^-$ is an anion as defined above;

(xii) alkoxylated diamido quaternary ammonium salts having the formula:

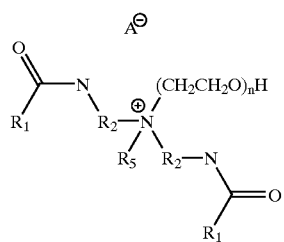

wherein n is equal to 1 to about 5, and $R_1$, $R_2$, $R_5$, and $A^-$ are as defined above;

(xiii) quaternary ammonium compounds having the formula:

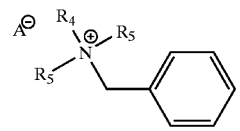

wherein $R^4$ is a $C_8$–$C_{22}$ aliphatic group, each $R_5$ is a $C_1$–$C_4$ alkyl or hydroxyalkyl group, and $A^-$ is an anion as defined above;

(xiv) amide-substituted imidazolinium salts having the formula:

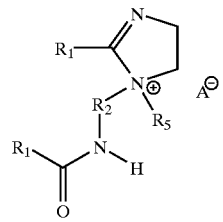

wherein each $R_1$ is a $C_{12}$–$C_{21}$ aliphatic group, $R_2$ is a divalent alkylene group having 1 to 3 carbon atoms, and $R_5$ and $A^-$ are as defined above, or $R_5$ is —H; and (xv) ester-substituted imidazolinium salts having the formula:

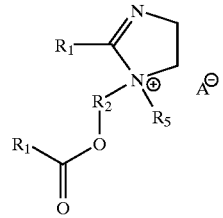

wherein $R_1$, $R_2$, $R_5$, and $A^-$ are as defined above; and mixtures thereof.

Examples of compounds of structural formula (x) are the well-known dialkyldimethylammonium salts such as ditallowdimethylammonium chloride, ditallowdimethylammonium methylsulfate, di(hydrogenated tallow) dimethylammonium chloride, distearyldimethylammonium chloride, dibehenyldimethylammonium chloride. Di(hydrogenated tallow)dimethylammonium chloride and ditallowdimethylammonium chloride are preferred. Examples of commercially available dialkyldimethylammonium salts usable in the present invention are di(hydrogenated tallow)dimethylammonium chloride (available from Witco Corporation under the tradename ADOGEN® 442); ditallowdimethylammonium chloride (available from Witco Corporation under the tradename ADOGEN® 470); distearyldimethylammonium chloride (available from Witco Corporation under the tradename AROSURF® TA-100); dicocodimethyl ammonium chloride (available from Witco Corporation under the tradename ADOGEN® 462), and dibehenyldimethylammonium chloride,h wherein $R_4$ is an acyclic aliphatic $C_{22}$ aliphatic group (available from Witco Corporation under the tradename KEMAMINE® Q-2802C).

Examples of compounds of structural formula (xi) are methylbis(tallowamidoethyl)(2-hydroxyethyl)ammonium methylsulfate and methylbis(hydrogenated tallowamidoethyl)(2-hydroxyethyl)ammonium methylsulfate, wherein $R_1$ is a $C_{15}$–$C_{17}$ aliphatic group, $R_2$ is an ethylene group, $R_5$ is a methyl group, $R_9$ is a hydroxyalkyl group, and $A^-$ is a methylsulfate anion; both of these materials are available from Witco Corporation under the tradenames VARISOFT® 222 and VARISOFT® 110, respectively.

An example of a compound of structural formula (xiii) is dimethylstearylbenzylammonium chloride, wherein $R_4$ is a $C_{18}$ aliphatic group, $R_5$ is a methyl group and $A^-$ is chloride, which is available from Witco Corporation under the tradename VARISOFT® SDC.

Examples of compounds of structural formula (xiv) are 1-methyl-1-tallowamidoethyl-2-tallowimidazolinium methylsulfate and 1-methyl-1-(hydrogenated tallowamidoethyl)-2-(hydrogenated tallow)imidazolinium methylsulfate wherein $R_1$ is a $C_{15}$–$C_{17}$ aliphatic group, $R_2$ is an ethylene group, $R_5$ is a methyl group, and $A^-$ is a chloride anion; available from Witco Corporation under the tradenames VARISOFT® 475 and VARISOFT® 445, respectively.

Additional examples of quaternary ammonium compounds useful in the present invention include:
(xvi) compounds having the formula:

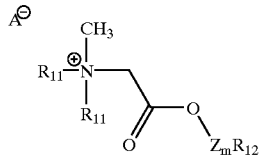

wherein $R_{11}$ is selected from the group consisting of: (a) —$CH_3$, —$CH_2CH_3$, —$CH_2CH_2OH$, or $C_{12}$–$C_{24}$ linear aliphatic groups, (b) ether groups, each of which has the structure: $R_{13}O(CH_2O)_y$—, (c) amide groups, each of which has the structure:

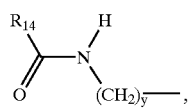

and (d) ester groups, each of which has the structure:

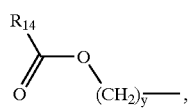

wherein $R_{12}$ is a $C_8$–$C_{32}$ linear aliphatic group, $R_{13}$ is a $C_8$–$C_2$, linear aliphatic group, $R_4$ is a $C_7$–$C_{17}$ linear aliphatic group, Z is an alkoxy group containing one oxygen atom and either two or three carbon atoms, $A^-$ is an anion as defined above, m is an integer from 1 through 12, and y is an integer which is either 2 or 3.

Yet additional examples of fabric softening compounds useful in the present invention include:
(xvii) compounds having the formula:

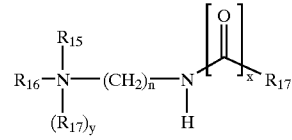

wherein $R_{15}$ is hydrogen or a $C_1$–$C_4$ alkyl group, each $R_{16}$ is a $C_1$–$C_4$ alkyl group or

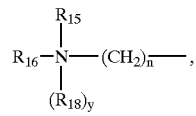

each $R_{17}$ is a $C_8$–$C_{28}$ alkyl or alkenyl group, $R_{18}$ is hydrogen or a $C_1$–$C_4$ alkyl group, each y is 0 or 1, x is 0 or 1, and each n is from 1 to 6;

(xviii) amides represented by the structural formula:

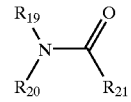

wherein $R_{19}$ and $R_{20}$ are selected independently from the group consisting of $C_1$–$C_{22}$ aralkyl or alkaryl groups, $R_{21}$ is hydrogen, a $C_1$–$C_{22}$ aralkyl or alkaryl group, or is O—$R_{22}$, wherein $R_{22}$ is a $C_1$–$C_{22}$ aralkyl or alkaryl group, and $R_{21}$ and $R_{22}$ optionally contain 1 to 10 alkylene oxide units or functional groups selected from hydroxy, amine, amide, ester, and ether groups; the aryl groups being possibly derived from heterocyclic compounds; at least one of the $R_{19}$ and $R_{20}$ groups contains 10 or more carbon atoms; and where the sum of carbon atoms in $R_{19}$+$R_{20}$+$R_{21}$ is equal to or greater than 14. Preferably, the sum of carbon atoms in $R_{19}$+$R_{20}$ is equal to or greater than 16.

Examples of compounds of structural formula (xviii) include N,N-ditallow acetamide, N,N-dicoconut acetamide, N,N-dioctadecyl propanamide, N-dodecyl-N-octadecyl acetamide, N-hexadecyl-N-dodecyl butanamide, N,N-ditallow benzamide, N,N-dicoconut benzamide, and N,N-ditallow 2-phenyl acetamide.

Additional fabric softening compounds useful in the present invention include all ester quaternaries, including but not limited to:
(xix) compounds of the following structural formulas:

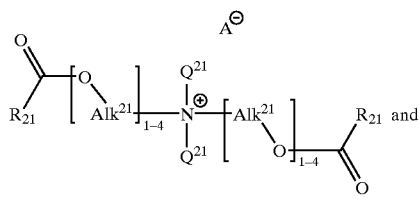

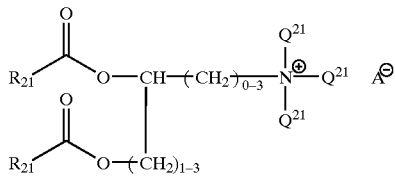

wherein each $R_{21}$ is independently a $C_{12}$–$C_{22}$ aliphatic group; each $Q^{21}$ is independently a $C_1$–$C_4$ alkyl group, benzyl, —$CH_2CH_2OH$, —$CH_2CH(OH)CH_3$, or $R_{21}$—C(O)—(O—(Alk$^{21}$))$_{1-4}$; each Alk$^{21}$ is independently $C_2H_4$, $C_3H_6$ or $C_4H_8$; and A$^-$ is an anion as defined above;

(xx) compounds of the formula:

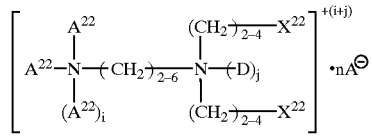

wherein each $A^{22}$ is independently a $C_1$–$C_3$ alkyl, benzyl, or H—Alk$^{22}$—O)$_{1-3}$—Alk$^{22}$—, wherein each Alk$^{22}$ represents —$CH_2CH_2$—, —$CH(CH_3)CH_2$—, or —$CH_2CH(CH_3)$—, provided further that one of the $A^{22}$ can be hydrogen; D is methyl, ethyl, propyl, —$CH_2)_{1-3}COO$—, benzyl or hydrogen; i is 0 or 1 and j is 0 or 1, provided that the sum of (i+j) is 1 or 2; each $X^{22}$ is a $C_{11}$–$C_{23}$ aliphatic group containing up to 3 carbon-carbon double bonds; n is two minus the number of —$CH_2)_{1-3}COO$— substituents present; and A$^-$ is an anion as defined above;

(xxi) compounds of the formula:

wherein each $R_{23}$ is independently a $C_8$–$C_{22}$ alkyl or alkenyl group; $R_{23a}$ is a $C_1$–$C_3$ straight or branched alkyl or hydroxyalkyl group, benzyl, or —$C_2H_4OC(O)R_{26}$, wherein $R_{26}$ is a $C_8$–$C_{22}$ straight or branched alkyl or alkenyl group; $R_{23b}$ is —H, —$CH_3$, —$C_2H_5$, or benzyl; and A$^-$ is an anion as defined above; and (xxii) compounds of the following structural formulas:

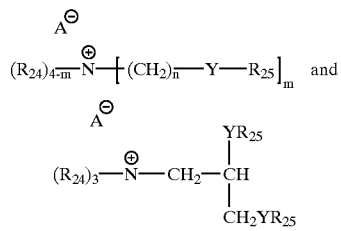

wherein each $R_{24}$ is independently a $C_1$–$C_8$ straight or branched alkyl or alkenyl containing 0 to 3 hydroxyl groups; each $R_{25}$ is a $C_{10}$–$C_{22}$ straight or branched alkyl or alkenyl group containing 0 to 3 hydroxyl groups; each Y is —O—C(O)— or —C(O)—O—; each m is 1 to 3; each n is from 1 to 8; and A$^-$ is an anion as defined above.

Preferred examples of compounds of structural formulas (xxii) include methyl diethanolamine (MDEA) ester quats, triethanolamine (TEA) ester quats, for example, di(tallow carboxyethyl) hydroxyethyl methylammonium methosulfate, available from Witco Corporation under the tradename REWOQUAT® WE 16, or epichlorohydrin-based ester quats, all of which are used and accepted as fabric softeners worldwide because of their favorable biodegradation profiles, but usually lack the optimum softening performance of other quats.

Additional compounds useful in the present invention include polyester polyquaternary compounds, including but not limited to:

(xxiii) compounds of the following structural formula:

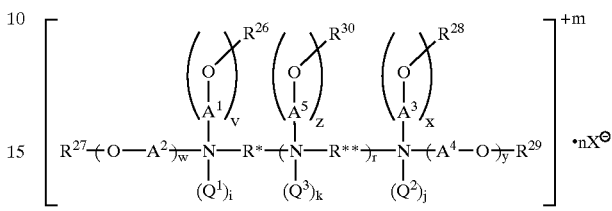

wherein each of R* and R** is independently a linear, branched or cyclic alkylene group containing 2 to 12 carbon atoms, wherein no two nitrogen atoms are separated by fewer than 2 carbon atoms;

each of $A^1$, $A^2$, $A^3$, $A^4$, and $A^5$ is independently a straight or branched alkylene containing 2 to 4 carbon atoms;

each of $R^{26}$, $R^{27}$, $R^{28}$, $R^{29}$, and $R^{30}$ is independently —H or $R_AC(O)$— wherein $R^A$ is straight or branched alkyl or alkenyl containing 7 to 21 carbon atoms and 0 to 4 carbon-carbon double bonds; provided that at least one of $R^{26}$, $R^{27}$, $R^{28}$, $R^{29}$, or $R^{50}$ is $R^AC(O)$—; each of $Q^1$, $Q^2$ and $Q^3$ is independently —H, $CH_3$, $C_2H_5$, —$C_3H_7$, —$C_4H_5$, benzyl, —$CH_2COOH$, or —$CH_2COOX^-$; or, if R* is a —$CH_2CH_2$— group, $Q^1$ and $Q^3$ together or $Q^1$ and $Q^2$ together may be a —$CH_2CH_2$— group to form a six-membered piperazine ring; or, if R** is a —$CH_2CH_2$— group, $Q^3$ and $Q^3$ together may be a —$CH_2CH_2$— group to form a six-membered piperazine ring; m is 0 to 4; r is 0 to 2; each of v, w, x, y, and z is independently 1 to 8; i is 0 to 1, j is 0 to 1, and each k is 0 to 1, and the sum of (i+j+k) is 0 to 4; each X$^-$ is independently an anion that may be selected, without limitation, from the group consisting of fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like; and n is the number of moles of X$^-$ needed to give the compound of structural formula (xxiii) a zero net charge. Compounds of structural formula (xxiii), formulations thereof, and uses thereof, form the subject matter of pending U.S. application Ser. No. 09/170,623, filed on Oct. 13, 1998, which is incorporated by reference in its entirety; and (xxiv) compounds of the following structural formulas:

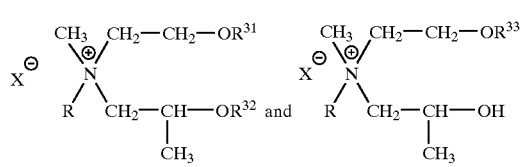

wherein R is —H, —$CH_3$ or —$C_2H_5$;

$R^1$, $R^2$, and $R^3$ are each independently of one another fatty acid radicals having 6–22 carbon atoms; and X$^-$ is an inorganic or organic anion that may be selected, without limitation, from the group consisting of fluoride, chloride, bromide, iodide, chlorite, chlorate, hydroxide, hypophosphite, phosphite, phosphate, carbonate, formate, acetate, lactate, and other carboxylates, oxalate, methyl sulfate, ethyl sulfate, benzoate, and salicylate, and the like. Compounds of structural formula (xxiv), formulations thereof, and uses thereof, form the subject matter of pending PCT application No. PCT/US99/00213, filed on Jan. 6, 1999 and pending PCT application No. PCT/US99/00295, filed on Jan. 7, 1999, both of which are incorporated by reference in their entireties.

F. Diol and Diol Alkoxylate Coupling Agent Additives

In a preferred embodiment of this invention, Inventive Ester Quat formulations may be formulated using an appropriate amount of one or more straight or branched alkyl diols containing 4 to 12 carbon atoms, and/or alkoxylates of such diols with up to 40 alkoxy units per diol moiety, wherein the alkoxylate chains are composed of alkoxy units which are ethoxy, propoxy or butoxy or mixtures thereof, and preferably ethoxy or propoxy. These diol and diol alkoxylate hydrotropes or coupling agents are added to the formulations to increase the amount of the relatively water-insoluble surfactants that can be solubilized into the system. In most cases, they do not act as surfactants to lower surface tension, but they often allow surfactants in the presence of salts or electrolytes to be added and subsequently dispersed into water at higher concentrations or at lower viscosities of the formulation than is otherwise achieved using only surfactant and water. These coupling agents assist surfactants by increasing the surfactant's solubility in water and its stability in the formulation, especially in the presence of salts, electrolytes and/or pH agents.

These diols and alkoxylates correspond to structural formula (T)

$$HO\text{---}(X\text{---}O)_x R^T\text{---}(O\text{---}Y)_y OH \quad (T)$$

wherein each X and each Y is ethylene (that is, $\text{---}C_2H_4\text{---}$), propylene (that is, $\text{---}C_3H_6\text{---}$), or butylene (that is, $\text{---}C_4H_8\text{---}$); x is 0–40; y is 0–40; the sum (x+y) is 0–40; and $R^T$ is straight, branched or cyclic alkyl containing 4 to 12 carbon atoms. Preferably, $R^T$ contains 7–12 or even 7–9 carbon atoms.

The alkylene residue $R^T$ in structural formula (T) represents a saturated, straight-chain, branched-chain, or cyclic moiety containing 4 to 12 carbon atoms. It is preferred that $R^T$ is branched, wherein the term "branched" is intended to encompass structures having one side alkyl chain, more than one side alkyl chain, or one or more side alkyl chains, one or more of which is itself branched. Branched structures include cyclic structures substituted with one or more alkyl groups, the alkyl groups being straight or branched. Examples of suitable $R^T$ groups include such groups as $\text{---}C(CH_3)_2CH_2\text{---}, \text{---}CH_2C(CH_3)CH_2\text{---}, \text{---}CH_2CH_2\text{---}, \text{---}CH_2CH(CH_3)_2CH_2\text{---}, \text{---}CH_2CH(CH_2CH_3)CH_2CH_2CH_2CH_2\text{---}, \text{---}(CH_2)_6\text{---}, \text{---}CH_2CH(CH_2CH_2CH_2CH_3)\text{---}, \text{---}CH_2C(CH_3)_2CH(CH(CH_3)_2)\text{---},$ and

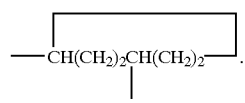

In the alkoxylated diols, the number of repeating units in each poly(alkoxy) chain can be up to 40, but it is preferred that each chain contains 1 to 10 repeating alkoxy units or more preferably 1 to 5 alkoxy units. The preferred alkoxy chains are poly(ethoxy), or are composed of 1 to 2 ethoxy units capped with a chain of 1 to 5 propoxy units.

Compounds of structural formula (T) defined above are in many instances commercially available. Compounds of structural formula (T) can be prepared in straightforward manner familiar to those of ordinary skill in this art by obtaining or preparing the corresponding precursor diol of structural formula HO—$R^T$—OH, and then alkoxylating the precursor diol with a stoichiometrically appropriate number of moles of the desired corresponding alkylene oxide, such as ethylene oxide, propylene oxide, and/or butylene oxide. In those cases where it is desired to alkoxylate only one of the hydroxyl groups on the precursor diol, in some embodiments, the alkoxylation will preferentially occur at only one of the hydroxyl groups, particularly where one of hydroxyl groups is a primary hydroxyl and the other is a secondary hydroxyl. However, in those cases where both hydroxyl groups on the precursor diol might tend to alkoxylate, but alkoxylation at only one of the hydroxyl groups is desired, the hydroxyl group at which alkoxylation is desired not to occur can be protected by preliminarily reacting the hydroxyl group with a suitable protecting group such as a lower alkyl moiety or an esterifying substituent. Thereafter, following the alkoxylation, the protecting group is removed in a known manner.

Preferred examples of compounds of the foregoing structural formula (T) include any one, or mixtures, of 2,2,4-trimethyl-1,3-pentanediol (TMPD) and/or 2-ethylhexane-1,3-diol, and/or the reaction product of TMPD and/or 2-ethylhexane-1,3-diol with 1 to 10 moles of ethylene oxide, and preferably with 1 to 5 moles of ethylene oxide, as well as analogs alkoxylated with other $C_3$ or $C_4$ alkyl oxides or mixtures of any of $C_2$, $C_3$ and/or $C_4$ alkyl oxides. Since the diol which is alkoxylated includes one primary hydroxyl group and one secondary hydroxyl group, the alkoxylation proceeds predominantly at the primary hydroxyl group.

The compositions which contain one or more Inventive Ester Quats can also contain one or a mixture of compounds of structural formula (E)

$$R^{E1}\text{---}C(O)O\text{---}R^{E2}\text{---}OC(O)R^{E3})_{0-1} \quad (E)$$

wherein $R^{E1}$ is straight, cyclic or branched alkyl containing 1–15 carbon atoms, and $R^{E1}$ is substituted with 0 to 3 hydroxyl groups; and wherein $R^{E2}$ is straight, cyclic or branched alkyl containing 1 to 10 carbon atoms, and $R^{E2}$ is substituted with 0 to 3 hydroxyl groups, and $R^{E2}$ can optionally be substituted with a group of the structure —OC(O)—$R^{E3}$ wherein $R^{E3}$ is straight, cyclic or branched alkyl containing 1 to 15 carbon atoms and is optionally substituted with a hydroxyl group.

Preferred compounds of structural formula (E) include those wherein $R^{E2}$ contains 2 or 3 carbon atoms, for example, glycol and glyceryl derivative, or $R^{E2}$ contains about 8 carbon atoms, for example, derivatives of 2,2,4-trimethylpentanediol or of 2-ethylhexanediol. Preferred compounds of structural formula (E) include 2,2,4-trimethyl-1,3-pentanediol monoisobutyrate, hydroxypivalyl hydroxypivalate, and the monoester of TMPD with hydroxypivalic acid.

Formulations can also contain what may be termed aesthetic additives to provide properties such as fragrance, preservative, viscosity control, and color. Such additives are discussed below. The formulations according to the present invention generally exhibit highly satisfactory viscosities, generally as pourable and even sprayable fluids.

G. Additional Surfactants

Other suitable non-quaternary compound surfactants, whether anionic, cationic, zwitterionic, nonionic, or amphoteric, may be used in combination with the compounds and formulations of the invention, depending on the application.

1. General Surfactants

For example, in a fabric softening application, suitable anionic surfactants may include, without limitation, the alkylbenzene sulfonates, α-olefin sulfonates, and xylene sulfonates available from Witco Corporation under the WITCONATE® trademark. While these surfactants may be unsuitable for personal care applications because they may cause skin and eye irritation, surfactants suitable for personal care applications may be used in other non-personal care applications.

2. Personal Care Surfactants

For personal care applications, suitable anionic surfactants would include, without limitation, ammonium lauryl sulfate, sodium lauryl sulfate, any α-olefin sulfonate, ammonium laureth sulfate (2 or 3 moles), sodium laureth sulfate (2 or 3 moles), sodium myristyl sulfate, sodium myristeth sulfate (1–4 moles), ammonium xylene sulfonate, sodium xylene sulfonate, TEA (triethanol amine) dodecylbenzene sulfonate, TEA lauryl sulfate, ammonium pareth sulfate, sodium pareth sulfate, sodium oleth sulfate, derivatives of any of the forgoing, and similar compounds known to those of skill in the art, and mixtures thereof. For personal care applications, suitable amphoteric surfactants or nonionic surfactants include betaines, sulfosuccinates, mono- and diglycerides, glycinates, sugars and derivatives thereof, hydroxysultaines, mono- and diacetates, ethoxylated derivatives of any of the forgoing, and similar compounds known to those of skill in the art, and mixtures thereof. Other surfactants that may be added to these systems include, but are not limited to, alkanolamides, come of which are available from Witco Corporation under the WITCAMDE® tradename. In addition, various amine oxides may be used in these systems, several of which are available from Witco Corporation under the VAROX® tradename.

H. Personal Care Emollients and Emulsifiers

Emollients and emulsifiers are also typically used in personal care formulations in combination with the amine compounds and quaternary compounds of the invention, depending on the application. Indeed, Inventive Ester Quats can be formulated into emulsions that can be used as skin or hair conditioners which can take the form of lotions, creams, leave-on products, and rinse-off products. These systems may also include additional products that may improve the feel and conditioning, or the emolliency of skin and hair. Some of these products are available from Witco Corporation under the KEMSTRENE®, WITCONOL™, STARFOL®, and KEMESTER® tradenames. Although these emollients and emulsifiers are used in skin and hair conditioners, they can also be incorporated into other compositions containing Inventive Ester Quats for use in other products, such as tissues, that may contain a suitable lotion or cream therein.

A soft tissue that provides a soothing feel can be made by incorporating into the tissue a softening composition, whether or not aqueous, containing a combination of selected ingredients, including Inventive Ester Quats. Preferred tissues may include a softening composition comprising glycerin and one or more Inventive Ester Quats. The add-on amount of the softening composition can be any effective amount, the term "effective amount" in this context meaning any amount that produces the benefits of the softening composition desired, for example, providing a softening or moisturizing effect on skin brought into contact with tissues containing the softening composition. In general, the amount of softening composition will be about 3 wt. % to about 30 wt. %, more preferably about 3 wt. % to about 20 wt. %, and still more preferably about 5 wt. % to about 15 wt. %, based on the weight of the untreated tissue. The higher add-on amounts are more likely to leave behind a detectable residue on the skin, whereas the lower add-on amounts are less likely to do so. As would be understood by those of skill in the art, water can be added to the formulation to reduce the viscosity of the glycerin and to make the formulation more suitable for application. The amount of Inventive Ester Quat in the softening composition is generally from about 0.2 wt. % to about 5 wt. %, more preferably from about 0.3 wt. % to about 3 wt. %. and most preferably from about 0.5 wt. % to about 1 wt. % of the softening composition. The amount of glycerin, diol, glycol, or similar additive or mixture thereof in the softening composition can be from about 20 wt. % to about 98 wt. %, preferably from about 60 wt. % to about 80 wt. %, and most preferably from about 40 wt. % to about 60 wt. % of the softening composition. Other optional ingredients include aloe, humectants, skin protectants, preservatives, and feel modifiers. The softening composition, which can be in the form of a solution or suspension, can be incorporated into the tissue by any suitable means such as spraying or printing onto the surface of the tissue. The tissue to which the softening composition is applied can be any tissue useful as facial tissue, bath tissue, or towels, and such tissues can be produced by throughdrying or wet-pressing tissue making processes and can be creped or uncreped, layered or non-layered (blended).

I. Other Additives

Other additives and adjuvants can be optionally added to the compounds and formulations of the present invention for their known purposes. Such additives and adjuvants include, but are not limited to, perfumes, preservatives including bacteriocides and fungicides, insect and moth repelling agents, polymeric soil release agents, antistatic agents, dyes and colorants, especially bluing agents, viscosity control agents, antioxidants, silicones, defoaming agents, antifoaming agents, emulsifiers, brighteners, opacifiers, freeze-thaw control agents, shrinkage control agents, aloe, humectants, skin protectants, feel modifiers, waxes, glycerin, vitamins and extracts, and mixtures thereof. The identity and amounts of the additives and adjuvants used would depend on the application of the formulation and its desired properties; many of the additives set forth below are not exclusive to any one formulation or application, but may be appropriate for many different formulations or applications. The additives and adjuvants are well-known to those of skill in the art and the additives and adjuvants listed below are not meant to be an exhaustive list but merely a guide to the types of additives that would typically be used.

1. Papermaking and Tissuemaking Additives

Paper and tissue softening or debonding compositions of the present invention would typically contain other chemicals commonly used in papermaking or tissuemaking, or to the paper or tissue furnish so long as they do not significantly and adversely affect the softening, absorbency of the fibrous material, and softness enhancing actions of the amine and quaternary ammonium softening compounds of the present invention.

A. Wetting Agents

The present invention may contain as an optional ingredient from about 0.005% to about 3.0%, more preferably from about 0.03% to 1.0% by weight, on a dry fiber basis of a wetting agent. Such wetting agents may be selected from polyhydroxy compounds, nonionic surfactants such as alkoxylated compounds and linear alkoxylated alcohols, and anionic wetting agents such as diisooctylsulfosuccinate (DOSS), available from Witco Corporation under the tradename EMCOL® 4500.

Examples of water soluble polyhydroxy compounds that can be used as wetting agents in the present invention include glycerol, polyglycerols having a weight-average molecular weight of from about 150 to about 800, and polyoxyethylene glycols and polyoxypropylene glycols having a weight-average molecular weight of from about 200 to about 4000, preferably from about 200 to about 1000, most preferably from about 200 to about 600. Polyoxyethylene glycols having an weight-average molecular weight of about 200 to about 600 are especially preferred. Mixtures of the above-described polyhydroxy compounds may also be used. A particularly preferred polyhydroxy compound is polyoxyethylene glycol having an weight average molecular weight of about 400, available from Union Carbide Corporation under the tradename PEG-400.

Suitable nonionic surfactants can be used as wetting agents in the present invention. These include addition products of alkoxylating agents such as ethylene oxide (EO), propylene oxide (PO), or butylene oxide (BO), or a mixture thereof, with fatty alcohols, fatty acids, fatty amines, etc. Any of the alkoxylated materials of the particular type described hereinafter can be used as the nonionic surfactant. Suitable compounds are substantially water-soluble surfactants of the general formula:

$$R_{10}-Y-(C_2H_4O)_z-C_2H_4OH$$

wherein $R_{10}$ for both solid and liquid compositions is selected from the group consisting of primary, secondary and branched chain alkyl and/or acyl hydrocarbyl groups; primary, secondary and branched chain alkenyl hydrocarbyl groups; and primary, secondary and branched chain alkyl- and alkenyl-substituted phenolic hydrocarbyl groups; the hydrocarbyl groups having a hydrocarbyl chain length of from about 8 to about 20, preferably from about 10 to about 18 carbon atoms. More preferably the hydrocarbyl chain length for liquid compositions is from about 16 to about 18 carbon atoms and for solid compositions from about 10 to about 14 carbon atoms. In the general formula for the ethoxylated nonionic surfactants herein, Y is typically —O—, —C(O)O—, —C(O)N($R_{11}$)—, or —C(O)N($R_{11}$) $R_{11}$—, in which $R_{10}$, and $R_{11}$, when present, have the meanings given hereinbefore, and/or $R_{11}$ can be hydrogen, and z is at least about 8, preferably at least about 10–11. Performance and, usually, stability of the softener composition decrease when fewer ethoxylate groups are present.

Examples of nonionic surfactants according to the above formula follow, wherein the integer in parenthesis identifies the number of EO groups in the molecule. In particular, the deco-, under-, dodder-, terraced-, and pentadecaethoxylates of n-hexadecanol and n-octadecanol are useful wetting agents in the context of this invention. Exemplary ethoxylated primary alcohols useful herein as the viscosity/dispersibility modifiers of the compositions are n-octadecanol EO(10); and n-decanol EO(11). The ethoxylates of mixed natural or synthetic alcohols in the "oleyl" chain length range are also useful herein. Specific examples of such materials include oleyl alcohol EO(11), oleyl alcohol EO(18), and oleyl alcohol EO(25). In addition, the deca-, undeca-, dodeca-, tetradeca-, pentadeca-, octadeca-, and nonadecaethoxylates of 3-hexadecanol, 2-octadecanol, 4-eicosanol, and 5-eicosanol can be used as wetting agents in the present invention.

As in the case of the alcohol alkoxylates, the hexa- through octadecaethoxylates of alkylated phenols, particularly monohydric alkylphenols, are useful as the viscosity/dispersibility modifiers of the instant compositions. In particular, the hexa- through octadeca-ethoxylates of p-tridecylphenol, m-pentadecylphenol, and the like, are useful herein. Exemplary ethoxylated alkylphenols useful as the wetting agents of the mixtures herein are: p-tridecylphenol EO(11) and p-pentadecylphenol EO(18). As used herein and as generally recognized in the art, a phenylene group in the nonionic formula is the equivalent of an alkylene group containing from 2 to 4 carbon atoms. It should also be noted that the alkenyl alcohols, both primary and secondary, and alkenyl phenols corresponding to those disclosed immediately hereinabove can be ethoxylated and used as wetting agents in the present invention. Furthermore, branched-chain primary and secondary alcohols, usually synthesized using the well-known Oxo Process, can be ethoxylated and can be used as wetting agents in the present invention.

The above ethoxylated nonionic surfactants are useful in the present compositions alone or in combination, and the term "nonionic surfactant" encompasses mixed nonionic surface active agents. The level of surfactant, if used, is preferably from about 0.01% to about 2.0% by weight, based on the dry fiber weight of the tissue paper. The surfactants preferably have alkyl chains with eight or more carbon atoms. Exemplary anionic surfactants are linear alkyl sulfonates, and alkylbenzene sulfonates. Exemplary nonionic surfactants are alkylglycosides including alkylglycoside esters such as that available from Croda, Inc. under the tradename CRODESTA™ SL40; alkylglycoside ethers as described in U.S. Pat. No. 4,011,389, which patent is herein incorporated by reference in its entirety; and alkylpolyethoxylated esters such as those available from Lonza Inc. under the tradename PEGOSPERSE® 200 ML and available from Rhône-Poulenc Corporation under the tradename IGEPAL® RC-520.

B. Strength Additives

Other types of chemicals which may be added, include the strength additives to increase the dry tensile strength and the wet burst of the tissue webs. The present invention may contain as an optional component from about 0.01 wt. % to about 3.0 wt. %, more preferably from about 0.3 wt. % to about 1.5 wt. %, on a dry fiber weight basis, of a water-soluble strength additive resin. Such water-soluble strength additive resins may include dry strength additives, permanent wet strength resins, temporary wet strength resins, or a compatible mixture thereof.

Examples of suitable dry strength additives include carboxymethyl cellulose and cationic polymers from the ACCO chemical family such as ACCO 711 and ACCO 514, with ACCO chemical family being preferred. These materials are available commercially from the American Cyanamid Company.

As used herein, the term "permanent wet strength resin" refers to a resin which allows the paper sheet, when placed in an aqueous medium, to keep a majority of its initial wet strength for a period of time greater than at least two minutes. Permanent wet strength resins useful herein can be of several types. Generally, those resins which have previously found and which will hereafter find utility in the papermaking art are useful herein. Numerous examples are described by Westfelt in *Cellulose Chemistry and Technology*, Volume 13, at pages 813–825 (1979), which is herein incorporated by reference in its entirety. Usually, the wet strength resins are water-soluble, cationic materials. That is to say, the resins are water-soluble at the time they are added to the papermaking furnish. It is quite possible, and even to be expected, that subsequent events such as cross-linking will render the resins insoluble in water. Further, some resins are soluble only under specific conditions, such as over a limited pH range. Wet strength resins are generally believed to undergo a cross-linking or other curing reactions after they have been deposited on, within, or among the papermaking fibers. However, such cross-linking or curing does not normally occur so long as substantial amounts of water are present.

Of particular utility are the various polyamide-epichlorohydrin resins. These materials are low molecular weight polymers provided with reactive functional groups such as amino, epoxy, and azetidinium groups. The patent literature is replete with descriptions of processes for making such materials, for example, U.S. Pat. Nos. 3,700,623 and 3,772,076, both herein incorporated by reference in their entireties. Such polyamide-epichlorohydrin resins available from Hercules Inc. under the trademarks KYMENE® 557H and KYMENE® 2064 are particularly useful in this invention. In addition, base-activated polyamide-epichlorohydrin resins are generally described in U.S. Pat. Nos. 3,855,158; 3,899,388; 4,129,528; 4,147,586; and 4,222,921, which patents are herein incorporated by reference in their entireties. These materials are available from the Monsanto Company under the tradename SANTO-REST™, such as SANTO-REST™ 31.

Other water-soluble cationic resins useful herein are the polyacrylamide resins, such as those generally described in U.S. Pat. Nos. 3,556,932 and 3,556,933, which are both herein incorporated by reference in their entireties. Such materials are available from the American Cyanamid Company under the tradename PAREZ®, such as PAREZ® 631NC. Other types of water-soluble resins useful in the present invention include acrylic emulsions and anionic styrene-butadiene latexes, numerous examples of which are provided in U.S. Pat. No. 3,844,880, which is herein incorporated by reference in its entirety. Still other water-soluble cationic resins finding utility in this invention are the urea formaldehyde and melamine formaldehyde resins. These polyfunctional, reactive polymers have molecular weights on the order of a few thousand. The more common functional groups include nitrogen containing groups such as amino groups and methylol groups attached to nitrogen. Although less preferred, polyethylenimine-type resins find utility in the present invention. More complete descriptions of the aforementioned water-soluble resins, including their manufacture, can be found in TAPPI Monograph Series No. 29, *Wet Strength In Paper and Paperboard*, Technical Association of the Pulp and Paper Industry (New York: 1965), which is herein incorporated by reference in its entirety.

The above-mentioned permanent wet strength additives are those that produce paper products with permanent wet strength, that is, paper which when placed in an aqueous medium retains a substantial portion of its initial wet strength over time. However, permanent wet strength in some types of paper products can be an unnecessary and undesirable property. Paper products such as toilet tissues, etc., are generally disposed of after brief periods of use into septic systems and the like. Clogging of these systems can result if the paper product permanently retains its hydrolysis-resistant strength properties. Thus, manufacturers use temporary wet strength additives to paper products for which wet strength is sufficient for the intended use, but which then decays upon soaking in water. Decay of the wet strength facilitates flow of the paper product through septic systems.

Examples of suitable temporary wet strength resins include modified starch temporary wet strength agents, such as that available from the National Starch and Chemical Corporation under the tradename NATIONAL STARCH™ 78-0080. This type of wet strength agent can be made by reacting dimethoxyethyl-N-methyl-chloroacetamide with cationic starch polymers. Modified starch temporary wet strength agents are also described in U.S. Pat. Nos. 4,675,394 and 4,981,557, both of which are herein incorporated by reference in their entireties.

C. Other Additives

Other suitable additives may be used in paper and tissue-making applications, depending on the application. For example, glycerin may also be used in the composition and formulations thereof. If used, the amount of glycerin in the aqueous softening composition can be from about 0.1 wt. % to about 98 wt. %, more preferably from about 60 to about 80 wt. %, and still more preferably from about 40 to about 60 wt. %, of the composition. In addition, the compositions and formulations of the instant invention can contain glycols, such as propylene glycol or polyethylene glycol, or mineral oils instead of, or, in addition, to glycerin in such formulations. Silicones and other additives set forth below may also be used in combination with Inventive Ester Quats, either together or sequentially in the papermaking or tissue-making process, for example, when Inventive Ester Quats are applied to the wet end and a silicone is topically applied by print or spray or, alternatively, the Inventive Ester Quat and silicone are both used in the wet end or are both sprayed topically on the furnish.

2. Perfumes

As noted above, perfumes or fragrance materials may be added to the compositions and formulations of the present invention. The selection of the perfume or perfumes is based upon the application, the desired effect on the consumer, and preferences of the formulator. The perfume selected for use in the compositions and formulations of the present invention contains ingredients with odor characteristics which are preferred in order to provide a fresh impression on the surface to which the composition is directed, for example, those which provide a fresh impression for fabrics if a fabric softener treatment formulation is prepared. Such perfume is preferably present at a level of from about 0.01% to about 5%, preferably from about 0.05% to about 3%, more preferably from about 0.1% to about 2%, by weight of the total composition.

Preferably, the perfume is composed of fragrance materials selected from the group consisting of aromatic and aliphatic esters having molecular weights from about 130 to about 250; aliphatic and aromatic alcohols having molecular weights from about 90 to about 240 m: aliphatic ketones having molecular weights from about 150 to about 260; aromatic ketones having molecular weights from about 150 to about 270; aromatic and aliphatic lactones having molecular weights from about 130 to about 290; aliphatic aldehydes having molecular weights from about 140 to about 200; aromatic aldehydes having molecular weights from about 90 to about 230; aliphatic and aromatic ethers having molecular weights from about 150 to about 270; and condensation products of aldehydes and amines having molecular weights from about 180 to about 320; and mixtures thereof.

The selection of such perfumes and fragrance materials are well-known to those of skill in the art, both for desired scent and appropriate scent impact. For example, when high initial perfume odor impact on fabrics is desired, it is preferable to select a perfume containing perfume ingredients which are not too hydrophobic. The degree of hydrophobicity of a perfume ingredient can be correlated with its octanol/water partitioning coefficient P, the ratio between its equilibrium concentration in octanol and in water. Thus, a perfume ingredient with a greater partitioning coefficient P is more hydrophobic and a perfume ingredient with a smaller partitioning coefficient P is more hydrophilic; a selection based on the application and intended effect may be made accordingly. For example, in a fabric application, the preferred perfume ingredients would have an octanol/water partitioning coefficient P of about 1,000 or smaller.

3. Preservatives

Optionally, solubilized, water-soluble preservatives can be added to the present invention. Preservatives are especially preferred when organic compounds that are subject to microorganisms are added to the compositions of the present invention, especially when they are used in aqueous compositions. When such compounds are present, long term and even short term storage stability of the compositions and formulations becomes an important issue since contamination by certain microorganisms with subsequent microbial growth often results in an unsightly and/or malodorous solution. Therefore, because microbial growth in these compositions and formulations is highly objectionable when it occurs, it is preferable to include a solubilized water-soluble, antimicrobial preservative, which is effective for inhibiting and/or regulating microbial growth in order to increase storage stability of the preferably clear and often aqueous compositions and formulations of the present invention.

Typical microorganisms that can be found in personal care products include bacteria, for example, *Bacillus thuringiensis* (cereus group) and *Bacillus sphaericus*, and fungi, for example, *Aspergillus ustus*. *Bacillus sphaericus* is one of the most numerous members of Bacillus species in soils. In addition, microorganisms such as *Escherichia coli* and *Pseudomonas aerupinosa* are found in some water sources, and can be introduced during the preparation of aqueous solutions of the present invention.

It is preferable to use a broad spectrum preservative, for example, one that is effective on both bacteria (both gram positive and gram negative) and fungi. A limited spectrum preservative, for example, one that is only effective on a single group of microorganisms, for example, fungi, can be used in combination with a broad spectrum preservative or other limited spectrum preservatives with complimentary and/or supplementary activity. A mixture of broad spectrum preservatives can also be used.

Antimicrobial preservatives useful in the present invention can be biocidal compounds, that is, substances that kill microorganisms, or biostatic compounds, that is, substances that inhibit and/or regulate the growth of microorganisms. Preferred antimicrobial preservatives are those that are water-soluble and are effective at low levels. In general, the water-soluble preservatives that may be used include organic sulfur compounds, halogenated compounds, cyclic organic nitrogen compounds, low molecular weight aldehydes, quaternary compounds, dehydroacetic acid, phenyl and phenoxy compounds, and mixtures thereof. Examples of preservatives useful in the present invention include, but are not limited to, the short chain alkyl esters of p-hydroxybenzoic acid (commonly known as parabens); N-(4-chlorophenyl)-N-(3,4-dichlorophenyl) urea (also known as 3,4,4'-trichlorocarbanilide or triclocarban); 2,4,4'-trichloro-2'-hydroxydiphenyl ether, commonly known as triclosan); the isothiazoline formulation available from Sterling-Winthrop Group Ltd. under the tradename PARMETOL™ K-40; a mixture of about 77% 5-chloro-2-methyl-4-isothiazolin-3-one and about 23% 2-methyl-4-isothiazolin-3-one, a broad spectrum preservative available from the Rohm and Haas Company as a 1.5% aqueous solution under the tradename KATHON® CG; 5-bromo-5-nitro-1,3-dioxane, available from Henkel Corporation under the tradename BRONIDOX® L; 2-bromo-2-nitropropane-1,3-diol, available from Inolex Chemical Company under the tradename BRONOPOL™; 1,1'-hexamethylenebis(5-(p-chlorophenyl)biguanide) (commonly known as chlorhexidine) and its salts, for example, with acetic and digluconic acids; a 95:5 mixture of 1,3-bis(hydroxymethyl)-5,5-dimethyl-2,4-imidazolidinedione and 3-butyl-2-iodopropynyl carbamate, available from Lonza Inc. under the tradename GLYDANT® Plus; N-[1,3-bis (hydroxymethyl)2,5-dioxo-4-imidazolidinyl]-N,N'-bis (hydroxy-methyl) urea, commonly known as diazolidinyl urea, available from Sutton Laboratories, Inc. under the tradename GERMALL® II; N,N"-methylenebis[N'-[1-(hydroxymethyl)-2,5-dioxo-4-imidazolidinyl]urea] (commonly known as imidazolidinyl urea), available, for example, from 3V-Sigma under the tradename ABIOL™, from Induchem under the tradename UNICIDE® U-13, and from Sutton Laboratories, Inc. under the tradename GERMALL® 115; polymethoxy bicyclic oxazolidine, available from Hüls America Inc. under the tradename NUOSEPT®; formaldehyde; glutaraldehyde; polyaminopropyl biguanide, available from ICI Americas, Inc. under the tradename COSMOCIL® CQ or from Brooks Industries Inc. under the tradename MIKROKILL™; dehydroacetic acid; and mixtures thereof. In general, however, the preservative can be any organic preservative material which is appropriate for the application, for example, in a fabric softening application such preservative will preferably not cause damage to fabric appearance, for example, discoloration, coloration, or bleaching of the fabric.

If the antimicrobial preservative is included in the compositions and formulations of the present invention, it is preferably present in an effective amount, wherein an "effective amount" means a level sufficient to prevent spoilage or prevent growth of inadvertently added microorganisms for a specific period of time. Preferred levels of preservative are from about 0.0001% to about 0.5%, more preferably from about 0.0002% to about 0.2%, most preferably from about 0.0003% to about 0.1%, by weight of the composition.

Bacteriostatic effects can sometimes be obtained for aqueous compositions by adjusting the composition pH to an acid pH, for example, less than about pH 4, preferably less than about pH 3. Low pH for microbial control is not a preferred approach in the present invention because the low pH can cause chemical degradation of the cyclodextrins. Therefore, aqueous compositions of the present invention should have a pH greater than about 3.0, preferably greater than about 4.0, more preferably greater than about 4.5. As stated above, it is preferable to use the preservative at an effective amount, as defined hereinabove. Optionally, however, the preservative can be used at a level which provides an antimicrobial effect on the treated fabrics.

4. Antistatic Agents

The composition of the present invention can optionally contain an effective amount of antistatic agent to provide the treated clothes with in-wear static. Preferred antistatic agents are those that are water soluble in at least effective amount, such that the composition remains a clear solution. Examples of these antistatic agents include monoalkyl cationic quaternary ammonium compounds, for example, mono ($C_{10}$–$C_{14}$ alkyl)trimethyl ammonium halide, such as monolauryl trimethyl ammonium chloride, hydroxycetyl hydroxyethyl dimethyl ammonium chloride (available from Henkel Corporation under the tradename DEHYQUART® E), and ethyl bis(polyethoxyethanol) alkylammonium ethylsulfate (available from Witco Corporation under the tradename VARIQUAT® 66), polyethylene glycols, polymeric quaternary ammonium salts (such as those available from Rhône-Poulenc Corporation under the MRAPOL® tradename), quaternized polyethyleneimines, vinylpyrrolidone/methacrylamidopropyltrimethylammonium chloride copolymer (available from GAF Corporation under the tradename GAFQUAT® HS-100), triethonium hydrolyzed collagen ethosulfate (available from Maybrook Inc. under the tradename QUAT-PRO™ E), and mixtures thereof. When an antistatic agent is used it is typically present at a level of from about 0.05% to about 10%, preferably from about 0.1% to about 5%, more preferably from about 0.3% to about 3%, by weight of the composition.

5. Defoaming and Antifoaming Agents

In many applications, it is preferred that a defoaming or antifoaming agent is used, to avoid foam formation during application and use of the Inventive Ester Quats. Typical defoaming or antifoaming agents include various alcohols, hydrocarbons, silicones, alcohol alkoxylates, propoxylated alkyl amines, polyacrylates, alkyleneoxide copolymers, fatty acids, fatty acid sulfonates and blends of fatty acids and esters in hydrocarbons. It is also preferred that polyethoxylated agents such as polyethylene glycol or VARIQUAT® 66 are not used when α-cyclodextrin is used.

6. Enzymes

In another useful aspect of the present invention, the compositions can also contain an effective amount of an enzyme component which comprises one or more enzymes capable of assisting the removal of stain or soil from a surface. The enzyme component includes any enzyme which assists in the removal of soil or stain from a substrate (including particularly fabric and hard surfaces). Particularly useful enzymes include carbohydrases, especially amylases, α-amylases, and β-amylases, and cellulases; lipases; and proteases. Amylases and cellulases are particularly useful against carbohydrates, for example. starches and other polysaccharides. Thus amylases and cellulases provide cleaning activity against plant-derived soil and stains, such as grass stains, coffee, tea, grape juice, ketchup, and the like. Lipases are esterases which hydrolyze esters of glycerol and fatty acids. Thus, lipases are particularly useful in providing cleaning activity against soil and stains which contain an ester linkage, such as oils, fats, and greases. Proteases hydrolyze peptides and proteins, and thus are particularly useful in providing cleaning activity against proteinaceous soil and stains such as blood as well as other foreign materials containing an amide bond.

A preferred α-amylase is Termamyl, which is derived from *B. licheniformis*. Other useful α-amylases include Alphamyl, Asperzyme, Clarase, Mycolase, Mycozyme, Rapidase, Rhozyme, and Tenase. A preferred cellulase is Celluzyme. A preferred lipase is Lipolase. Other useful lipases include pancreatin. A preferred protease is Alcalase. Other preferred proteases include Esperase. The enzyme component generally comprises 0.1 wt. % up to about 5 wt. % and preferably 0.5 wt. % to 2 wt. %, by weight of the total composition.

7. Dyes and Colorants

Colorants and dyes, especially bluing agents, can be optionally added to the compositions of the present invention for visual appeal and performance impression. When colorants are used, they are used at extremely low levels to avoid fabric staining. Preferred colorants for use in the present compositions are highly water-soluble dyes, for example, LIQUITINT® dyes available from Milliken Chemical Company. Any dye can be used in the compositions of the present invention, but nonionic dyes are preferred to decrease interaction with dye transfer inhibitor. For many personal care products using the present invention, colorants are also added at extremely low levels. Color additives for products to be marketed in the United States are named in compliance with Title 21 of the U.S. Code of Federal Regulations.

8. Insect and Moth Repelling Agents

The composition of the present invention can optionally contain an effective amount of insect or moth repelling agents. Typical insect and moth repelling agents are pheromones, such as anti-aggregation pheromones, and other natural and/or synthetic ingredients. Preferred insect and moth repellent agents useful in the composition of the present invention are perfume ingredients, such as citronellol, citranellal, citral, linalool, cedar extract, geranium oil, sandalwood oil, 2-(diethylphenoxy)ethanol, 1-dodecene, and the like. Other examples of insect and/or moth repellents useful in the composition of the present invention are disclosed in U.S. Pat. Nos. 4,449,987; 4,693,890; 4,696,676; 4,933,371; 5,030,660; and 5,196,200; and in B. D. Mookherjee et al., "Semio Activity of Flavor and Fragrance Molecules on Various Insect Species", published in *Bioactive Volatile Compounds from Plants*, ASC Symposium Series 525, R. Teranishi, R. G. Buttery, and H. Sugisawa (eds.), 1993, pp. 35–48. All of these patents and publications are herein incorporated by reference in their entireties. When an insect and/or moth repellent is used it is typically present at a level of from about 0.005 wt. % to about 3 wt. % of the composition.

9. Polymeric Soil Release Agents

Soil release agents, usually polymers, are especially desirable additives at levels of from about 0.05 wt. % to about 5 wt. %, preferably from about 0.1 wt. % to about 4 wt. %, more preferably from about 0.2 wt. % to about 3 wt. %. Suitable soil release agents are disclosed in U.S. Pat. Nos. 4,702,857; 4,711,730; 4,713,194; 4,877,896; 4,956,447; and 4,749,596, all of these patents being herein incorporated by reference in their entireties.

Especially desirable optional ingredients are polymeric soil release agents comprising block copolymers of polyalkylene terephthalate and polyoxyethylene terephthalate, and block copolymers of polyalkylene terephthalate and polyethylene glycol. The polyalkylene terephthalate blocks preferably comprise ethylene and/or propylene groups. Many such soil release polymers are nonionic, for example, the nonionic soil release polymer is described in U.S. Pat. No. 4,849,257, which patent is herein incorporated by reference in its entirety.

The polymeric soil release agents useful in the present invention can include anionic and cationic polymeric soil release agents. Suitable anionic polymeric or oligomeric soil release agents are disclosed in U.S. Pat. No. 4,018,569, which patent is herein incorporated by reference in its entirety. Other suitable polymers are disclosed in U.S. Pat. No. 4,808,086, which patent is herein incorporated by reference in its entirety. Suitable cationic soil release polymers are described in U.S. Pat. No. 4,956,447, which patent has already been herein incorporated by reference.

10. Viscosity Control Agents

Viscosity control agents can be organic or inorganic in nature and may either lower or raise the viscosity of the formulation. Examples of organic viscosity modifiers (lowering) are aryl carboxylates and sulfonates (for example, benzoate, 2-hydroxybenzoate, 2-aminobenzoate, benzenesulfonate, 2-hydroxybenzenesulfonate, 2-aminobenzenesulfonate, and the like), fatty acids and esters, fatty alcohols, and water-miscible solvents such as short chain alcohols. Examples of inorganic viscosity control agents are water-soluble ionizable salts. A wide variety of ionizable salts can be used. Examples of suitable salts are the halides and acetates of ammonium ion and the group IA and IIA metals of the Periodic Table of the Elements, for example, calcium chloride, lithium chloride. sodium chloride, potassium chloride, magnesium chloride, ammonium chloride, sodium bromide, potassium bromide, calcium bromide, magnesium bromide, ammonium bromide, sodium iodide, potassium iodide, calcium iodide, magnesium iodide, ammonium iodide, sodium acetate, potassium acetate, or mixtures thereof. Calcium chloride is preferred. The ionizable salts are particularly useful during the process of mixing the ingredients to make the compositions herein, and later to obtain the desired viscosity. The amount of ionizable salts used depends on the amount of active ingredients used in the compositions and can be adjusted according to the desire of the formulator. Typical levels of salts used to control the composition viscosity are from 0 to about 10 wt. %, preferably from about 0.01 wt. % to about 6 wt. %, and most preferably from about 0.02 wt. % to about 3 wt. % of the composition.

Viscosity modifiers (raising) or thickening agents can be added to increase the ability of the compositions to stably suspend water-insoluble articles, for example, perfume microcapsules. Such materials include hydroxypropyl substituted guar gum (such as that available from Rhône-Poulenc Corporation under the tradename JAGUAR® HP200), polyethylene gycol (such as that available from Union Carbide Corporation under the tradename CARBOWAX® 20M), hydrophobic modified hydroxyethylcellulose (such as that available from the Aqualon Company under the tradename NATROSOL® Plus), and/or organophilic clays. These viscosity raisers (thickeners) are typically used at levels from about 0.5 wt. % to about 30 wt. %, preferably from about 1 wt. % to about 5 wt. %, more preferably from about 1.5 wt. % to about 3.5 wt. %, and most preferably from about 2 wt. % to about 3 wt. %, of the composition.

11. Pearlizing and Opacifying Agents

Examples of pearlizing or opacifying agents that can be added to the compositions of this invention include, but are not restricted to, glycol distearate, propylene glycol distearate, and glycol stearate. Some of these products are available from Witco Corporation under the KEMESTER® tradename.

12. Vitamins and Extracts

In personal care applications, vitamins and extracts are often used in the formulations thereof. Examples of vitamins that can be added to the compositions of this invention include, but are not restricted to, vitamins $A_1, A_2, B_1, B_2, B_6, B_{12}$, C, D, E, H, and K, the provitamins, salts, derivatives, and complexes thereof, and mixtures thereof. Examples of extracts that can be added to the compositions of this invention include, but are not restricted to, rosemary extract, carrot extract, Camelina sativa, camomile extract, egg yolk extract, elm extract, acacia extract, rose extract, lilac extract, licorice extract, lemon extract, orange extract, lime extract, linden extract, melon extract, peach extract, orchid extract, orris extract, and the like, and mixtures thereof.

13. Antioxidants

Examples of antioxidants that can be added to the compositions of this invention are propyl gallate, available from Eastman Chemical Products, Inc. under the tradenames TENOX® PG and TENOX® S-1, and dibutylated hydroxytoluene, available from UOP Inc. under the tradename SUSTANE® BHT.

14. Silicones

The present compositions can contain silicones to provide additional benefits, for example, in a fabric application they may provide ease of ironing and improved fabric absorbency. As used herein, the term "silicones" comprises cationic and amphoteric silicones, polysiloxanes, and polysiloxanes having hydrogen-bonding functional groups consisting of amino, carboxyl, hydroxyl, ether, polyether, aldehyde, ketone, amide, ester, and thiol groups. Such polysiloxanes include, but are not limited to, polyether-modified polysiloxanes, amino-modified polysiloxanes, epoxy-modified polysiloxanes, polyhydrido-modified polysiloxanes, phenol-derivative-modified polysiloxanes, ABA-type polysiloxanes,$[AB]_N$-type polysiloxanes, amino $[AB]_N$-type polysiloxanes, including those available from OSi Specialties, Inc. (a division of Witco Corporation), under the SILWET®, NUWET®, NUDRY™, NUSOFT™, MAGNASOFT® tradenames.

Suitable silicones may include polydimethylsiloxanes of viscosity of from about 100 centistokes (cs) to about 100,000 cs, preferably from about 200 cs to about 60,000 cs and/or silicone gums. These silicones can be used in emulsified form, which can be conveniently obtained directly from the suppliers. Examples of these preemulsified silicones are the 60% emulsion of polydimethylsiloxane (350 cs) sold by Dow Corning Corporation under the tradename DOW CORNING® 1157 Fluid and the 50% emulsion of polydimethylsiloxane (10,000 cs) sold by General Electric Company under the tradename GENERAL ELECTRIC® SM 2140 silicones. The optional silicone component can be used in an amount of from about 0.1 wt. % to about 6 wt. % of the composition.

Silicone foam suppressants can also be used. These are usually not emulsified and typically have viscosities of from about 100 cs to about 10,000 cs, preferably from about 200 cs to about 5,000 cs. Very low levels are used, typically from about 0.01% to about 1%, preferably from about 0.02% to about 0.5%. Another preferred foam suppressant is a silicone/silicate mixture, for example, Dow Corning's ANTIFOAM™ A.

15. Lubrication and Slip Additives

Compositions and formulations of the present invention can contain additives such as water, insoluble organics such as fatty acids, fatty esters, triglycerides, oils, alcohols, fatty alcohols, fatty amines and derivatives, amides, hydrocarbons, mineral oils, waxes, and the like, and mixtures thereof, as lubrication and slip agents.

16. Dye Transfer Inhibitors

Compositions and formulations of the present invention can contain ethoxylated amines, amphoterics, betaines, sulfosuccinates, sulfobetaines, polymers such as polyvinylpyrrolidone, and other ingredients that inhibit dye transfer.

Other optional ingredients include aloe, humectants, skin protectants, and feel modifiers. Suitable humectants include lactic acid and its salts, sugars, ethoxylated glycerin. ethoxylated lanolin, corn syrup, hydrolyzed starch hydrolysate, urea, and sorbitol. Suitable skin protectants include allantoin, kaolin, and zinc oxide. Suitable feel modifiers include corn starch, oat flour, talc, boron nitride, and cyclodextrin.

J. EXAMPLES

The following examples are but a few examples of more particular formulations embodying the compositions of the present invention. The following examples are provided for purposes of further description of the present invention and are not intended to limit the scope of that which is regarded as the invention.

1. Paper Softener and Debonding Formulations and Examples

These examples illustrate formulations of Inventive Ester Quats for use as softener/debonding agents, for example, in tissue or paper products. Application methods, papermaking and tissuemaking additives, and other additives are well known to those of skill in the art and are described, for example, in G. A. Smook, *Handbook for Pulp & Paper Technologists* (2 nd Edition) (Angus Wilde Pub. Inc., 1992), which is hereby incorporated by reference in its entirety to better describe the state of the art. Examples 1 to 3 are specific examples, while Example 4 presents a general softener/debonder formulation according to the present invention. Examples 1 to 3 are particularly easy to disperse in water.

EXAMPLE 1

Softening/Debonding Agent Formulation for Paper

| Component | Amount (wt. %) |
|---|---|
| Inventive Ester Quat 5455-64 | 80 |
| Propylene glycol | 5 |
| Nonionic surfactant such as an alkoxylated fatty acid (such as that available from Witco Corporation under the tradename AROSURF ® 8-190) | 15 |

EXAMPLE 2

Softening/Debonding Agent Formulation for Paper

| Component | Amount (wt. %) |
|---|---|
| Inventive Ester Quat 5455-112 | 80 |
| Propylene glycol | 5 |
| Nonionic surfactant such as an alkoxylated fatty acid (such as that available from Witco Corporation under the tradename AROSURF ® 8-190) | 15 |

EXAMPLE 3

Softening/Debonding Agent Formulation for Paper

| Component | Amount (wt. %) |
|---|---|
| Inventive Ester Quat 5398-53 | 80 |
| Propylene glycol | 5 |
| Nonionic surfactant such as an alkoxylated fatty acid (such as that available from Witco Corporation under the tradename AROSURF ® 8-190) | 15 |

In general, the softener/debonder formulation of the present invention would include the components set forth in Example 4 in the amounts shown.

EXAMPLE 4

General Softener/Debonder Concentrate Formulation

| | Amount (wt. %) | | |
|---|---|---|---|
| Component | typical | preferred | most preferred |
| Inventive Ester Quat | 10–100 | 30–100 | 60–100 |
| Propylene glycol | 0–30 | 0–20 | 0–10 |
| Polyethylene glycol | 0–30 | 0–20 | 0–10 |
| Nonionic surfactant such as alkoxylated fatty acid or alkoxylated nonionic surfactant | 0–80 | 0–60 | 0–40 |

In the following tests, the performance of certain Inventive Ester Quats of the present invention were compared to the performance of commercial products, for example, those available from Witco Corporation under the tradenames VARISOFT® 3690, AROSURF® PA801, AROSURF® 8-190, and ADOGEN® 66, and that available from Eka Nobel under the tradename BEROCELL 509® HA, at dosages corresponding to 1, 3, 5, and 8 lbs. (#) debonder/ton of fiber using various fiber furnish. The designations for each compound or formulation used and tested below and their respective identity or description are set forth as a legend in Table 1. Table 2 similarly identifies the various furnishes used in the testing below.

TABLE 2

Description of Furnishes Used in Testing

| Designation | Description |
|---|---|
| SW | Northern Softwood Kraft Fiber (various sources) |
| SW/RF | Blend of 60% Northern Softwood Kraft/40% Recycled Fiber (various sources) |
| SW/HW | 50 wt. % Northern Softwood Kraft Fiber/50 wt. % Eucalyptus Hardwood (various sources) |
| 30SW/70HW | 30 wt. % Northern Softwood Kraft Fiber/70 wt. % Eucalyptus Hardwood |
| CTMP/SW/HW | 25 wt. % chemical thermomechanical pulp (CTMP); 25 wt. % Northern Softwood Kraft; 50 wt. % Eucalyptus Hardwood (various sources) |

Standard preparation and test methods were employed to prepare handsheets and to conduct the comparative tests against AROSURF® PA-801, VARISOFT® 3690, and BEROCELL 509® HA; they are as follows: handsheet preparation (TAPPI test method T-205); dry tensile (TAPPI test method T-492); sorptive rate and capacity (TAPPI test method T-561); paper conditioning (TAPPI test method T-402); and grammage and thickness (TAPPI test method T-220). Softness was evaluated using paired comparison softness panels.

In each case, a dispersion of the appropriate formulation was prepared in water at 20–25° C. An aqueous slurry of selected fibers was treated with the dispersion of the respective formulation at dosages corresponding to 1, 3, 5, and 8 lbs. (#) debonder/ton of fiber. Tissue weight handsheets, approximately 60 g/m$^2$, were prepared according TAPPI test method T-205. The handsheets were equilibrated under conditions specified in TAPPI test method T402. The handsheets were tested for tensile and sorptive rate and capacity according to TAPPI test methods T-492 and T-561, respectively. The handsheets were tested for and grammage and thickness according to TAPPI test method T-220. The results presented in the following Tables demonstrate the performance of many debonders according to the present invention in comparison with commercial products on a variety of furnishes.

The results show that the Inventive Ester Quats are effective debonders and compare favorably in performance to industry standards. Indeed, the Inventive Ester Quats afford debonded tissue products with good absorbency rates and capacities and hand panels confirm that the formulations of the instant invention give better softness than ARO-SURF® PA-801 debonder. In addition, the Inventive Ester Quat formulations have low odor and each of the above formulations was easy to disperse in warm water. As with all of the Examples given, these examples are only exemplary and, although applied here to various fibers and fiber blends, they may be used with hardwood fiber, softwood fiber, recycled fiber, baggasse fibers, fluff pulp, and all natural papermaking fibers, or cellulosic fibers and blends thereof.

salt) was substantive, as evidenced by tensile reduction, and it improved absorbency, matching the commercial product ADOGEN® 66 in performance. The acid salt (5455-111A) was also a very effective debonder with extremely good absorbency properties, also matching the performance of the commercial product ADOGEN® 66. Debonders 5455-111A, 5455-111, and 5455-112 outperformed a commercial softener/debonder, BEROCELL 509® HA, in debonding and absorbency performance; and 5455-111 and 5455-111A outperformed VARISOFT® 3690 in absorbency. Although 5455-112 was a good debonder, the absorbency data shows it to be inferior which is inconsistent with the results with

TABLE SW-1

Testing Results for SW (Lot 1)

| Debonder used | Dosage (lbs./ton) | Tensile strength (kNm/kg) | Absorbency Rate from 0–5 sec. (g/g/sec) | Absorbency Capacity at 20 sec. (g $H_2O$/g fiber) | Density (g/cm$^3$) |
|---|---|---|---|---|---|
| Blank | 0 | 14.56 | 0.15 | 2.01 | 0.338 |
| VARISOFT ® | 1 | 11.89 | 0.14 | 1.88 | 0.337 |
| 3690 | 3 | 8.91 | 0.12 | 1.60 | 0.334 |
|  | 5 | 6.47 | 0.12 | 1.59 | 0.331 |
| BEROCELL | 1 | 13.16 | 0.15 | 1.96 | 0.354 |
| 509 ® HA | 3 | 10.39 | 0.12 | 1.52 | 0.340 |
|  | 5 | 8.93 | 0.11 | 1.42 | 0.334 |
| ADOGEN ® 66 | 1 | 12.79 | 0.14 | 1.99 | 0.339 |
|  | 3 | 13.56 | 0.14 | 1.78 | 0.334 |
|  | 5 | 11.48 | 0.14 | 1.78 | 0.329 |
| 5455-111 | 1 | 12.50 | 0.16 | 2.10 | 0.330 |
|  | 3 | 10.75 | 0.14 | 1.85 | 0.329 |
|  | 5 | 8.14 | 0.15 | 2.11 | 0.320 |
| 5455-111A | 1 | 11.66 | 0.15 | 1.96 | 0.331 |
|  | 3 | 8.92 | 0.17 | 2.12 | 0.330 |
|  | 5 | 6.20 | 0.15 | 1.93 | 0.322 |
| 5455-112 | 1 | 12.73 | 0.13 | 1.81 | 0.340 |
|  | 3 | 9.87 | 0.11 | 1.53 | 0.340 |
|  | 5 | 8.18 | 0.12 | 1.62 | 0.330 |

The testing results for SW (lot 1) set forth in Table SW-1 compares the canola/conla amine ethoxylate Inventive Ester Quats: the amine, the acid salt, and the DMS quaternized derivative with commercial debonding products. The results show that 5455-111 (used as just the fatty acid ester of amine ethoxylate without conversion to an ammonium 5455-111A on this fiber. Density typically decreased with increasing dosage of debonder.

TABLE SW-2

Testing Results for SW (Lot 2)

| Debonder used | Dosage (lbs./ton) | Tensile strength (kNm/kg) | Absorbency Rate from 0–5 sec. (g/g/sec) | Absorbency Capacity at 20 sec. (g $H_2O$/g fiber) | Density (g/cm$^3$) |
|---|---|---|---|---|---|
| Blank | 0 | 12.87 | 0.26 | 2.69 | 0.312 |
| AROSURF ® | 1 | 12.03 | 0.26 | 2.50 | 0.327 |
| PA-801 | 3 | 9.10 | 0.24 | 2.35 | 0.322 |
|  | 5 | 7.14 | 0.21 | 2.25 | 0.322 |
| 5326-198C | 1 | 12.28 | 0.22 | 2.40 | 0.326 |
|  | 3 | 9.75 | 0.20 | 2.34 | 0.328 |
|  | 5 | 8.61 | 0.17 | 2.13 | 0.328 |
| 5326-199D | 1 | 13.17 | 0.22 | 2.39 | 0.323 |
|  | 3 | 9.14 | 0.20 | 2.17 | 0.325 |
|  | 5 | 7.60 | 0.20 | 2.24 | 0.311 |
| 5326-199B | 1 | 13.20 | 0.21 | 2.35 | 0.340 |
|  | 3 | 9.68 | 0.19 | 2.10 | 0.340 |
|  | 5 | 8.10 | 0.19 | 2.03 | 0.332 |
| 5326-199A | 1 | 13.08 | 0.22 | 2.44 | 0.341 |
|  | 3 | 12.03 | 0.2 | 2.25 | 0.334 |
|  | 5 | 10.02 | 0.17 | 2.09 | 0.333 |

TABLE SW-3

Testing Results for SW (Lot 3)

| Debonder used | Dosage (lbs./ton) | Tensile strength (kNm/kg) | Absorbency Rate from 0–5 sec. (g/g/sec) | Absorbency Capacity at 20 sec. (g $H_2O$/g fiber) | Density (g/cm$^3$) |
|---|---|---|---|---|---|
| Blank | 0 | 15.28 | 0.19 | 2.08 | 0.350 |
| AROSURF ® PA-801 | 1 | 13.61 | 0.16 | 1.80 | 0.336 |
| | 3 | 10.05 | NA | NA | 0.338 |
| | 5 | 7.67 | 0.13 | 1.33 | 0.329 |
| 5326-198C | 1 | 12.53 | 0.16 | 1.71 | 0.339 |
| | 3 | 9.22 | 0.13 | 1.44 | 0.332 |
| | 5 | 7.00 | 0.14 | 1.52 | 0.331 |
| 5326-199A1 | 1 | 12.48 | 0.16 | 1.84 | 0.332 |
| | 3 | 9.57 | 0.15 | 1.71 | 0.333 |
| | 5 | 7.05 | 0.15 | 1.73 | 0.332 |

The testing results for SW (lot 2) and SW (lot 3) set forth in Tables SW-2 and SW-3, respectively, compares Inventive Ester Quats formulations that are formulated similarly to AROSURF® PA-801. The results show that the formulated products according to the instant invention afford very effective debonders as evidenced by the tensile reductions which are similar to the commercial product AROSURF® PA-801. In fact, all of the formulated products according to the instant invention provide for very absorbent products when they are applied. What is surprising is that the Inventive Ester Quat esters of the amine ethoxylates exhibit good debonding and provide absorbencies superior to those treated with AROSURF® PA-801. The differences in performance between SW (lot 2) and SW (lot 3) set forth in Tables SW-2 and SW-3 may be due to the variations between different furnishes in lot 2 and lot 3.

Quats have comparable performance to amine Inventive Ester Quats and commercial debonding products and provide satisfactory absorbency. The results show that the quaternary ammonium esters of VARONIC® T-410 (a diamine) are effective debonders as evidenced by the decrease in tensile with increasing dosage. These materials compare quite well with the performance of the commercial product VARISOFT® 3690. In addition, the handsheets are absorbent after treatment with the debonders of the instant invention.

TABLE SW-4

Testing Results for SW (Lot 4)

| Debonder used | Dosage (lbs./ton) | Tensile strength (kNm/kg) | Absorbency Rate from 0–5 sec. (g/g/sec) | Absorbency Capacity at 20 sec. (g $H_2O$/g fiber) | Density (g/cm$^3$) |
|---|---|---|---|---|---|
| Blank | 0 | 13.54 | 0.17 | 1.89 | 0.339 |
| VARISOFT ® 3690 | 3 | 8.86 | 0.16 | 1.74 | 0.333 |
| | 5 | 6.40 | 0.16 | 1.67 | 0.330 |
| | 8 | 5.67 | 0.15 | 1.70 | 0.324 |
| 5398-1 | 3 | 8.10 | 0.16 | 1.71 | 0.336 |
| | 5 | 6.66 | 0.15 | 1.62 | 0.322 |
| | 8 | 6.05 | 0.15 | 1.61 | 0.327 |
| 5397-106A | 3 | 7.12 | 0.16 | 1.71 | 0.324 |
| | 5 | 6.45 | 0.14 | 1.51 | 0.326 |
| | 8 | 5.72 | 0.13 | 1.38 | 0.327 |
| 5455-82 | 3 | 9.10 | 0.16 | 1.74 | 0.320 |
| | 5 | 7.34 | 0.16 | 1.80 | 0.318 |
| | 8 | 6.13 | 0.15 | 1.67 | 0.324 |

The testing results for SW (lot 4) set forth in Table SW-4 compares and demonstrates that the diamine Inventive Ester

TABLE SW-5

Testing Results for SW (Lot 5)

| Debonder used | Dosage (lbs./ton) | Tensile strength (kNm/kg) | Absorbency Rate from 0–5 sec. (g/g/sec) | Absorbency Capacity at 20 sec. (g $H_2O$/g fiber) | Density (g/cm$^3$) |
|---|---|---|---|---|---|
| Blank | 0 | 16.16 | 0.18 | 1.94 | 0.341 |

TABLE SW-5-continued

Testing Results for SW (Lot 5)

| Debonder used | Dosage (lbs./ton) | Tensile strength (kNm/kg) | Absorbency Rate from 0–5 sec. (g/g/sec) | Absorbency Capacity at 20 sec. (g H$_2$O/g fiber) | Density (g/cm$^3$) |
|---|---|---|---|---|---|
| AROSURF ® PA-801 | 1 | 13.84 | 0.15 | 1.60 | 0.341 |
|  | 3 | 9.99 | 0.15 | 1.61 | 0.338 |
|  | 5 | 8.80 | 0.14 | 1.50 | 0.336 |
| 5398-5 | 1 | 12.09 | 0.16 | 1.56 | 0.344 |
|  | 3 | 10.18 | 0.13 | 1.39 | 0.344 |
|  | 5 | 8.40 | 0.14 | 1.50 | 0.342 |
| 5398-119 | 1 | 14.15 | 0.14 | 1.51 | 0.352 |
|  | 3 | 10.58 | 0.14 | 1.52 | 0.343 |
|  | 5 | 8.37 | 0.15 | 1.47 | 0.341 |
| 5398-120 | 1 | 12.75 | 0.15 | 1.63 | 0.349 |
|  | 3 | 9.48 | 0.14 | 1.55 | 0.344 |
|  | 5 | 7.63 | 0.17 | 1.78 | 0.337 |
| 5398-121 | 1 | 12.69 | 0.15 | 1.65 | 0.354 |
|  | 3 | 8.61 | 0.16 | 1.60 | 0.338 |
|  | 5 | 6.96 | 0.13 | 1.54 | 0.332 |
| 5455-64 | 1 | 14.16 | 0.17 | 1.76 | 0.347 |
|  | 3 | 9.96 | 0.15 | 1.51 | 0.349 |
|  | 5 | 8.32 | 0.13 | 1.34 | 0.344 |

The testing results for SW (lot 5) set forth in Table SW-5 compares the performance of certain tallow/cocoamine ethoxylate Inventive Ester Quats, certain tallow/tallowamine ethoxylate Inventive Ester Quats, and commercial debonders. The results show that tallow/tallowamine ethoxylate Inventive Ester Quats (prepared from ADOGEN® 170) and tallow/cocoamine ethoxylate Inventive Ester Quats (prepared from ADOGEN® 160) are effective debonders as demonstrated by the decreasing tensile strength reduction with increasing dosage. Furthermore, the products based on ADOGEN® 160, 5398-120 and 5398-121, also afford extremely absorbent material: testing these at 100% actives gave better absorbencies than fiber treated with the commercial debonder product AROSURF® PA-801 that contains nonionics to improve absorbency. However, 5398-5, based on ADOGEN® 170, is also an effective debonder which also affords absorbent product.

The testing results for SW (lot 6) set forth in Table SW-6 compares the performance of tallow/tallow amine ethoxylate Inventive Ester Quats (5398-122 and 5398-129), canola/tallow amime ethoxylate Inventive Ester Quats (5398-107 and 5398-127), and a behenic/tallowamine ethoxylate Inventive Ester Quat (5398-128). The test was performed to demonstrate that the Inventive Ester Quats were not sensitive to the use of different synthesis starting materials to make the same products (that is, the pairs 5398-122/129 and 5398-107/127 were each made using fatty acids from different commercial sources) and that the results were consistent and reproducible from lot to lot. The results show that the performance was similar for each respective pair of Inventive Ester Quats and each are effective debonders as demonstrated by the increasing tensile strength reduction with increasing dosage. Furthermore, the behenic/tallowamine ethoxylate Inventive Ester Quat (5398-128)

TABLE SW-6

Testing Results for SW (Lot 6)

| Debonder used | Dosage (lbs./ton) | Tensile strength (kNm/kg) | Absorbency Rate from 0–5 sec. (g/g/sec) | Absorbency Capacity at 20 sec. (g H$_2$O/g fiber) | Density (g/cm$^3$) |
|---|---|---|---|---|---|
| Blank | 0 | 12.97 | 0.21 | 2.23 | 0.316 |
| 5398-127 | 3 | 8.37 | 0.17 | 1.95 | 0.321 |
|  | 5 | 6.81 | 0.18 | 2.07 | 0.310 |
|  | 8 | 5.25 | 0.18 | 2.13 | 0.304 |
| 5398-107 | 3 | 7.99 | 0.18 | 1.96 | 0.319 |
|  | 5 | 6.93 | 0.19 | 2.03 | 0.317 |
|  | 8 | 5.51 | 0.18 | 2.19 | 0.309 |
| 5398-122 | 3 | 7.73 | 0.18 | 2.07 | 0.311 |
|  | 5 | 6.72 | 0.17 | 1.90 | 0.321 |
|  | 8 | 5.76 | 0.17 | 1.88 | 0.314 |
| 5398-129 | 3 | 8.51 | 0.17 | 2.02 | 0.313 |
|  | 5 | 6.71 | N/A | 2.07 | 0.284 |
|  | 8 | 5.91 | 0.18 | 2.03 | 0.309 |
| 5398-128 | 3 | 6.86 | 0.13 | 1.45 | 0.320 |
|  | 5 | 5.51 | 0.14 | 1.47 | 0.318 |
|  | 8 | 5.07 | 0.14 | 1.35 | 0.320 | also was an effective debonder, although the absorbencies were not as impressive as the other Inventive Ester Quats, as would be expected because of the behenic fatty acid moiety is saturated and has a longer chain length than either canola or tallow fatty acid, and therefore provides a more hydrophobic molecule.

TABLE SW-7

Testing Results for SW (Lot 7)

| Debonder used | Dosage (lbs./ton) | Tensile strength (kNm/kg) | Absorbency Rate from 0–5 sec. (g/g/sec) | Absorbency Capacity at 20 sec. (g $H_2O$/g fiber) | Density (g/cm$^3$) |
|---|---|---|---|---|---|
| Blank | 0 | 16.66 | 0.17 | 1.96 | 0.346 |
| AROSURF ® PA-801 | 3 | 8.81 | 0.15 | 1.71 | 0.340 |
|  | 8 | 5.76 | 0.14 | 1.73 | 0.348 |
| 5385-152A | 3 | 9.34 | 0.16 | 1.77 | 0.343 |
|  | 8 | 6.01 | 0.13 | 1.73 | 0.332 |
| 5385-152B | 3 | 9.82 | 0.15 | 1.75 | 0.349 |
|  | 8 | 6.62 | 0.15 | 1.74 | 0.338 |
| 5455-119 | 3 | 10.84 | 0.13 | 1.57 | 0.346 |
|  | 5 | 7.98 | 0.12 | 1.43 | 0.351 |
|  | 8 | 5.90 | 0.12 | 1.28 | 0.343 |
| 5385-153A | 3 | 10.60 | 0.14 | 1.74 | 0.350 |
|  | 5 | 8.03 | 0.14 | 1.67 | 0.345 |
|  | 8 | 7.35 | 0.12 | 1.43 | 0.350 |
| 5385-153B | 3 | 10.03 | 0.16 | 1.86 | 0.347 |
|  | 5 | 7.85 | 0.14 | 1.63 | 0.332 |
|  | 8 | 7.04 | 0.15 | 1.60 | 0.341 |
| 5385-153C | 3 | 8.79 | 0.14 | 1.63 | 0.339 |
|  | 5 | 7.18 | 0.14 | 1.57 | 0.334 |
|  | 8 | 6.03 | 0.14 | 1.63 | 0.342 |

The testing results for SW (lot 7) set forth in Table SW-7 compares the performance of certain Inventive Ester Quat formulations made from HMDA quats (compounds of structural formulas (xxiii) above) and Inventive Ester Quats formulated with VARISOFT® 3690 in comparison to commercial debonder AROSURF® PA-801. The results show that Inventive Ester Quat formulations performed acceptably, having a similar performance to the commercial debonder product. Formulating 5398-1 with HMDA ester quat was found to improve absorbency and in the case of 5385-153C, the debonding performance was improved.

TABLE SW-8

Testing Results for SW (Lot 8)

| Debonder used | Dosage (lbs./ton) | Tensile strength (kNm/kg) | Absorbency Rate from 0–5 sec. (g/g/sec) | Absorbency Capacity at 20 sec. (g$H_2O$/ g fiber) | Density (g/cm$^3$) |
|---|---|---|---|---|---|
| Blank | 0 | 14.67 | 0.19 | 2.40 | 0.311 |
| VARISOFT ® 3690 | 3 | 8.80 | 0.14 | 1.68 | 0.336 |
|  | 5 | 7.46 | 0.13 | 1.57 | 0.329 |
|  | 8 | 5.01 | 0.15 | 1.72 | 0.318 |
| 5455-111 | 3 | 9.40 | 0.18 | 2.10 | 0.310 |
|  | 8 | 4.11 | 0.17 | 2.08 | 0.283 |
| 5455-111A | 3 | 7.94 | 0.18 | 2.21 | 0.311 |
|  | 5 | 5.77 | 0.18 | 2.21 | 0.309 |
|  | 8 | 4.42 | 0.17 | 2.12 | 0.303 |
| 5455-112 | 3 | 8.42 | 0.16 | 1.95 | 0.324 |
|  | 8 | 5.95 | 0.16 | 1.99 | 0.311 |
| 5455-158 | 3 | 8.00 | 0.20 | 2.37 | 0.311 |
|  | 5 | 6.62 | 0.20 | 2.41 | 0.310 |
|  | 8 | 3.94 | 0.20 | 2.32 | 0.296 |
| 5455-158A | 3 | 7.97 | 0.20 | 2.32 | 0.316 |
|  | 5 | 6.10 | 0.18 | 2.12 | 0.312 |
|  | 8 | 4.39 | 0.19 | 2.30 | 0.297 |
| 5455-159 | 3 | 8.84 | 0.20 | 2.23 | 0.324 |
|  | 8 | 4.70 | 0.15 | 1.96 | 0.311 |

The testing results for SW (lot 8) set forth in Table SW-8 compares the performance of certain Inventive Ester Quat series which differ by the degree of esterification: 5455-111/111A/112 are mono esters and 5455-158/158A/159 are 1.5 esters. The esters of the amine ethoxylates (5455-111 and 5455-158) were surprisingly effective debonders which were more absorbent than the standard VARISOFT® 3690. In addition, the acid salts (5455-111A and 54555-158A) were stronger debonders than VARISOFT® 3690 and produced a more absorbent product. The DMS salts (5455-112 and 5455-159) were effective debonders and produced a more absorbent product than VARISOFT® 3690 on this fiber. The results also show that the additional fatty ester content did not affect absorbency (but softening profiles would be improved); in general, the increased fatty ester content also afforded slightly better debonding.

TABLE SW-9

Testing Results for SW (Lot 9)

| | | | Ab- sorbency | Ab- sorbency |

| Debonder used | Dosage (lbs./ton) | Tensile strength (kNm/kg) | Rate from 0–5 sec. (g/g/sec) | Capacity at 20 sec. (gH$_2$O/ g fiber) | Density (g/cm$^3$) |
|---|---|---|---|---|---|
| Blank 1 | 0 | 24.84 | 0.36 | 3.92 | 0.27 |
| Blank 2 | 0 | 27.59 | 0.34 | 3.71 | 0.28 |
| Blank 3 | 0 | 28.50 | 0.30 | 3.52 | 0.29 |
| VARISOFT® 3690 | 1 | 24.17 | 0.17 | 2.29 | 0.29 |
|  | 3 | 17.85 | 0.16 | 2.15 | 0.28 |
|  | 5 | 14.97 | 0.16 | 2.15 | 0.28 |
| 5398-21 | 1 | 23.95 | 0.24 | 2.80 | 0.27 |
|  | 3 | 18.53 | 0.20 | 2.61 | 0.27 |
|  | 5 | 15.50 | 0.21 | 2.69 | 0.27 |
| 5398-7 | 1 | 23.81 | 0.26 | 3.11 | 0.27 |
|  | 3 | 21.52 | 0.22 | 2.95 | 0.26 |
|  | 5 | 21.45 | 0.21 | 3.05 | 0.26 |
| 5398-5 | 1 | 21.77 | 0.22 | 3.19 | 0.27 |
|  | 3 | 16.82 | 0.25 | 3.48 | 0.26 |
|  | 5 | 12.96 | 0.27 | 3.64 | 0.26 |
| 5398-1 | 1 | 22.85 | 0.26 | 3.46 | 0.28 |
|  | 3 | 17.07 | 0.31 | 3.83 | 0.27 |
|  | 5 | 15.76 | 0.33 | 4.05 | 0.27 |
| 5398-53 | 1 | 21.03 | 0.26 | 3.63 | 0.27 |
|  | 3 | 14.27 | 0.34 | 3.96 | 0.27 |
|  | 5 | 12.40 | 0.41 | 4.43 | 0.27 |
| 5398-100 | 1 | 24.26 | 0.28 | 3.57 | 0.29 |
|  | 3 | 18.24 | 0.36 | 4.46 | 0.29 |
|  | 5 | 16.09 | 0.17 | 2.19 | 0.29 |

The testing results for SW (lot 9) set forth in Table SW-9 compares the effect of the degree of ethoxylation on the performance of homologous Inventive Ester Quats, the effect of the degree of esterification on the performance of homologous Inventive Ester Quats, and the consistency in performance between Inventive Ester Quats made by different methods. The results show that several of the tested materials are extremely effective debonders, and in many cases their performance determined by dry tensile index is superior to the commercial product VARISOFT® 3690. In addition, several of the tested candidates actually showed an increase in absorbency rate and capacity with increasing debonder dosage, which is surprising since absorbency usually declines or levels of with increasing dosage. However, the results show that in some instances, absorbency capacity was higher for a treated material than the capacity for the blank (control). The apparent trend is that materials derived from VARONIC® T-215 such as 5398-1 are more absorbent that materials derived from VARONIC® T-210 such as 5398-21, which is probably due to the increased EO content. The higher the esterification, the better the debonding. The quaternized amine ethoxylate 5398-7 proved to be a very ineffective debonder; only when the amine ethoxylate is converted into an ester does one observe effective debonding. Other than VARISORT® 3690, the least absorbent material was 5397-100 which had the lowest degree of ethoxylation for the tallow derivatives presented in Table SW-9.

TABLE SW-10

Testing Results for SW (Lot 10)

| Debonder used | Dosage (lbs./ton) | Tensile strength (kNm/kg) | Absorbency Rate from 0–5 sec. (g/g/sec) | Absorbency Capacity at 20 sec. (gH$_2$O/ g fiber) | Density (g/cm$^3$) |
|---|---|---|---|---|---|
| Blank | 0 | 13.87 | 0.18 | 2.32 | 0.328 |
| VARISOFT® 3690 | 3 | 9.00 | 0.16 | 1.84 | 0.317 |
|  | 5 | 7.31 | 0.14 | 1.73 | 0.318 |
|  | 8 | 5.10 | 0.14 | 1.73 | 0.310 |
| 5398-127 | 3 | 8.58 | 0.18 | 2.20 | 0.322 |
|  | 5 | 6.73 | 0.19 | 2.32 | 0.317 |
|  | 8 | 5.76 | 0.18 | 2.20 | 0.320 |
| 5455-64 | 3 | 8.29 | 0.16 | 1.82 | 0.319 |
|  | 5 | 6.81 | 0.16 | 1.88 | 0.323 |
|  | 8 | 5.54 | 0.17 | 2.06 | 0.317 |
| 5455-80 | 3 | 9.54 | 0.16 | 1.83 | 0.315 |
|  | 5 | 7.98 | 0.16 | 1.77 | 0.320 |
|  | 8 | 5.00 | 0.15 | 1.70 | 0.307 |

The testing results for SW (lot 10) set forth in Table SW-10 compares the performance of certain homologous canola diester Inventive Ester Quats with various degrees of alkoxylation. The general trend is that increasing degrees of ethoxylation improve absorbency.

TABLE SW-11

Testing Results for SW (Lot 11)

| Debonder used | Dosage (lbs./ton) | Tensile strength (kNm/kg) | Absorbency Rate from 0–5 sec. (g/g/sec) | Absorbency Capacity at 20 sec. (gH$_2$O/ g fiber) |
|---|---|---|---|---|
| Blank | 0 | 28.79 | 0.19 | 2.58 |
| AROSURF® PA-801 | 1 | 25.35 | 0.17 | 2.20 |
|  | 3 | 19.41 | 0.15 | 1.98 |
|  | 5 | 15.33 | 0.15 | 2.04 |
| 5326-199A | 1 | 27.60 | 0.19 | 2.34 |
|  | 3 | 21.02 | 0.17 | 2.27 |
|  | 5 | 16.64 | 0.17 | 2.05 |
| 5326-199A1 | 1 | 26.67 | 0.17 | 2.39 |
|  | 3 | 19.55 | 0.15 | 2.06 |
|  | 5 | 14.77 | 0.16 | 2.07 |
| 5326-199B | 1 | 26.80 | 0.16 | 2.29 |
|  | 3 | 19.60 | 0.14 | 2.06 |
|  | 5 | 15.44 | 0.14 | 1.96 |

The testing results for SW (lot 11) set forth in Table SW-11 compares the performance of formulations containing nonionic additives with a particular Inventive Ester Quat (the free amine, the acid salt thereof, and the quaternized derivative thereof) in comparison with the commercial product AROSURF® PA-801. All of these compounds are effective debonders comparing favorably with AROSURF® PA-801. What is particularly surprising is the effectiveness of the Inventive Ester Quat amine as compared to the Inventive Ester Quat acid and quaternized derivatives.

TABLE SW-12

Testing Results for SW (Lot 12)

| Debonder used | Dosage (lbs./ton) | Tensile strength (kNm/kg) | Absorbency Rate from 0–5 sec. (g/g/sec) | Absorbency Capacity at 20 sec. ($gH_2O$/g fiber) | Density ($g/cm^3$) |
|---|---|---|---|---|---|
| Blank | 0 | 16.19 | 0.22 | 2.53 | 0.326 |
| AROSURF® PA-801 | 3 | 9.07 | 0.15 | 1.61 | 0.317 |
|  | 5 | 7.00 | 0.15 | 1.68 | 0.307 |
|  | 8 | 5.01 | 0.16 | 1.93 | 0.301 |
| 5455-176 | 3 | 10.65 | 0.16 | 1.93 | 0.315 |
|  | 5 | 6.76 | 0.19 | 2.36 | 0.310 |
|  | 8 | 5.47 | 0.18 | 2.17 | 0.303 |
| 5455-64 | 3 | 8.69 | 0.18 | 2.03 | 0.317 |
|  | 5 | 6.11 | 0.17 | 2.10 | 0.306 |
|  | 8 | 4.98 | 0.15 | 1.83 | 0.306 |

The testing results for SW (lot 12) set forth in Table SW-12 shows the performance of alkoxylated derivatives of Inventive Ester Quats, in particular, propoxylated and ethoxylated derivatives such as ADOGEN® 170+2 PO+10 EO. It can be seen that 5455-176, which differs from 5455-64 by the addition of 2 moles of PO, exhibited similar performance in terms of debonding and absorbency. In short, the presence of the PO was not detrimental to performance.

TABLE SW-13

Testing Results for SW (Lot 13)

| Debonder used | Dosage (lbs./ton) | Tensile strength (kNm/kg) | Absorbency Rate from 0–5 sec. (g/g/sec) | Absorbency Capacity at 20 sec. ($gH_2O$/g fiber) |
|---|---|---|---|---|
| Blank |  | 25.52 | 0.20 | 2.82 |
| AROSURF® PA-801 | 1 | 20.94 | 0.20 | 2.63 |
|  | 3 | 15.05 | 0.20 | 2.63 |
|  | 5 | 12.51 | 0.23 | 2.91 |
| BLEND 1 | 1 | 19.00 | 0.24 | 3.11 |
|  | 3 | 14.20 | 0.22 | 2.88 |
|  | 5 | 12.60 | 0.20 | 2.68 |
| BLEND 22 | 1 | 21.57 | 0.21 | 2.67 |
|  | 3 | 17.33 | 0.24 | 3.14 |
|  | 5 | 13.28 | 0.25 | 3.43 |
| BLEND 25 | 1 | 23.03 | 0.20 | 2.64 |
|  | 3 | 15.7 | 0.26 | 3.30 |
|  | 5 | 13.06 | 0.28 | 3.55 |
| BLEND 32 | 1 | 19.73 | 0.23 | 3.27 |
|  | 3 | 14.73 | 0.26 | 3.15 |
|  | 5 | 11.42 | 0.22 | 2.98 |
| BLEND 34 | 1 | 20.66 | 0.22 | 2.83 |
|  | 3 | 14.23 | 0.28 | 3.18 |
|  | 5 | 11.00 | 0.26 | 3.24 |

The testing results for SW (lot 13) set forth in Table SW-13 provides examples of formulations of Inventive Ester Quats with HMDA or imidazolinium quats. Several of the formulations exhibit debonding properties comparable or better than a commercial product AROSURF® PA-801, with superior absorbency performance.

TABLE SW/RF-1

Testing Results for SW/RF (Lot 1)

| Debonder used | Dosage (lbs./ton) | Tensile strength (kNm/kg) | Absorbency Rate from 0–5 sec. (g/g/sec) | Absorbency Capacity at 20 sec. ($gH_2O$/g fiber) | Density ($g/cm^3$) |
|---|---|---|---|---|---|
| Blank | 0 | 15.80 | 0.15 | 2.07 | 0.341 |
| VARISOFT® 3690 | 1 | 14.57 | 0.12 | 1.65 | 0.342 |
|  | 3 | 10.96 | 0.13 | 1.73 | 0.342 |
|  | 5 | 8.62 | 0.12 | 1.78 | 0.340 |
| BEROCELL 509® HA | 1 | 14.45 | 0.16 | 2.01 | 0.327 |
|  | 3 | 12.66 | 0.13 | 1.66 | 0.328 |
|  | 5 | 10.37 | 0.10 | 1.23 | 0.335 |
| ADOGEN® 66 | 1 | 14.84 | 0.14 | 1.84 | 0.333 |
|  | 3 | 13.74 | 0.14 | 1.81 | 0.335 |
|  | 5 | 13.31 | 0.14 | 1.78 | 0.337 |
| 5455-111 | 1 | 15.26 | 0.16 | 2.00 | 0.344 |
|  | 3 | 14.88 | 0.13 | 1.80 | 0.347 |
|  | 5 | 13.62 | 0.13 | 1.75 | 0.342 |
| 5455-111A | 1 | 15.67 | 0.15 | 2.00 | 0.336 |
|  | 3 | 14.5i | 0.13 | 1.80 | 0.341 |
|  | 5 | 11.44 | 0.12 | 1.74 | 0.338 |
| 5455-112 | 1 | 12.86 | 0.13 | 1.82 | 0.337 |
|  | 3 | 11.15 | 0.13 | 1.73 | 0.339 |
|  | 5 | 9.17 | O.15 | 1.90 | 0.332 |

The testing results for SW/RF (lot 1) set forth in Table SW/RF-1 compares the performance of a particular Inventive Ester Quat, the free amine, the acid salt thereof, and the quaternized derivative thereof against two commercial softener/debonders. All of these compounds are effective debonders comparing favorably with the commercial products. What is particularly surprising is the effectiveness of the amine as compared to the acid and quaternized derivatives. The results also reveal that ADOGEN® 66, a quat of an amine ethoxylate, was a very poor debonder, again confirming that the ethoxylate chain requires esterification for effective debonding performance.

TABLE SW/RF-2

Testing Results for SW/RF (Lot 2)

| Debonder used | Dosage (lbs./ton) | Tensile strength (kNm/kg) | Absorbency Rate from 0–5 sec. (g/g/sec) | Absorbency Capacity at 20 sec. ($gH_2O$/g fiber) | Density ($g/cm^3$) |
|---|---|---|---|---|---|
| Blank | 0 | 15.33 | 0.23 | 2.55 | 0.342 |
| AROSURF® PA-801 | 1 | 15.78 | 0.18 | 2.07 | 0.340 |
|  | 3 | 12.93 | 0.15 | 1.64 | 0.349 |
|  | 5 | 9.79 | 0.14 | 1.53 | 0.337 |
| 5326-198C | 1 | 14.66 | 0.18 | 2.12 | 0.343 |
|  | 3 | 12.62 | 0.16 | 1.87 | 0.349 |
|  | 5 | 9.26 | 0.14 | 1.66 | 0.341 |
| 5326-199D | 1 | 15.00 | 0.18 | 2.23 | 0.344 |
|  | 3 | 12.81 | 0.15 | 1.77 | 0.344 |
|  | 5 | 9.73 | 0.14 | 1.69 | 0.345 |
| 5326-199B | 1 | 15.76 | 0.18 | 2.16 | 0.344 |
|  | 3 | 13.04 | 0.15 | 1.73 | 0.350 |
|  | 5 | 10.37 | 0.14 | 1.59 | 0.340 |
| 5326-199A | 1 | 14.86 | 0.18 | 2.13 | 0.341 |
|  | 3 | 14.70 | 0.17 | 2.11 | 0.341 |
|  | 5 | 13.62 | 0.15 | 1.92 | 0.344 |

TABLE SW/RF-3

Testing Results for SW/RF (Lot 3)

| Debonder used | Dosage (lbs./ton) | Tensile strength (kNm/kg) | Absorbency Rate from 0–5 sec. (g/g/sec) | Absorbency Capacity at 20 sec. (gH$_2$O/ g fiber) | Density (g/cm$^3$) |
|---|---|---|---|---|---|
| Blank | 0 | 17.23 | 0.16 | 1.72 | 0.34 |
| AROSURF ® PA-801 | 1 | 15.16 | 0.16 | 1.74 | 0.34 |
|  | 3 | 12.64 | 0.15 | 1.50 | 0.35 |
|  | 5 | 9.15 | 0.15 | 1.51 | 0.35 |
| 5326-198C | 1 | 14.01 | 0.16 | 1.66 | 0.34 |
|  | 3 | 11.20 | 0.13 | 1.43 | 0.35 |
|  | 5 | 8.83 | 0.13 | 1.42 | 0.34 |
| 5326-199A | 1 | 17.55 | 0.17 | 1.89 | 0.35 |
|  | 3 | 15.69 | 0.16 | 1.72 | 0.35 |
|  | 5 | 13.33 | 0.16 | 1.70 | 0.35 |

The testing results for SW/RF (lot 2) and SW/RF (lot 3) set forth in Tables SW/RF-2 and SW/RF-3, respectively, compares formulations of Inventive Ester Quats with non-ionics. Such Inventive Ester Quat formulations afforded similar debonding and absorbency performance against AROSURF® PA-801. The ester of the amine ethoxylate formulation 5326-199A was a surprising formulation as debonding was evidenced as well as excellent absorbency properties. This fiber blend responded differently to the formulations with the quats of the amine ethoxylate esters than the softwood furnish (SW lot 4)). The results show that 5326-198C was a good debonder, but it exhibited poor absorbency performance, while 5326-199A provided very good absorbency, but was a very poor debonder.

TABLE SW/RF-4

Testing Results for SW/RF (Lot 4)

| Debonder used | Dosage (lbs./ton) | Tensile strength (kNm/kg) | Absorbency Rate from 0–5 sec. (g/g/sec) | Absorbency Capacity at 20 sec. (gH$_2$O/ g fiber) | Density (g/cm$^3$) |
|---|---|---|---|---|---|
| Blank 1 | 0 | 32.48 | 0.18 | 2.32 | 0.29 |
| Blank 2 | 0 | 32.06 | 0.21 | 2.79 | 0.28 |
| Blank 3 | 0 | 30.48 | 0.19 | 2.69 | 0.28 |
| Blank 4 | 0 | 30.94 | 0.20 | 2.83 | 0.29 |
| AROSURFr PA-801 | 1 | 27.62 | 0.18 | 2.21 | 0.28 |
|  | 3 | 22.03 | 0.16 | 2.02 | 0.28 |
|  | 5 | 18.21 | 0.12 | 2.01 | 0.27 |
| 5398-21 | 1 | 26.10 | 0.21 | 2.83 | 0.27 |
|  | 3 | 20.53 | 0.19 | 2.43 | 0.27 |
|  | 5 | 17.42 | 0.19 | 2.50 | 0.26 |
| 5398-7 | 1 | 28.69 | 0.20 | 2.52 | 0.26 |
|  | 3 | 26.90 | 0.16 | 2.35 | 0.28 |
|  | 5 | 26.49 | 0.17 | 2.47 | 0.27 |
| 5398-5 | 1 | 24.84 | 0.18 | 2.61 | 0.27 |
|  | 3 | 18.98 | 0.19 | 2.54 | 0.28 |
|  | 5 | 15.25 | 0.18 | 2.46 | 0.27 |
| 5398-1 | 1 | 24.51 | 0.18 | 2.61 | 0.27 |
|  | 3 | 20.15 | 0.17 | 2.34 | 0.27 |
|  | 5 | 18.81 | 0.22 | 2.89 | 0.27 |
| 5398-53 | 1 | 26.00 | 0.19 | 2.47 | 0.27 |
|  | 3 | 19.65 | 0.21 | 2.66 | 0.27 |
|  | 5 | 14.53 | 0.21 | 2.85 | 0.26 |
| 5398-100 | 1 | 23.85 | 0.16 | 2.23 | 0.27 |
|  | 3 | 19.71 | 0.15 | 2.00 | 0.27 |
|  | 5 | 16.45 | 0.15 | 2.01 | 0.27 |

The testing results for SW/RF (lot 4) set forth in Table SW/RF-4 compares the effect of the degree of ethoxylation on the performance of homologous Inventive Ester Quats, the effect of the degree of esterification on the performance of homologous Inventive Ester Quats, and the consistency in performance between Inventive Ester Quats made by different methods. The results show that several of the tested materials are extremely effective debonders, and in many cases their performance determined by dry tensile index is superior to the commercial product AROSURF® PA-801. In addition, several of the tested candidates actually showed an increase in absorbency rate and capacity with increasing debonder dosage, which is surprising since absorbency usually declines or levels off with increasing dosage. However, the results show that in some instances, absorbency capacity was higher for a treated material than the capacity for the blank (control). all of the quat esters of amine ethoxylates AROSURF® PA-801 with this furnish. The apparent trend is that materials derived from VARONIC® T-215 such as 5398-1 are more absorbent that materials derived from VARONIC® T-210 such as 5398-21, which in turn are more absorbent than materials derived from VT-2085 such as 5398-100, which is probably due to the increased EO content. 5398-7, a quaternized amine ethoxylate (not an ester), proved (as expected) to be a very poor, again confirming the need for at least two fatty acid groups in the molecule.

TABLE SW/HW-1

Testing Results for SW/HW (Lot 1)

| Debonder used | Dosage (lbs./ton) | Tensile strength (kNm/kg) | Absorbency Rate from 0–5 sec. (g/g/sec) | Absorbency Capacity at 20 sec. (gH$_2$O/ g fiber) | Density (g/cm$^3$) |
|---|---|---|---|---|---|
| Blank | 0 | 10.77 | 0.14 | 1.76 | 0.342 |
| AROSURFr PA-801 | 3 | 6.17 | 0.14 | 1.67 | 0.330 |
|  | 5 | 4.96 | 0.13 | 1.68 | 0.329 |
|  | 8 | 3.74 | 0.13 | 1.62 | 0.321 |
| 5455-63 | 3 | 7.17 | 0.13 | 1.59 | 0.340 |
|  | 8 | 4.07 | 0.13 | 1.57 | 0.335 |
| 5455-63A | 3 | 6.62 | 0.12 | 1.52 | 0.351 |
|  | 5 | 4.87 | 0.12 | 1.45 | 0.337 |
|  | 8 | 3.77 | 0.14 | 1.64 | 0.330 |
| 5455-111 | 3 | 9.41 | 0.12 | 1.49 | 0.353 |
|  | 8 | 4.18 | 0.14 | 1.81 | 0.323 |
| 5455-111A | 3 | 7.05 | 0.12 | 1.49 | 0.340 |
|  | 5 | 5.22 | 0.14 | 1.82 | 0.335 |
|  | 8 | 4.07 | 0.13 | 1.60 | 0.330 |
| 5455-158 | 3 | 8.10 | 0.14 | 1.77 | 0.342 |
|  | 8 | 4.15 | 0.14 | 1.75 | 0.331 |
| 5455-158A | 3 | 6.69 | 0.11 | 1.54 | 0.348 |
|  | 5 | 5.15 | 0.12 | 1.58 | 0.340 |
|  | 8 | 3.53 | 0.13 | 1.65 | 0.326 |

The testing results for SW/HW (lot 1) set forth in Table SW/HW-1 compares the performance of certain Inventive Ester Quat esters of amine ethoxylates and their respective acid salts against the debonding and absorbence performance of the commercial product AROSURF® PA-801. The results show that the Inventive Ester Quat esters of the amine ethoxylates proved to be effective debonders with good absorbency profiles; their acid salts were stronger debonders as evidenced by increased tensile reductions, but absorbency was not compromised. In fact, the 5455-158/158A, which are the 1.5 esters, exhibited similar absorbencies as 5455-111/111, which are only monoesters. It can also be observed that increasing the canola acid content from one mole in 5455-111A to 1.5 mole in 5455-158A surprisingly had very little effect on absorbency, which is encouraging because the softness and biodegradability should be improved with more fatty groups present.

TABLE SW/HW-2

Testing Results for SW/HW (Lot 2)

| Debonder used | Dosage (lbs./ton) | Tensile strength (kNm/kg) | Absorbency Rate from 0–5 sec. (g/g/sec) | Absorbency Capacity at 20 sec. (gH$_2$O/g fiber) | Density (g/cm$^3$) |
|---|---|---|---|---|---|
| Blank | 0 | 12.91 | 0.14 | 1.67 | 0.356 |
| AROSURF ® PA-801 | 3 | 7.27 | 0.11 | 1.28 | 0.340 |
|  | 8 | 4.20 | 0.11 | 1.28 | 0.330 |
| 5455-158A | 3 | 7.09 | 0.11 | 1.38 | 0.338 |
|  | 5 | 5.64 | 0.11 | 1.41 | 0.341 |
|  | 8 | 3.84 | 0.12 | 1.51 | 0.330 |
| 5455-64 | 3 | 7.32 | 0.11 | 1.33 | 0.352 |
|  | 5 | 5.30 | 0.11 | 1.23 | 0.342 |
|  | 8 | 4.58 | 0.10 | 1.26 | 0.336 |
| 5455-112 | 3 | 7.52 | 0.13 | 1.49 | 0.340 |
|  | 8 | 4.54 | 0.11 | 1.30 | 0.335 |
| 5455-172 | 3 | 7.16 | 0.10 | 1.22 | 0.345 |
|  | 5 | 5.73 | 0.10 | 1.11 | 0.341 |
|  | 8 | 4.13 | 0.11 | 1.18 | 0.335 |
| 5455-159 | 3 | 7.18 | 0.11 | 1.28 | 0.350 |
|  | 5 | 5.00 | 0.11 | 1.33 | 0.341 |
|  | 8 | 4.21 | 0.11 | 1.28 | 0.339 |

The testing results for SW/HW (lot 2) set forth in Table SW/HW-2 shows the testing of eurcic fatty Inventive Ester Quat derivatives. In particular, tests of the respective acid salts and DMS quats of the esters of amine ethoxylates and tests of the DMS quat of the monoeurcic ester of canola amine+6 EO. The DMS quat of monoerucic ester of the canola amine+6 EO is a semi-liquid product at 100% actives that, because it is made exclusively from fatty acids derived from vegetable sources, would be an "all-vegetable" Inventive Ester Quat, with expected advantages of high biodegradability and low toxicity. This Inventive Ester Quat is similar to 5398-128 which is the dibehenic ester, but 5398-128 is a solid at 100% actives. Table SW/HW-2 shows that the eurcic derivative, 5455-172, was a strong debonder, but the presence of the long C22 chain adversely affects the absorbency. In general, the acid salts of the amine ethoxylates were absorbent. It can also be seen that increasing the canola content from one mole in 5455-112 to 1.5 mole in 5455-159 had only a slightly negative effect on absorbency: this is encouraging sign because the softness and biodegradability should be improved with more fatty groups present. As typical, the acid salt, 5455-158A, was more absorbent than the corresponding DMS salt, 5455-159.

TABLE 30SW/70HW-1

Testing Results for 30SW/70HW (Lot 1)

| Debonder used | Dosage (lbs./ton) | Tensile strength (kNm/kg) | Wet Tensile strength (kNm/kg) | Wet/Dry | Absorbency Rate from 0–5 sec. (g/g/sec) | Absorbency Capacity at 20 sec. (gH$_2$O/g fiber) |
|---|---|---|---|---|---|---|
| Blank | 0 | 12.60 | 0.35 | 36.18 | 0.14 | 1.49 |
| Blank (with 8 lbs./ton KYMENE ® 557 H) | 0 | 13.08 | 0.73 | 16.96 | 0.15 | 1.60 |
| AROSURF ® PA-801 (with 8 lbs./ton KYMENE ® 557 H) | 1 | 12.29 | 0.67 | 18.28 | 0.13 | 1.38 |
|  | 3 | 8.38 | 0.57 | 16.67 | 0.12 | 1.23 |
|  | 5 | 5.95 | 0.48 | 11.75 | 0.14 | 1.50 |
| 5326-199B (with 8 lbs./ton KYMENE ® 557 H) | 1 | 10.77 | 0.64 | 17.37 | 0.14 | 1.47 |
|  | 3 | 8.31 | 0.55 | 15.88 | 0.13 | 1.36 |
|  | 5 | 7.02 | 0.51 | 13.22 | 0.15 | i.50 |
| 5326-199D (with 8 lbs./ton KYMENE ® 557 H) | 1 | 12.22 | 0.62 | 20.91 | 0.14 | 1.43 |
|  | 3 | 8.70 | 0.53 | 16.67 | 0.14 | 1.45 |
|  | 5 | 6.06 | 0.52 | 12.92 | 0.15 | 1.50 |

The testing results for 30SW/70HW (lot 1) set forth in Table 30SW/70HW-1 shows the testing of debonders on handsheets that had been pretreated with a wet strength resin, KYMENE® 557 H, available from Hercules Corporation. The results show that there was no interference in performance of the Inventive Ester Quat debonders and the performance was comparable with commercial products.

TABLE CTMP/SW/HW-1

Testing Results for CTMP/SW/HW (Lot 1)

| Debonder used | Dosage (lbs./ton) | Tensile strength (kNm/kg) | Absorbency Rate from 0–5 sec. (g/g/sec) | Absorbency Capacity at 20 sec. (gH$_2$O/g fiber) |
|---|---|---|---|---|
| Blank 1 | 0 | 12.65 | 0.59 | 6.25 |
| Blank 2 | 0 | 13.02 | 0.59 | 6.25 |
| VARISOFT ® 3690 | 1 | 11.92 | 0.61 | 6.28 |
|  | 3 | 12.89 | 0.41 | 5.17 |
|  | 5 | 9.79 | 0.42 | 5.19 |
| 5455-111A | 1 | 11.45 | 0.56 | 6.20 |
|  | 3 | 10.51 | 0.60 | 6.39 |
|  | 5 | 9.43 | 0.58 | 6.27 |
| 5455-112 | 1 | 11.82 | 0.61 | 6.34 |
|  | 3 | 9.77 | 0.58 | 6.18 |
|  | 5 | 9.04 | 0.56 | 6.28 |

The testing results for 30SW/70HW (lot 1) set forth in Table 30SW/70HW-1 shows the testing of the Inventive Ester Quat acid or DMS salts of the monocanola ester of canola amine ethoxylate as compared against a known, standard absorbency aid. The results indicate that these compounds are very good absorbency aides and have the added benefit of being strong debonders and effective softeners. In general, the performance of the acid salt was comparable to the DMS salt in debonding and absorbency performance.

2. Paper Deinking Formulations and Example This example illustrates formulations of Inventive Ester Quats for use as deinking agents, for example, in recycled paper products. Generally such formulations are added to the pulper and/or to the slurry passing into the flotation cell. Furnishes that may be deinked with the compounds of the instant invention include waste paper with laser print, printed waste paper for a newsprint mill, ink fixed on pulp fiber of the printed waste paper product such as newspaper and magazines, and flexo news/magazine/newsprint, and the like.

The apparatus and processes for deinking operations is well-known to those of skill in the art. Typical apparatus and processes are disclosed in U.S. Pat. Nos. 5,622,597; 5,346,543; and 5,696,292, all of which are hereby incorporated by reference in their entireties. Additional apparatus and methods are disclosed in PCT WO/95/12026 and EP 0 726 246 A1, both of which are hereby incorporated by reference in their entireties.

In such a deinking process, the amount of the Inventive Ester Quat is about 0.01 wt. % to about 2.0 wt. %, preferably about 0.03 wt. % to about 1.0 wt. %, and most preferably about 0.05 wt. % to about 0.5 wt. % of the dry fiber. Other additives typically used include an ethylene oxide/propylene oxide nonionic (for example, alcohol, fatty acid, or alkylphenol derivatives) surfactant for frothing and foam control, sodium silicate, sodium hydroxide, hydrogen peroxide or sodium hypochlorite, and an EDTA or DTPA chelant. In addition, such cationic deinking agents may be combined with certain fatty acids, alkylene oxide adducts, and other solvents. Deinking is usually conducted on fiber slurries of 1% consistency at 40–50° C.

3. Fabric Softener Formulations and Examples

Example 5 illustrates formulations of Inventive Ester Quats in conventional solvent systems. A product was made by thoroughly blending the quaternary and solvent, then blending in the fragrance and then the water. The components and the amounts thereof were:

EXAMPLE 5

| Component | Amount (wt. %) |
| --- | --- |
| 5455-64 | 23.5 |
| Solvent (hexylene glycol) | 18–20 |
| Fragrance, dye, preservative, and other additives | as needed |
| Deionized water | to 100 |

Additional formulations employing another solvent system include Example 6 and Example 7, both made by the procedure disclosed in Example 5.

EXAMPLE 6

| Component | Amount (wt. %) |
| --- | --- |
| 5455-64 | 23.5 |
| TMPD | 7.5 |
| Hexylene glycol | 7.5 |
| Fragrance, dye, preservative, and other additives | as needed |
| Deionized water | to 100 |

EXAMPLE 7

| Component | Amount (wt. %) |
| --- | --- |
| 5455-64 | 11.8 |
| 5455-112 | 11.8 |
| TMPD | 7.5 |
| Hexylene glycol | 7.5 |
| Fragrance, dye, preservative, and other additives | as needed |
| Deionized water | to 100 |

More generally, exemplary formulation guidelines for fabric softener compositions which include Inventive Ester Quats, include Examples 8 and 9, which may provide clear formulations.

EXAMPLE 8

Inventive Ester Quat Formulation in Conventional Solvent(s)

| Component | Amount (wt %) |
| --- | --- |
| Inventive Ester Quat | 15–20 |
| Solvent(s) (for example, isopropanol, hexylene glycol) | 20–30 |
| Fragrance, dye, preservative, and other additives | as needed |
| Deionized water | to 100 |

EXAMPLE 9

Inventive Ester Quat Formulation with Coupling Agent

| Component | Amount (wt.%) |
| --- | --- |
| Inventive Ester Quat | 15–25 |
| Coupling agent(s) (for example, diol or alkoxylate of structural formula (T) and/or hydroxyester of structural formula (E)) | 10–15 |
| Acid (for example, HCl) | to pH 2.5–4 |
| Fragrance, dye, preservative, and other additives | as needed |
| Deionized water | to 100 |

As disclosed above, the Inventive Ester Quats may be used either alone or in combination with other compounds. Such compounds may include conventional quats such as those set forth herein above (see E. ADDITIONAL QUATERNARY AMMONIUM COMPOUNDS).

EXAMPLE 10

High Solids Fabric Softener Formulation

| Component | Amount (wt. %) |
| --- | --- |
| 5455-159 | 10 |
| Canola-based TEA ester quat (DMS-based quat) | 15 |
| Fragrance, preservative, dye, and other additives | as needed, to 100 |

It is expected that the above formulations will have several advantages over conventional fabric softener formulations, in particular, they will have low VOCs, high flash points, high liquidity, ease of formulation, disperse readily into water, even cold water, without a viscosity increase as with conventional quats, exhibit good biodegradability, and have low odor. It is also expected that these Inventive Ester Quat formulations will provide improved softening performance of the formulation over an equivalent amount of dialkyl ester quat formulation absent Inventive Ester Quats and will provide a finer final particle size when so dispersed. Moreover, the Inventive Ester Quat formulations are expected to have improved fluidity and viscosity, even in high solids formulations, over conventional non-blended formulations, exhibit reduced staining, and provide high color and odor stability. It should also be noted that certain of the formulations may be clear and may provide clear compositions more readily (that is, over a greater concentration range with lower solvent concentrations) than conventional quaternary ammonium compounds.

4. Microemulsion Formulations and Examples

This example illustrates formulations of compounds according to the present invention that are formulated into a microemulsion. As noted above, such formulations generally include three components: (a) Inventive Ester Quat, (b) a solvatrope or coupling agent and blends thereof, and (c) an oil or hydrophobic organic component and blends thereof, which are blended in water.

Suitable solvatropes or coupling agents may be selected from the diols and alkoxylates corresponding to structural formulas (T) or (E), TMPD, TMPD alkoxylates, ethanol, isopropanol, butanol, 1,2-cyclohexanedimethanol (1,2-CHDM), 1,4-cyclohexanedimethanol (1,4-CHDM), HPHP glycol, isopentyldiol, 1,2-hexanediol, ethylene glycol butyl ether, hexylene glycol, 2-butoxyethanol (sold by Union Carbide under the tradename butyl CELLOSOLVE®), $C_6$–$C_{12}$ diols/triols and ester diols/triols, glycol ethers, and the like. Oils and hydrophobic organic components may be selected from the fatty $C_8$–$C_{22}$ methyl esters, such as methyl oleate, mineral seal oils, silicone oils, fatty acids, monoglycerides, diglycerides, triglycerides, dialkyl esters, and the like, depending on the application. The methyl esters are the preferred oil based on performance and biodegradability, although mineral seal oil is preferred in car drying aid applications.

An example of such a microemulsion is the following formulation.

EXAMPLE 11

Microemulsion Formulation

| Component | Amount (wt. %) |
| --- | --- |
| 5455-159 | 15 |
| Isopropanol | 2.6 |
| TMPD/CHDM (80%/20%) | 11.7 |
| Methyl oleate | 18.0 |
| Fragrance, dye, preservative, and other additives | as needed |
| Deionized water | to 100 |

5. Emulsifier Formulations and Examples

This example illustrates formulations of Inventive Ester Quats for use as emulsifiers, for example, for agricultural emulsifiers or asphalt emulsifiers. In a typical formulation, the compound according to structural formula (1) is used as an emulsifier for organic compounds, for example, when formulated with pesticides, other surfactants and dispersants, and water, the resulting formulation would make a useful agricultural pesticide spray, the compound according to structural formula (1) encourages the organic components to remain dispersed in the water, allowing efficient transfer and coverage in treating plants. As will be appreciated, less hydrophobic examples of Inventive Ester Quats are used than those examples that would typically be used in other applications.

Example 12 illustrates formulations of Inventive Ester Quats for use as a herbicide emulsion agent. A Inventive Ester Quat or mixture thereof is added to a solvent or solvent mixture and water and a herbicide is incorporated therein and an emulsion formed. The amount of the quaternary compound is generally from about 5 wt. % to about 50 wt. %, preferably from about 10 wt. % to about 40 wt. %, most preferably from about 15 wt. % to about 30 wt. %, of the herbicide concentrate composition. A typical formulation might be:

EXAMPLE 12

Herbicide Concentrate Emulsion Formulation

| Component | Amount (wt. %) |
| --- | --- |
| 5398-1 | 20.0 |
| Propylene glycol | 4.0 |
| Water | 2.0 |
| $C_{10}$—$C_{12}$ alcohol + 9 moles EO | 3.0 |
| Glufosinate herbicide | 71.0 |

Example 13 illustrates formulations of Inventive Ester Quats for use as a pesticide emulsion agent formulation. Unlike Example 12, Example 13 does not incorporate the pesticide itself, instead an appropriate amount of pesticide must be added to the pesticide emulsion agent formulation to make a pesticide emulsion concentrate, which is diluted with water by the user and applied in the dilute form. In general, only 10-30 wt. % of the pesticide emulsion agent formulation is used to in the pesticide emulsion concentrate, that is, there is 70–90 wt. % pesticide in the pesticide emulsion concentrate, which is the form it will generally be commercialized. The final customer will then dilute the pesticide emulsion concentrate (pesticide/emulsifier package) into water for actual application of pesticide.

In such a pesticide emulsion agent formulation, a Inventive Ester Quat or mixture thereof is added to a solvent or solvent mixture and water and a pesticide is incorporated therein and an emulsion formed. The amount of the quaternary compound is generally from about 20 wt. % to about 70 wt. %, preferably from about 15 wt. % to about 50 wt. %, most preferably from about 20 wt. % to about 40 wt. %, of the pesticide emulsion agent composition. A typical emulsion agent formulation might be:

EXAMPLE 13

Pesticide Emulsion Agent Formulation

| Component | Amount (wt. %) |
| --- | --- |
| 5398-1 or 5455-111 | 40.0 |
| Phosphate ester | 6.0 |
| Water | 2.0 |
| $C_{10}$—$C_{12}$ alcohol + EO/PO block copolymer | 52.0 |

As noted above, the Inventive Ester Quats may also be used as an asphalt emulsifier as an additive for asphalt. As with the previous emulsifier formulations, the Inventive Ester Quat is prepared having less hydrophobic character than those that would typically be employed in other applications. If the resulting compound is not quaternized or quaternized to a limited extent, for example, only 0.5 mole of DMS per mole of quaternary compound, the possible applications in asphalt products are as a cationic rapid set (CRS) emulsion for chip seal, as a cationic medium set (CMS) for mixing grade applications, in a slurry seal or microsurfacing application, or in a roofing and driveway sealer. The amount of the Inventive Ester Quat in such an application would likely include from about 0.15 wt. % to about 2.0 wt. %, preferably about 0.20 wt. % to about 0.75 wt. %, and most preferably about 0.25 wt. % to about 0.65 wt. %, of the asphalt. Generally the fatty amine should be protonated in order to dissolve in the water. The pH of the emulsifier solution should be less than about 6.5, and may be adjusted with any strong acid to have a pH of between about 1.0 and about 5.0, preferably between about 2.0 to about 4.0, most preferably between about 2.0 and about 3.0.

If the compound is fully quaternized, the possible applications in asphalt products are as a cationic slow set emulsion, cationic quick set emulsion, tack coat, fog seal, base stabilization, prime coat, slurry seal, microsurfacing, industrial asphalt emulsion, or filled asphalt emulsion. The amount of the Inventive Ester Quat in such an application would likely include from about 0.1 wt. % to about 8.0 wt. %, preferably about 0.20 wt. % to about 5.0 wt. %, and most preferably about 0.5 wt. % to about 2.0 wt. %, of the asphalt. Generally the fatty amine should be protonated in order to dissolve in the water. The pH of the emulsifier solution should be less than about 7.0, and may be adjusted with any strong acid to have a pH of between about 1.0 and about 5.0, preferably between about 2.0 to about 4.0, most preferably between about 2.0 and about 3.0.

6. Oil Field Formulations and Examples

A first example illustrates formulations of Inventive Ester Quats for use in corrosion inhibition, for example, for lubricating oil or oil field use. A Inventive Ester Quat or mixture thereof is added to lubricating or other oils as a corrosion inhibitor. The Inventive Ester Quat may be used alone or in combination with a surfactant and/or coupling agent, which may be incorporated with the polyamine in a formulation or applied separately. When used, an effective amount is applied to the oil or oil mixture that will come in contact with the metal. The term "effective amount" denotes the amount of quaternary compound that would be effective to inhibit corrosion. In general, the amount of the polyamine compound ranges from about 0.001 wt. % to about 5 wt. %, preferably from about 0.01 wt. % to about 1 wt. %, most preferably from about 0.01 wt. % to about 0.5 wt. %, of the oil mixture in which it is used.

A second example illustrates formulations of Inventive Ester Quats for use in a lubricant and anti-balling agent for silicate muds and other water-based muds, for example, to lubricate drill strings to prevent stuck pipe, bit-balling, or string balling associated with drilling wells. The apparatus for drilling and general lubrication processes in well-known to those of skill in the art, and are disclosed. for example, in U.S. Pat. Nos. 5,586,608;5,593,954; and 5,639,715, all of these patents being herein incorporated by reference in their entireties. In this lubrication process, a Inventive Ester Quat or mixture thereof is added to lubricating or other oils effective to inhibit stuck pipe, bit balling, or string balling. The Inventive Ester Quat may be used alone or in combination with a surfactant and/or coupling agent, for example, propylene glycols or ethoxylated glycols, which may be incorporated with the polyamine in a formulation or applied separately. Of particular use are the oilfield products available from Witco Corporation under the tradename WITBREAK™, such as WITBREAK™ DPG-484. When used, an effective amount of polyarnine is applied to the lubricant mixture as used in the drilling operation. The term "effective amount" denotes the amount of polyamine compound that would be effective to inhibit stuck pipe, bit balling, or string balling. In general, the amount of the quaternary compound ranges from about 0.001 wt. % to about 5 wt. %, preferably from about 0.01 wt. % to about 2 wt. %, most preferably from about 0.05 wt. % to about 0.5 wt. %, of the lubricating mixture in which it is used. If used in a formulation, a typical formulation might be:

EXAMPLE 14

Lubricant and Anti-Balling Agent Formulation

| Component | Amount (wt. %) |
|---|---|
| 5455-64 | 50 |
| Surfactant or coupling agent | 50 |

7. Organoclays and Organoclay Formulations

Organoclays are the reaction product of certain clays, for example, smectite-type clays including hectorite and bentonite, such as those available from the Rheox Company under the tradename BENTONE™ 27, 34 and 38 or from Southern Clay Products under the tradename BENTOLITE™ L; or other suitable clays such as attapulgite clay) and one or more quaternary ammonium compounds (see, for example, U.S. Pat. Nos. 5,759,938; 5,718,841; 5,429,999; 5,336,647; 5,151,155; 5,075,033; 5,034,136; 4,444,665; 4,105,578; and 4,103,047, which are each incorporated by reference in their entireties). Organoclays have many uses, for example, as thickeners and rheological additives (see U.S. Pat. Nos. 5,735,943; 4,894,182; 4,664,820; 4,450,095; and 4,434,075, which are each incorporated by reference in their entireties), as oil spill flocculating agents (see U.S. Pat. No. 5,725,805, which is incorporated by reference in its entirety), as soil remediation agents, as drilling muds, as an agricultural adjuvant/carrier for pesticides or herbicides, or as a deinking agent (see U.S. Pat. No. 5,336,372, which is incorporated by reference in its entirety). Organoclay compositions according to the instant invention would be useful as rheological additives in both non-aqueous and aqueous systems such as inks, paints, varnishes, enamels, waxes, paint-varnishes, oil base drilling fluids, lubricants and greases, polyesters, epoxy resins, adhesives, sealants, cosmetics, detergents, and the like.

Inventive Ester Quats would generally be incorporated into the organoclays using methods known to those of skill in the art and any appropriate method may be used. Such methods may include the in situ formation of organoclays during application by adding the clay component and the Inventive Ester Quat component to the site where the organoclay is desired, for example, in a deinking tank. It should be noted that because of the unusual liquidity and viscosity characteristics of many Inventive Ester Quats, methods of making organoclays that are appropriate or possible for Inventive Ester Quats may be difficult or impossible to use with conventional quats. For example, Inventive Ester Quats may be incorporated into organoclays without using solvents, such as isopropyl alcohol, which is common and essential for many conventional quats to obtain appropriate handling characteristics. The present invention provides a novel organophilic clay or organoclay composition comprising the reaction product of: (a) one or more clays; and (b) one or more Inventive Ester Quats. Generally, according to the present invention, the clay is reacted with the quaternary reactant, which includes one or more Inventive Ester Quats and optionally other conventional quat components, present in an amount of between about 60% to about 180%, more preferably between about 70% to about 160%, and most preferably between about 80% to 140% of the cation exchange capacity (CEC) of the clay. The preferred clays are smectite-type clays, such as hectorite and bentonite. The clays used to prepare the organoclays of this invention are cation-exchangeable clays which have a CEC of about 50 or greater milliequivalents per 100 grams of clay, 100 percent active basis (i.e. beneficiated and essentially free of non-clay impurities). The CEC of the clay can be determined using methods known to those of skill in the art, for example, the methylene blue spot test. Most commercially available bentonite and hectorite clays typically have a CEC of about 100.

The organoclays, depending on the application, may also be mixed with one or more fibrous materials including organic fibers such as paper pulp, cotton fiber, wool, hemp, and vegetable fiber, rayon, and polyesters, as well as non-organic fibers, such as glass fiber. If such a organoclay-fiber composition is desired, the fibrous material is incorporated into the organoclay material during use or is incorporated into the organoclay material and the resultant product is recovered, dried, and ground to obtain the final product ready for use.

The organoclay materials according to the instant invention have many applications as a rheological additive or thixotropic agent in many systems, for example, laundry and debonding formulations, or in organic systems containing asphalt, creosote, and pitch. For example, it is today common practice to use spray equipment to apply asphalt for use as a protective coating to surfaces. Spraying allows a large amount of the product to be applied in a short time as spraying permits constant operation by the connection of a product reservoir with pressurizing equipment, a pipeline, and a spray head. To be successfully applied using spray apparatus, however, asphalt must be capable of being made very liquid and "sprayable" and, at the same time, the asphalt must not run or drip and must quickly, if not nearly instantaneously, become highly viscous following application. To achieve both of these effects, organoclays according to the instant invention may be employed as rheological additives or thixotropic agents, by incorporation of the organoclays into the asphalt, which is normally heated to approximately 50° C. or higher to make the asphalt less viscous, facilitating dispersion of the organoclays into the system. Similarly, creosote oil, an oily product of tar distillation, used in wood treatment as a protective coating for exposed wooden surfaces and fruit and walnut trees, is gum-like and highly viscous at room temperature, requires the addition of thixotropic agents for its successful application. Pitch, the non-volatile residue of coal tar after fractional distillation to remove lighter components, mastic, a glass-like yellow substance used in adhesives, and heavy resins, gums, highly viscous waxes, and the like, all pose hurdles similar to the application of asphalt and creosote, which may be overcome using the organoclays of the instant invention. The organoclays of the instant invention are dispersed using mixing and dispersion machinery into organic fluid systems in amounts sufficient to obtain the desired rheological properties, such as high viscosity at low shear rates, control of sagging of fluid fills, and prevention of settling. Amounts of the inventive organophilic clay/fiber thixotropic agent employed in the organic system involved should be between about 0.1% and about 10% based on the weight of the system, and preferably between 0.3% and 5.0%, to yield the desired rheological and thixotropic effects.

8. Mineral and Coal Dewatering Formulations and Example

This example illustrates formulations of Inventive Ester Quats for use as a mineral and coal dewatering agent, for example, for removal of water by means of a filtration dewatering apparatus known to those of skill in the art. In this process, a Inventive Ester Quat or mixture thereof is added to the mineral slurry prior to mechanical dewatering, the process becoming more effective as a result. The amount of the quaternary compound is generally from about 20 wt. % to about 95 wt. %, preferably from about 30 wt. % to about 80 wt. %, most preferably from about 50 wt. % to about 75 wt. %, of the dewatering agent formulation. A typical formulation might be:

EXAMPLE 15

Mineral and Coal Dewatering Agent Formulation

| Component | Amount (wt. %) |
| --- | --- |
| 5398-128 | 70.0 |
| TMPD + 1 mole EO | 20.0 |
| Nonionic surfactant | 10.0 |

9. Personal Care Formulations and Examples

These examples illustrate formulations of Inventive Ester Quats for use in personal care formulations, for example, for hair conditioners and skin conditioners.

EXAMPLE 16

Hair Conditioner Formulation

| Component | Amount (wt. %) |
| --- | --- |
| 5455-159 | 1.2 |
| Cetyl Alcohol | 2.0 |
| Ceteareth-20 (cetearyl alcohol ethoxylated with 20 moles of EO), available from Witco Corporation under the tradename VARONIC ® 63-E20 | 1.0 |
| Fragrance, dye, preservative, and other additives | as needed |
| Deionized water | to 100 |

EXAMPLE 17

Microemulsion Hair Conditioner Formulation

| Component | Amount (wt. %) |
| --- | --- |
| 5398-119 | 1.8 |
| Mineral oil (available from Witco Corporation under the tradename KAYDOL ® | 1.8 |
| TMPD + 1 EO | 1.2 |
| Fragrance, dye, preservative, and other additives | as needed |
| Deionized water | to 100 |

As with the microemulsion example of Example 11, personal care microemulsion formulations such as Example 17, include three components: (a) Inventive Ester Quat, (b) a solvatrope or coupling agent and blends thereof, and (c) an oil or hydrophobic organic component and blends thereof, which are blended in water. In such a formulation the amount of the Inventive Ester Quat is about 0.1 wt. % to about 65 wt. % of the formulation, preferably about 0.1 wt. % to about 35 wt. %, and most preferably about 0.1 wt. % to about 5 wt. %; the amount of solvatrope or coupling agent is about 0.1 wt. % to about 65 wt. % of the formulation, preferably about 0.1 wt. % about 35 wt. %, and most preferably about 0.1 wt. % to about 5 wt. %; the amount of oil or hydrophobic organic component is about 0.1 wt. % to 65 wt. % of the formulation, preferably about 0.1 wt. % to about 35 wt. %, and most preferably about 0.1 wt. % to about 5 wt. %; and the amount of water is about 20 to 99.7 wt. % of the formulation, preferably about 35 wt. % to about 99.7 wt. %, and most preferably about 65 wt. % to about 99.7 wt. %. Suitable solvatropes or coupling agents may be selected from the diols and alkoxylates corresponding to structural formulas (T) or (E), hydroxypivalyl hydroxypivalate and its alkoxylated derivatives, TMPD, TMPD alkoxylates, ethanol, isopropanol, butanol, 1,2-cyclohexanedimethanol (1,2-CHDM), 1,4-cyclohexanedimethanol (1,4-CHDM), HPHP glycol, isopentyldiol, 1,2-hexanediol, ethylene glycol butyl ether, hexylene glycol, isoprene glycol (3-methyl-1,3-butanediol), sorbitan ethoxylates, 2-butoxyethanol (sold by Union Carbide under the tradename butyl CELLOSOLVE®), $C_6$–$C_{12}$ diols/triols and ester diols/triols and their alkoxylated derivatives, glycol ethers, and the like. Oils and hydrophobic organic components may be selected from the fatty $C_8$–$C_{22}$ methyl esters, such as methyl oleate, mineral seal oils, silicone oils, fatty acids, monoglycerides, diglycerides, triglycerides, dialkyl esters, and the like, depending on the application.

Examples 18 and 19 provide examples of suitable hand lotions or skin conditioners.

EXAMPLE 18

Skin Conditioner Formulation

| Component | Amount (wt. %) |
|---|---|
| 5398-128 | 1.2 |
| Glyceryl stearate | 1.0 |
| Stearic acid | 2.0 |
| Cetyl alcohol | 2.0 |
| Glycerine (available from Witco Corporation under the tradename KEMSTRENE ®) | 1.6 |
| Mineral oil (available from Witco Corporation under the tradename KAYDOL ®) | 6.0 |
| PEG-30 glyceryl cocoate (available from Witco Corporation under the tradename VARONIC ® LI-63) | 1.6 |
| Fragrance, dye, preservative, and other additives | as needed |
| Deionized water | to 100 |

EXAMPLE 19

Skin Conditioner Formulation

| Component | Amount (wt. %) |
|---|---|
| 5455-159 | 1.2 |
| Glyceryl stearate | 1.0 |
| Stearic acid | 2.0 |
| Cetyl alcohol | 2.0 |
| Glycerine (available from Witco Corporation under the tradename KEMSTRENE ®) | 1.6 |
| Mineral oil (available from Witco Corporation under the tradename KAYDOL ®) | 6.0 |
| PEG-30 glyceryl cocoate (available from Witco Corporation under the tradename VARONIC ®LI-63) | 1.6 |
| Fragrance, dye, preservative, and other additives | as needed |
| Deionized water | to 100 |

It is understood that many of the examples and claims presented include components that are salts, that is, they include an anion and a cation. It is understood by those of skill in the art that the identity of the anion or cation of a given compound may not be crucial in the activity of the compound for a given purpose (that is, it may constitute a spectator ion) and an appropriate substitute may be made therefor. Thus, with regard to the Inventive Ester Quats, the counteranion $A^-$ may be, for example, chloride, bromide, methyl sulfate, ethyl sulfate, acetate, citrate, or salicylate or the like. Similarly, the sodium ion present in many of the anionic surfactants claimed and presented in the examples above may be replaced by other cations, such as potassium ion or ammonium ion, without appreciably affecting the performance of the anionic surfactant. Furthermore, with regard to the other components that may be salts that are be added to the composition or subsequently added to the composition, for example, viscosity modifiers, the component includes all similar compounds, that is, compounds where the ions are substituted by any other ion which is not significantly deleterious to the desired chemical or physical properties of the overall compound in its intended use. It is therefore understood that such ion substitution is well-known in the art and all such possibilities and equivalents are intended to be embraced within the appended claims.

As noted above, the examples provided are intended to further describe the aspects of the present invention. The examples are illustrative only and are not to be construed as limiting the scope of that which is regarded as the invention. Therefore, the scope of the present invention is only to be limited by the following claims and the equivalents thereto. In the specification and claims, the terms "comprise", "comprising", or "comprises" are intended to convey that the composition or formulation has or includes the recited components, but does not exclude other non-recited components.

What is claimed is:

1. A composition comprising a compound of structural formula (1B):

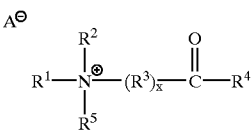

(1B)

wherein
$R^1$ is a $C_{14}$ to $C_{22}$ hydrocarbyl group;
$R^2$ is hydrogen or a $C_1$ to $C_{22}$ hydrocarbyl group, or is

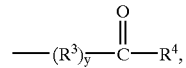

or $(R_3)_y H$, where y is 1 to 100;
each $R^3$ is independently selected from a group consisting of an ethylene oxide group ($C_2H_4O$), a propylene oxide group ($C_3H_6O$), a butylene oxide group ($C_4H_8O$) and mixtures thereof;
each $R_4$ is a $C_3$ to $C_{21}$ hydrocarbyl group;
$R^5$ is hydrogen or a $C_1$ to $C_8$ hydrocarbyl group; and
x is 3 to 100; and
$A^-$ is an anion; and
a quaternary compound of the structural formula:

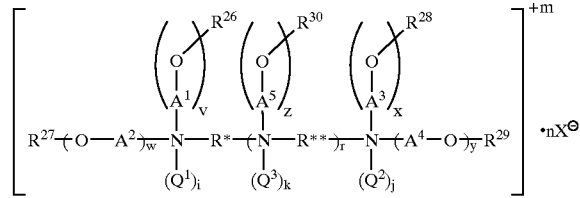

wherein each of $R^*$ and $R^{**}$ is independently a linear, branched or cyclic alkylene group containing 2 to 12 carbon atoms, wherein no two nitrogen atoms are separated by fewer than 2 carbon atoms;
each of $A^1, A^2, A^3, A^4$, and $A^5$ is independently a straight or branched alkylene containing 2 to 4 carbon atoms;
each of $R^{26}, R^{27}, R^{28}, R^{29}$, and $R^{30}$ is independently —H or $R^A C(O)$— wherein $R^A$ is straight or branched alkyl or alkenyl containing 7 to 21 carbon atoms and 0 to 4 carbon-carbon double bonds; provided that at least one of $R^{26}, R^{27}, R^{28}, R^{29}$, or $R^{30}$ is $R^A C(O)$—;

each of $Q^1$, $Q^2$ and $Q^3$ is independently —H, —CH$_3$, —C$_2$H$_5$, —C$_3$H$_7$, —C$_4$H$_5$, benzyl, —CH$_2$COOH, or —CH$_2$COOX$^{31}$; or, if R* is a —CH$_2$CH$_2$— group, $Q^1$ and $Q^3$ together or $Q^1$ and $Q^2$ together can be a —CH$_2$CH$_2$— group to form a six-membered piperazine ring; or, if R** is a —CH$_2$CH$_2$— group, $Q^2$ and $Q^3$ together can be a —CH$_2$CH$_2$— group to form a six-membered piperazine ring;

m is 0 to 4; r is 0 to 2; each of v, w, x, y, and z is independently 1 to 8;

i is 0 to 1, j is 0 to 1, and each k is 0 to 1, and the sum of (i+j+k) is 0 to; 3 with the proviso that when r=2, then the sum of (i+j+k) is 4 each X$^-$ is independently an anion selected from the group consisting of fluoride, chloride, bromide, iodide, chlorite, chlorate, hydroxide, hypophosphite, phosphite, phosphate, carbonate, formate, acetate, lactate, oxalate, methyl sulfate, ethyl sulfate, benzoate, and salicylate; and n is the number of moles of X$^-$ needed to give the quaternary ammonium compound a zero net charge.

2. The composition according to claim 1, wherein $R^1$, $R^2$, $R_4$, and $R^5$ are each independently selected from the group consisting of aliphatic groups, cycloaliphatic groups, aryl groups, alkaryl groups, and aralkyl groups.

3. The composition according to claim 2, wherein $R^1$, $R^2$, $R_4$, and $R^5$ are each independently an aliphatic group.

4. The composition according to claim 3, wherein $R^1$, $R^2$, $R^4$, and $R^5$ are each independently selected from the group consisting of a linear or branched alkyl group and alkenyl group.

5. The composition according to claim 1, wherein x is 3 to 50.

6. The composition according to claim 1 wherein $R^1$ is a linear alkyl or alkylene group containing 14 to 20 atoms.

7. The composition according to claim 6, wherein $R^1$ is selected from the group consisting of stearyl, tall oil fatty acid, soya, tallow, canola, and oleyl.

8. The composition according to claim 1, wherein $R^2$ is a linear or branched alkyl or alkylene group containing 1 to 18 carbon atoms.

9. The composition according to claim 1, wherein $R^2$ is

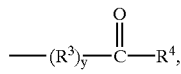

or $(R^3)_yH$, and y is 3 to 50.

10. The composition according to claim 1, wherein each $R^4$ is independently a linear, branched, or cyclic alkyl or alkylene group containing 13 to 21 carbon atoms.

11. The composition according to claim 1, wherein $R^5$ is hydrogen or a linear, branched, or cyclic alkyl or alkylene group containing 1 to 6 carbon atoms or benzyl.

12. The composition according to claim 11, wherein $R^5$ is hydrogen, methyl, ethyl, or benzyl.

13. The composition of claim 1, wherein A$^-$ is selected from the group consisting of fluoride, chloride, bromide, iodide, chlorite, chlorate, hydroxide, hypophosphite, phosphite, phosphate, carbonate, formate, acetate, citrate, lactate, oxalate, methyl sulfate, ethyl sulfate, benzoate, and salicylate.

14. The composition according to claim 1, wherein the composition comprises a mixture of a plurality of compounds of structural formula (1B).

15. The composition according to claim 1, further comprising a second surfactant selected from the group consisting of anionic surfactants, cationic surfactants, zwitterionic surfactants, nonionic surfactants, amphoteric surfactants, and blends thereof.

16. The composition according to claim 15, wherein the second surfactant is a quaternary compound selected from compounds of the following structural formulas:

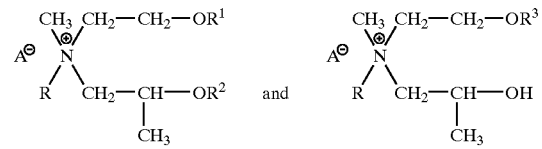

wherein R is —H, —CH$_3$ or —C$_2$H$_5$; $R^{31}$, $R^{32}$, and $R^{33}$ are each independently of one another fatty acid radicals having 6–22 carbon atoms; and X$^-$ is an inorganic or organic anion selected from the group consisting of fluoride, chloride, bromide, iodide, chlorite, chlorate, hydroxide, hypophosphite, phosphite, phosphate, carbonate, formate, acetate, lactate, oxalate, methyl sulfate, ethyl sulfate, benzoate, and salicylate.

17. The composition according to claim 1, wherein the composition comprises a mixture of two or more different quaternary compounds.

18. The composition according to claim 1, further comprising: a sovatrope or coupling agent or blends thereof; and an oil or hydrophobic organic component and blends thereof.

19. The composition according to claim 18, wherein the composition further comprises water.

20. The composition according to claim 19, wherein the amount of the compounds of structural formula (1B) is about 0.1 wt. % to about 65 wt. % of the composition; the amount of solvatrope or coupling agent is about 0.1 wt. % to about 65 wt. % of the composition, the amount of oil or hydrophobic organic component is about 0.1 wt. % to 65 wt. % of the formulation, and the amount of water is about 20 to 99.7 wt. % of the composition.

21. The composition according to claim 19, wherein the solvatrope or coupling agent is selected from the group consisting of: hydroxypivalyl hydroxypivalate and its alkoxylated derivatives, TMPD, TMPD alkoxylates, ethanol, isopropanol, butanol, 1,2-cyclohexanedimethanol, 1,4-cyclohexanedimethanol, HPHP glycol, isopentyldiol, 1,2-hexanediol, ethylene glycol butyl ether, hexylene glycol, isoprene glycol, sorbitan ethoxylates, 2-butoxyethanol, $C_6$–$C_{12}$ diols/triols and ester diols/triols and their alkoxylated derivatives, glycol ethers, and mixtures thereof.

22. The composition according to claim 19, wherein the oil or hydrophobic organic component is selected from the group consisting of: fatty acids; fatty amides; fatty alcohols; fatty oils; fatty esters made from a $C_8$–$C_{22}$ fatty acid and a $C_1$–$C_8$ alcohol; dialkyl esters; mineral oil; mineral seal oils; silicone oils; petrolatums; monoglycerides; diglycerides; triglycerides; aliphatic, paraffinic, and naphthalinic hydrocarbons; oils and spirits; and mixtures thereof.

23. The composition according to claim 19, wherein the composition comprises a mixture of two or more different solvents or coupling agents.

24. The composition according to claim 19, wherein the composition is emulsified into a microemulsion.

25. A composition comprising a compound selected from the group consisting of compounds of the following structural formula (2A):

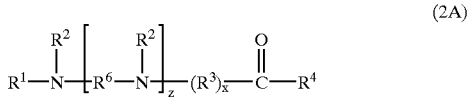
(2A)

and the protonated and quaternized derivatives thereof of the following structural formula (2B):

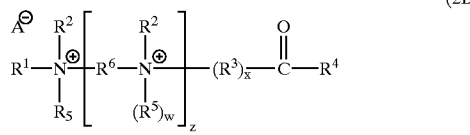
(2B)

wherein $R^1$ is a $C_{14}$ to $C_{22}$ hydrocarbyl group;

each $R^2$ is independently selected from the group consisting of hydrogen, a $C_1$ to $C_{22}$ hydrocarbyl group,

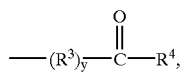

and $R^3)_yH$, where y is 1 to 100;

each $R^3$ is independently selected from the group consisting of an ethylene oxide group ($C_2H_4O$), a propylene oxide group ($C_3H_6O$), a butylene oxide group ($C_4H_8O$) and mixtures thereof;

each $R^4$ is independently a $C_3$ to $C_{21}$ hydrocarbyl group;

each $R^5$ is independently a hydrogen or a $C_1$ to $C_6$ hydrocarbyl group, where each w is independently 0 or 1;

each $R^6$ is independently a $C_1$ to $C_6$ hydrocarbyl group;

x is 3 to 100;

z is 1, 2, 3, 4 or 5; and $A^-$ is an anion that balances the charge of the compounds.

26. The composition according to claim 25, wherein $R^1$, $R^2$, $R^4$, $R^5$, and $R^6$ are each independently selected from the group consisting of aliphatic groups, cycloaliphatic groups, aryl groups, alkaryl groups, and aralkyl groups.

27. The composition according to claim 26, wherein $R^1$, $R^2$, $R^4$, and $R^5$ are each independently an aliphatic group.

28. The composition according to claim 27, wherein $R^1$, $R^2$, $R^4$, and $R^5$ is are each independently selected from the group consisting of a linear or branched alkyl group and alkenyl group.

29. The composition according to claim 25, wherein x is 3 to 50.

30. The composition according to claim 25, wherein z is 1 or 2.

31. The composition according to claim 25, wherein $R^1$ a linear alkyl or alkylene group containing 14 to 20 carbon atoms.

32. The composition according to claim 31, wherein $R^1$ is selected from the group consisting of stearyl, tall oil fatty acid, soya, tallow, canola, and oleyl.

33. The composition according to claim 25, wherein $R^2$ is a linear or branched alkyl or alkylene group containing 1 to 18 carbon atoms.

34. The composition according to claim 25, wherein $R^2$ is

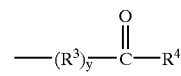

or $(R^3)_yH$, and y is 3 to 50.

35. The composition according to claim 25, wherein each $R^4$ is independently a linear, branched, or cyclic alkyl or alkylene group containing 13 to 21 carbon atoms.

36. The composition according to claim 25, wherein $R^5$ is hydrogen or a linear, branched, or cyclic alkyl or alkylene group containing 1 to 6 carbon atoms or benzyl.

37. The composition according to claim 30, wherein $R^5$ is hydrogen, methyl, ethyl, or benzyl.

38. The composition according to claim 25, wherein $R^6$ is a linear, branched, or cyclic alkyl or alkylene group containing 1 to 6 carbon atoms.

39. The composition according to claim 25, wherein $A^-$ is selected from the group consisting of fluoride, chloride, bromide, iodide, chlorite, chlorate, hydroxide, hypophosphite, phosphite, phosphate, carbonate, formate, acetate, citrate, lactate, oxalate, methyl sulfate, ethyl sulfate, benzoate, and salicylate.

40. The composition according to claim 25, wherein the composition comprises a mixture of two or more different compounds of structural formula (2A) or structural formula (2B).

41. The composition according to claim 25, further comprising a second surfactant selected from the group consisting of anionic surfactants, cationic surfactants, zwitterionic surfactants, nonionic surfactants, amphoteric surfactants, and blends thereof.

42. The composition according to claim 41, wherein the second surfactant comprises a quaternary compound.

43. The composition according to claim 42, wherein the quaternary compound comprises a compound of the following structural formula:

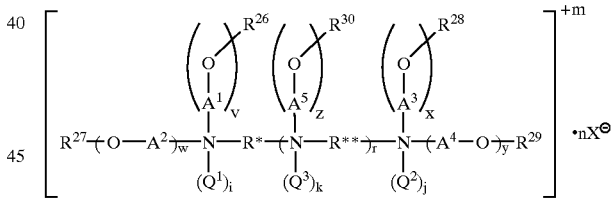

wherein each of R* and R** is independently a linear, branched or cyclic alkylene group containing 2 to 12 carbon atoms, wherein no two nitrogen atoms are separated by fewer than 2 carbon atoms;

each of $A^1$, $A^2$, $A^3$, $A^4$, and $A^5$ is independently a straight or branched alkylene containing 2 to 4 carbon atoms;

each of $R^{26}$, $R^{27}$, $R^{28}$, $R^{29}$, and $R^{30}$ is independently —H or $R^AC(O)$— wherein $R^A$ is straight or branched alkyl or alkenyl containing 7 to 21 carbon atoms and 0 to 4 carbon-carbon double bonds; provided that at least one of $R^{26}$, $R^{27}$, $R^{28}$, $R^{29}$, or $R^{30}$ is $R^AC(O)$—;

each of $Q^1$, $Q^2$ and $Q^3$ is independently —H, —$CH_3$, —$C_2H_5$, —$C_3H_7$, —$C_4H_5$, benzyl, —$CH_2COOH$, or —$CH_2COOX^-$; or, if R* is a —$CH_2CH_2$— group, $Q^1$ and $Q^3$ together or $Q^1$ and $Q^2$ together can be a —$CH_2CH_2$— group to form a six-membered piperazine ring; or, if R** is a —$CH_2CH_2$— group, $Q^2$ and $Q^3$ together can be a —$CH_2CH_2$— group to form a six-membered piperazine ring;

m is 0 to 4; r is 0 to 2; each of v, w, x, y, and z is independently 1 to 8;

i is 0 to 1, j is 0 to 1, and each k is 0 to 1, and the sum of (i+j+k) is 0 to 3, with the proviso that when r=2, then the sum of (i+j+k) is 4;

each $X^-$ is independently an anion selected from the group consisting of fluoride, chloride, bromide, iodide, chlorite, chlorate, hydroxide, hypophosphite, phosphite, phosphate, carbonate, formate, acetate, lactate, oxalate, methyl sulfate, ethyl sulfate, benzoate, and salicylate; and is the number of moles of $X^-$ needed to give the quaternary ammonium compound a zero net charge.

44. The composition according to claim 42, wherein the quaternary compound comprises a compound selected from compounds of the following structural formulas:

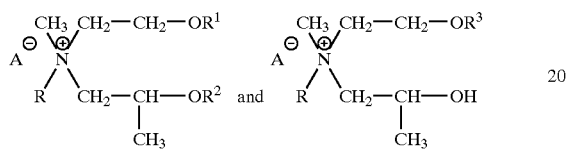 and 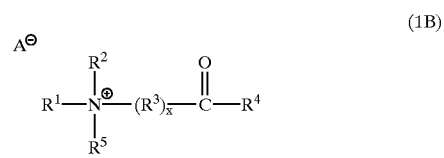

wherein R is —H, —$CH_3$ or —$C_2H_5$;

$R^{31}$, $R^{32}$, and $R^{33}$ are each, independently of one another, fatty acid radicals having 6–22 carbon atoms; and $X^-$ is an inorganic or organic anion selected from the group consisting of fluoride, chloride, bromide, iodide, chlorite, chlorate, hydroxide, hypophosphite, phosphite, phosphate, carbonate, formate, acetate, lactate, oxalate, methyl sulfate, ethyl sulfate, benzoate, and salicylate.

45. The composition according to claim 42, wherein the composition comprises a mixture of two or more different quaternary compounds.

46. The composition according to claim 25, further comprising: a solvatrope or coupling agent or blends thereof; and an oil or hydrophobic organic component and blends thereof.

47. The composition according to claim 46, wherein the composition further comprises water.

48. The composition according to claim 47, wherein the amount of the compounds of structural formula (2A) and structural formula (2B) is about 0.1 wt. % to about 65 wt. % of the composition; the amount of solvatrope or coupling agent is about 0.1 wt. % to about 65 wt. % of the composition, the amount of oil or hydrophobic organic component is about 0.1 wt. % to 65 wt. % of the formulation, and the amount of water is about 20 to 99.7 wt. % of the composition, preferably about 35 wt. % to about 99.7 wt. %.

49. The composition according to claim 47, wherein the solvatrope or coupling agent is selected from the group consisting of: hydroxypivalyl hydroxypivalate and its alkoxylated derivatives, TMPD, TMPD alkoxylates, ethanol, isopropanol, butanol, 1,2-cyclohexanedimethanol, 1,4-cyclohexanedimethanol, HPHP glycol, isopentyldiol, 1,2-hexanediol, ethylene glycol butyl ether, hexylene glycol, isoprene glycol, sorbitan ethoxylates, 2-butoxyethanol, $C_6$–$C_{12}$ diols/triols and ester diols/triols and their alkoxylated derivatives, glycol ethers, and mixtures thereof.

50. The composition according to claim 47, wherein the oil or hydrophobic organic component is selected from the group consisting of: fatty acids; fatty amides; fatty alcohols; fatty oils; fatty esters made from a $C_8$–$C_{22}$ fatty acid and a $C_1$–$C_8$ alcohol; dialkyl esters; mineral oil; mineral seal oils; silicone oils; petrolatums; monoglycerides; diglycerides; triglycerides; aliphatic, paraffinic, and naphthalinic hydrocarbons; oils and spirits; and mixtures thereof.

51. The composition according to claim 47, wherein the composition comprises a mixture of two or more different solvents or coupling agents.

52. The composition according to claim 47, wherein the composition is emulsified into a microemulsion.

53. A paper web comprising:

(a) papermaking fiber; and (b) a compound selected from compounds of the group consisting of compounds of the following structural formula (1)B):

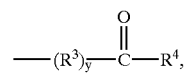 (1B)

wherein $R^1$ is a $C_{14}$ to $C_{22}$ hydrocarbyl group;

$R^2$ is hydrogen or a $C_1$ to $C_{22}$ hydrocarbyl group, or is

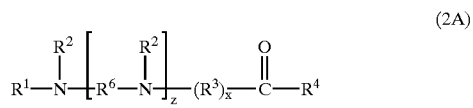

or $(R^3)_yH$, where y is 1 to 100;

each $R^3$ is independently selected from a group consisting of an ethylene oxide group ($C_2H_4O$), a propylene oxide group ($C_3H_6O$), a butylene oxide group ($C_4H_8O$) and mixtures thereof;

each $R^4$ is a $C_3$ to $C_2$, hydrocarbyl group;

$R^5$ is hydrogen or a $C_1$ to $C_8$ hydrocarbyl group; and x is 3 to 100; and $A^-$ is an anion.

54. A paper web comprising:

(a) papermaking fiber; and (b) a compound selected from compounds of the following structural formula (2A):

(2A)

and the protonated and quaternized derivatives thereof of the following structural formula (2B):

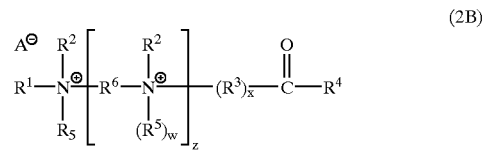 (2B)

wherein $R^1$ is a $C_{14}$ to $C_{22}$ hydrocarbyl group;

each $R^2$ is independently selected from the group consisting of hydrogen, a $C_1$ to $C_{22}$ hydrocarbyl group,

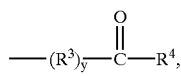

and $(R^3)_yH$, where y is 1 to 100;

each $R^3$ is independently selected from the group consisting of an ethylene oxide group ($C_2H_4O$), a propylene oxide group ($C_3H_6O$), a butylene oxide group ($C_4H_8O$) and mixtures thereof;

each $R^4$ is independently a $C_3$ to $C_{21}$ hydrocarbyl group;

each $R^5$ is independently a hydrogen or a $C_1$ to $C_6$ hydrocarbyl group, where each w is independently 0 or 1;

each $R^6$ is independently a $C_1$ to $C_6$ hydrocarbyl group;

x is 3 to 100;

z is 1, 2, 3, 4 or 5; and $A^-$ is an anion that balances the charge of the compounds.

55. A method of treating papermaking fibers comprising:

(a) adding papermaking fibers to an aqueous solution;

(b) adding a composition of claim 1 or 25 to the aqueous solution before, during, or after the point at which the papermaking fibers are added to the aqueous solution;

(c) allowing said compound to debond the papermaking fibers to a selected degree; and (d) removing the papermaking fibers from the aqueous solution.

56. A method of treating a paper web comprising applying to the paper web a composition which comprises at least one compound of structural formula (1B):

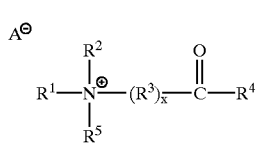
(1B)

wherein $R^1$ is a $C_{14}$ to $C_{22}$ hydrocarbyl group;

$R^2$ is hydrogen or a $C_1$ to $C_{22}$ hydrocarbyl group, or is

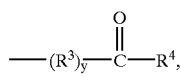

or $(R^3)_yH$, where y is 1 to 100;

each $R^3$ is independently selected from a group consisting of an ethylene oxide group ($C_2H_4O$), a propylene oxide group ($C_3H_6O$), a butylene oxide group ($C_4H_8O$) and mixtures thereof;

each $R^4$ is a $C_3$ to $C_2$, hydrocarbyl group;

$R^5$ is hydrogen or a $C_1$ to $C_8$ hydrocarbyl group; and x is 3 to 100; and $A^-$ is an anion;

or at least one compound of structural formula (2A):

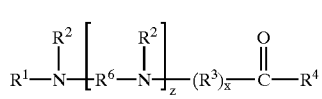
(2A)

or the protonated and quaternized derivatives thereof of the following structural formula (2B):

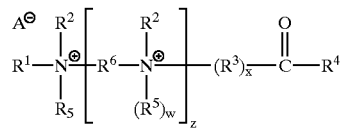
(2B)

wherein $R^1$ is a $C_{14}$ to $C_{22}$ hydrocarbyl group;

each $R^2$ is independently selected from the group consisting of hydrogen, a $C_1$ to $C_{22}$ hydrocarbyl group,

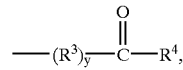

and $(R^3)_yH$, where y is 1 to 100;

each $R^3$ is independently selected from the group consisting of an ethylene oxide group ($C_2H_4O$), a propylene oxide group ($C_3H_6O$), a butylene oxide group ($C_4H_8O$) and mixtures thereof;

each $R^4$ is independently a $C_3$ to $C_{21}$ hydrocarbyl group;

each $R^5$ is independently a hydrogen or a $C_1$ to $C_6$ hydrocarbyl group, where each w is independently 0 or 1;

each $R^6$ is independently a $C_1$ to $C_6$ hydrocarbyl group;

x is 3 to 100;

z is 1, 2, 3, 4 or 5; and $A^-$ is an anion that balances the charge of the compounds.

57. The method of claim 56, wherein said applying includes spraying and printing.

58. An organoclay composition made by the reaction of:

(a) one or more clays;

(b) one or more compounds selected from the group consisting of:

(i) compounds of the following structural formula (1B):

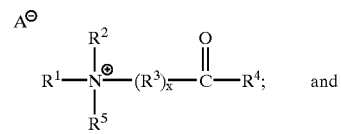
(1B)

and (ii) compounds of the following structural formula (2B):

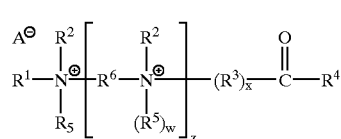
(2B)

wherein $R^1$ is a $C_{14}$ to $C_{22}$ hydrocarbyl group;

each $R^2$ is independently selected from the group consisting of hydrogen, a $C_1$ to $C_{22}$ hydrocarbyl group,

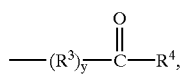

and $(R^3)_y H$, where y is 1 to 100;

each $R^3$ is independently selected from the group consisting of an ethylene oxide group ($C_2H_4O$), a propylene oxide group ($C_3H_6O$), a butylene oxide group ($C_4H_8O$) and mixtures thereof;

each $R^4$ is independently a $C_3$ to $C_{21}$ hydrocarbyl group;

each $R^5$ is independently a hydrogen or a $C_1$ to $C_6$ hydrocarbyl group, where each w is independently 0 or 1;

each $R^6$ is independently a $C_3$ to $C_8$ hydrocarbyl group;

x is 3 to 100;

z is 1, 2, 3, 4 or 5; and $A^-$ is an anion that balances the charge of the compounds; and (c) one or more quaternary compounds of the structural formula:

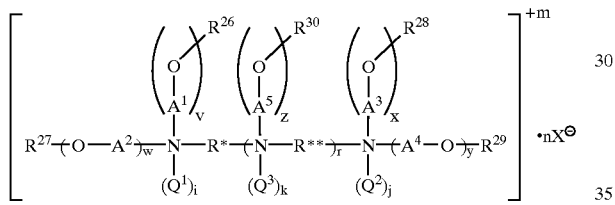

wherein each of R* and R** is independently a linear, branched or cyclic alkylene group containing 2 to 12 carbon atoms, wherein no two nitrogen atoms are separated by fewer than 2 carbon atoms;

each of $A^1$, $A^2$, $A^3$, $A^4$, and $A^5$ is independently a straight or branched alkylene containing 2 to 4 carbon atoms;

each of $R^{26}$, $R^{27}$, $R^{28}$, $R^{29}$, and $R^{30}$ is independently —H or $R^A C(O)$— wherein $R^A$ is straight or branched alkyl or alkenyl containing 7 to 21 carbon atoms and 0 to 4 carbon-carbon double bonds; provided that at least one of $R^{26}$, $R^{27}$, $R^{28}$, $R^{29}$, or $R^{30}$ is $R^A C(O)$—;

each of $Q^1$, $Q^2$ and $Q^3$ is independently —H, —$CH_3$, —$C_2H_5$, —$C_3H_7$, —$C_4H_5$, benzyl, —$CH_2COOH$, or —$CH_2COOX^-$; or, if R* is a —$CH_2CH_2$— group, $Q^1$ and $Q^3$ together or $Q^1$ and $Q^2$ together can be a —$CH_2CH_2$— group to form a six-membered piperazine ring; or, if R** is a —$CH_2CH_2$— group, $Q^2$ and $Q^3$ together can be a —$CH_2CH_2$— group to form a six-membered piperazine ring;

m is 0 to 4; r is 0 to 2; each of v, w, x, y, and z is independently 1 to 8;

i is 0 to 1, j is 0 to 1, and each k is 0 to 1, and the sum of (i+j+k) is 0 to; 3 with the proviso that when r=2, then the sum of (i+j+k) is 4;

each $X^-$ is independently an anion selected from the group consisting of fluoride, chloride, bromide, iodide, chlorite, chlorate, hydroxide, hypophosphite, phosphite, phosphate, carbonate, formate, acetate, lactate, oxalate, methyl sulfate, ethyl sulfate, benzoate, and salicylate; and n is the number of moles of $X^-$ needed to give the quaternary ammonium compound a zero net charge.

* * * * *